US012778429B2

(12) United States Patent
Qu et al.

(10) Patent No.: US 12,778,429 B2
(45) Date of Patent: Nov. 3, 2026

(54) METHODS, SYSTEMS AND DEVICES FOR UTILIZING MULTIPLE AF DISCRIMINATORS

(71) Applicant: Pacesetter, Inc., Sylmar, CA (US)

(72) Inventors: Fujian Qu, San Jose, CA (US); Nima Badie, Oakland, CA (US); Jong Gill, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 711 days.

(21) Appl. No.: 17/407,950

(22) Filed: Aug. 20, 2021

(65) Prior Publication Data

US 2022/0104774 A1 Apr. 7, 2022

Related U.S. Application Data

(60) Provisional application No. 63/087,620, filed on Oct. 5, 2020.

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0245* (2013.01); *A61B 5/0816* (2013.01); *A61B 5/1118* (2013.01); *A61B 5/352* (2021.01); *A61B 5/353* (2021.01); *A61B 5/355* (2021.01); *A61B 5/361* (2021.01); *A61B 5/686* (2013.01); *A61B 5/7221* (2013.01); *A61B 2560/0209* (2013.01)

(58) Field of Classification Search
CPC ....... A61B 5/0205; A61B 5/352; A61B 5/353; A61B 5/361; A61B 5/686
See application file for complete search history.

(56) References Cited

U.S. PATENT DOCUMENTS 5,755,739 A 5/1998 Sun et al.
7,167,747 B2 1/2007 Gunderson et al.
(Continued)

FOREIGN PATENT DOCUMENTS

EP 1615693 B1 1/2011
EP 2079520 B1 11/2013
(Continued)

*Primary Examiner* — Amanda L Steinberg
*Assistant Examiner* — Laura Hodge
(74) *Attorney, Agent, or Firm* — Pearl Cohen LLP

(57) ABSTRACT

Embodiments disclosed herein use multiple AF discriminators to determine whether to classify an AF detection as a false positive. One method includes detecting R-waves within an EGM or ECG signal, determining R-R intervals based on the R-waves, detecting AF based on the R-R intervals, and using one or more time-based AF discriminators to analyze one or more temporal features of the EGM or ECG signal within a window leading up to the AF detection to thereby determine whether to classify the AF detection as a false positive. In response to not classifying the AF detection as a false positive using the one or more time-based AF discriminators, one or more morphology-based AF discriminators are used to analyze one or more morphological features of the EGM or ECG signal within the window leading up to the AF detection to thereby determine whether to classify the AF detection as a false positive.

11 Claims, 25 Drawing Sheets

(51) Int. Cl.

| | |
|---|---|
| *A61B 5/0245* | (2006.01) |
| *A61B 5/08* | (2006.01) |
| *A61B 5/11* | (2006.01) |
| *A61B 5/352* | (2021.01) |
| *A61B 5/353* | (2021.01) |
| *A61B 5/355* | (2021.01) |
| *A61B 5/361* | (2021.01) |

(56) References Cited

U.S. PATENT DOCUMENTS

| | | | |
|---|---|---|---|
| 7,218,966 | B2 | 5/2007 | Haefner |
| 7,266,409 | B2 | 9/2007 | Gunderson |
| 7,283,863 | B2 | 10/2007 | Gunderson et al. |
| 7,333,855 | B2 | 2/2008 | Gunderson et al. |
| 7,412,282 | B2 | 8/2008 | Houben |
| 7,537,569 | B2 | 5/2009 | Sarkar et al. |
| 7,582,061 | B2 | 9/2009 | Li et al. |
| 7,623,911 | B2 | 11/2009 | Sarkar et al. |
| 7,630,756 | B2 | 12/2009 | Linker |
| 7,634,310 | B2 | 12/2009 | Lee et al. |
| 7,774,049 | B2 | 8/2010 | Ghanem et al. |
| 7,774,062 | B2 | 8/2010 | Kim et al. |
| 7,783,354 | B2 | 8/2010 | Gunderson |
| 7,818,056 | B2 | 10/2010 | Kim et al. |
| 7,831,301 | B2 | 11/2010 | Cao et al. |
| 7,894,893 | B2 | 2/2011 | Kim et al. |
| 7,912,545 | B2 | 3/2011 | Li et al. |
| 8,078,277 | B2 | 12/2011 | Gunderson et al. |
| 8,160,686 | B2 | 4/2012 | Allavatam et al. |
| 8,260,404 | B1 | 9/2012 | Bharmi et al. |
| 8,265,737 | B2 | 9/2012 | Warren et al. |
| 8,406,872 | B2 | 3/2013 | Stadler et al. |
| 8,437,840 | B2 | 5/2013 | Patel et al. |
| 8,437,851 | B2 | 5/2013 | Corbucci et al. |
| 8,473,042 | B2 | 6/2013 | McCarthy et al. |
| 8,506,500 | B2 | 8/2013 | Li et al. |
| 8,521,281 | B2 | 8/2013 | Patel et al. |
| 8,538,524 | B2 | 9/2013 | Rosenberg et al. |
| 8,560,058 | B2 | 10/2013 | Babaeizadeh et al. |
| 8,560,069 | B2 | 10/2013 | Zhang |
| 8,577,455 | B2 | 11/2013 | Mitrani et al. |
| 8,583,221 | B1 | 11/2013 | Patel et al. |
| 8,588,895 | B2 | 11/2013 | Sanghera et al. |
| 8,588,896 | B2 | 11/2013 | Allavatam et al. |
| 8,626,280 | B2 | 1/2014 | Allavatam et al. |
| 8,639,316 | B2 | 1/2014 | Sarkar |
| 8,744,559 | B2 | 6/2014 | Houben et al. |
| 8,750,994 | B2 | 6/2014 | Ghosh et al. |
| 8,774,909 | B2 | 7/2014 | Patel et al. |
| 8,781,585 | B2 | 7/2014 | Gunderson et al. |
| 8,792,971 | B2 | 7/2014 | Gunderson et al. |
| 8,886,296 | B2 | 11/2014 | Patel |
| 8,897,863 | B2 | 11/2014 | Linker |
| 8,914,106 | B2 | 12/2014 | Charlton et al. |
| 8,942,793 | B2 | 1/2015 | Eberle et al. |
| 9,101,278 | B2 | 8/2015 | Fischell et al. |
| 9,167,747 | B1 | 10/2015 | Andros et al. |
| 9,307,920 | B2 | 4/2016 | Mahajan et al. |
| 9,314,210 | B2 | 4/2016 | Li |
| 9,339,662 | B2 | 5/2016 | Allavatam et al. |
| 9,381,370 | B2 | 7/2016 | Gunderson |
| 9,468,766 | B2 | 10/2016 | Sheldon et al. |
| 9,675,261 | B2 | 6/2017 | Cao et al. |
| 9,682,238 | B2 | 6/2017 | Zhang et al. |
| 9,724,007 | B2 | 8/2017 | Cole |
| 9,962,100 | B2 | 5/2018 | Allavatam et al. |
| 9,993,653 | B2 | 6/2018 | Bardy et al. |
| 9,999,368 | B2 | 6/2018 | Perschbacher et al. |
| 10,004,418 | B2 | 6/2018 | Cao et al. |
| 10,183,171 | B2 | 1/2019 | Ostroff et al. |
| 10,194,816 | B2 | 2/2019 | Perschbacher et al. |
| 10,413,207 | B2 | 9/2019 | Sarkar et al. |
| 10,548,499 | B2 | 2/2020 | Bayasi et al. |
| 10,576,288 | B2 | 3/2020 | Cao et al. |
| 10,582,870 | B2 | 3/2020 | Allavatam et al. |
| 10,617,320 | B2 | 4/2020 | Mahajan et al. |
| 10,702,180 | B2 | 7/2020 | Perschbacher et al. |
| 10,709,379 | B2 | 7/2020 | Warren et al. |
| 11,304,646 | B2 * | 4/2022 | Thakur ................ A61B 5/0205 |
| 2008/0161870 | A1 | 7/2008 | Gunderson |
| 2010/0280567 | A1 | 11/2010 | Gunderson |
| 2011/0112597 | A1 * | 5/2011 | Snell .................... A61N 1/3702 607/27 |
| 2015/0045682 | A1 | 2/2015 | Sanghera et al. |
| 2016/0235317 | A1 * | 8/2016 | Sarkar ................ A61N 1/36507 |
| 2017/0290550 | A1 * | 10/2017 | Perschbacher ......... A61B 5/076 |
| 2017/0354827 | A1 * | 12/2017 | Zhang .................... A61B 5/363 |
| 2019/0029552 | A1 * | 1/2019 | Perschbacher ..... A61N 1/39622 |
| 2020/0100694 | A1 | 4/2020 | Sarkar et al. |

FOREIGN PATENT DOCUMENTS

| | | | |
|---|---|---|---|
| EP | 1877137 | B1 | 10/2014 |
| EP | 2967402 | B1 | 1/2016 |
| EP | 2364107 | B1 | 9/2016 |
| EP | 1219237 | B1 | 2/2017 |
| EP | 3247453 | B1 | 11/2017 |
| EP | 2895063 | B1 | 1/2019 |
| EP | 3422934 | B1 | 1/2019 |
| EP | 3432774 | B1 | 1/2019 |
| EP | 3566746 | A1 | 5/2019 |
| EP | 3592419 | B1 | 1/2020 |
| EP | 2741662 | B1 | 3/2021 |
| WO | WO03/092810 | A2 | 11/2003 |

* cited by examiner

| Interval Number | R-R Interval (ms) | |
|---|---|---|
| 1 | 734.4 | |
| 2 | 632.8 | |
| 3 | 921.9 | |
| 4 | 773.4 | |
| 5 | 617.2 | |
| 6 | 1039.1 | |
| 7 | 773.4 | |
| 8 | 625.0 | |
| 9 | 1007.8 | |
| 10 | 757.8 | |
| 11 | 632.8 | |
| 12 | 937.5 | |
| 13 | 757.8 | |
| 14 | 632.8 | |
| 15 | 1000.0 | |
| 16 | 765.6 | |
| 17 | 625.0 | |
| 18 | 710.9 | |
| 19 | 273.4 | |
| 20 | 742.2 | |
| 21 | 625.0 | |
| 22 | 937.5 | |
| 23 | 742.2 | |
| 24 | 617.2 | |
| 25 | 789.1 | |
| 26 | 257.8 | ← Minimum |
| 27 | 695.3 | |
| 28 | 625.0 | |
| 29 | 890.6 | |
| 30 | 757.8 | |
| 31 | 617.2 | |
| 32 | 992.2 | |
| 33 | 750.0 | |
| 34 | 625.0 | |
| 35 | 1015.6 | |
| 36 | 765.6 | |
| 37 | 632.8 | |
| 38 | 1085.9 | ← Maximum |
| 39 | 820.3 | |
| 40 | 625.0 | |

*FIG. 15*

METHODS, SYSTEMS AND DEVICES FOR UTILIZING MULTIPLE AF DISCRIMINATORS

PRIORITY CLAIM

Priority is claimed to U.S. Provisional Patent Application No. 63/087,620, filed on Oct. 5, 2020, which is incorporated herein by reference.

FIELD OF TECHNOLOGY

Embodiments described herein relate to techniques for identifying false atrial fibrillation (AF) detections. More specifically, embodiments described herein relate to using various AF discriminators to determine whether to classify AF detections as false positives, i.e., to determine whether to reject AF detections.

RELATED APPLICATIONS

The present application is related to the following commonly assigned U.S. Patent Applications, each of which is incorporated herein by reference:

- U.S. Provisional Patent Application No. 62/967,913 titled METHODS AND SYSTEMS FOR DISTINGUISHING OVER-SENSED R-R INTERVALS FROM TRUE R-R INTERVALS, filed Jan. 30, 2020 (SJUDE-01172US0/13857USIL1).
- U.S. Provisional Patent Application No. 63/033,184 titled METHODS, DEVICES AND SYSTEMS FOR IMPROVING R-WAVE DETECTION AND ARRHYTHMIA DETECTION ACCURACY, filed Jun. 1, 2020 (SJUDE-01172US1/13963USL2).
- U.S. Provisional Patent Application No. 63/034,866 titled METHODS, DEVICES AND SYSTEMS FOR IMPROVING R-WAVE DETECTION AND ARRHYTHMIA DETECTION ACCURACY, filed Jun. 4, 2020 (SJUDE-01172US2/13963USL2).
- U.S. Non-Provisional patent application Ser. No. 17/153,036 titled METHODS AND SYSTEMS FOR DISTINGUISHING OVER-SENSED R-R INTERVALS FROM TRUE R-R INTERVALS, filed Jan. 20, 2021 (SJUDE-01172US3/13857USO1).
- U.S. Non-Provisional patent application Ser. No. 17/153,036 titled METHODS, DEVICES AND SYSTEMS FOR IMPROVING R-WAVE DETECTION AND ARRHTYMIA DETECTION ACCURACY, filed Apr. 6, 2021 (SJUDE-01172US4/13857USO2).
- U.S. Provisional Patent Application No. 63/019,550 titled R-R INTERVAL PATTERN RECOGNITION FOR USE IN ATRIAL FIBRILLATION (AF) DISCRIMINATION, filed May 4, 2020 (SJUDE-01176US0/13962USL1).
- U.S. Non-Provisional patent application Ser. No. 17/226,915 titled R-R INTERVAL PATTERN RECOGNITION FOR USE IN ARRHYTHMIA DISCRIMINATION, filed Apr. 9, 2021 (SJUDE-01176US1/13962USO1).
- U.S. Provisional Patent Application No. 63/033,815, titled METHODS, DEVICES AND SYSTEMS FOR IDENTIFYING FALSE R-R INTERVALS AND FALSE AF DETECTIONS DUE TO R-WAVE UNDERSENSING OR INTERMITTENT AV CONDUCTION BLOCK, filed Jun. 2, 2020 (SJUDE-01177US0/13963USL1).
- U.S. Provisional Patent Application No. 63/033,815, titled METHODS, DEVICES AND SYSTEMS FOR IDENTIFYING FALSE R-R INTERVALS AND FALSE AF DETECTIONS DUE TO R-WAVE UNDERSENSING OR INTERMITTENT AV CONDUCTION BLOCK, filed Jun. 25, 2020 (SJUDE-01177US1/13963USL1).
- U.S. Non-Provisional patent application Ser. No. 17/319,847, titled METHODS, DEVICES AND SYSTEMS FOR IDENTIFYING FALSE R-R INTERVALS AND FALSE ARRHYTHMIA DETECTIONS DUE TO R-WAVE UNDERSENSING OR INTERMITTENT AV CONDUCTION BLOCK, filed May 13, 2021 (SJUDE-01177US2/13963USO1).

BACKGROUND

Various types of implantable medical devices (IMDs) are used to monitor for cardiac arrythmias. Some types of IMDs, such as implantable cardiac pacemakers and implantable cardiac defibrillators (ICDs), are capable of providing appropriate therapy in response to detected cardiac arrythmias. Other types of IMDs, such as insertable cardiac monitors (ICMs), are used for diagnostic purposes. ICMs have been increasingly used to diagnose cardiac arrhythmias, particularly atrial fibrillation (AF).

Atrial Fibrillation (AF) is a very common type of supraventricular tachycardia (SVT) which leads to approximately one fifth of all strokes, and is the leading risk factor for ischemic stroke. However, AF is often asymptomatic and intermittent, which typically results in appropriate diagnosis and/or treatment not occurring in a timely manner. To overcome this, many cardiac devices, such as ICMs, now monitor for AF by obtaining an electrogram (EGM) signal and measuring R-R interval variability based on the EGM signal. For example, an ICM or other IMD can compare measures of R-R interval variability to a variability threshold, to automatically detect AF when the variability threshold is exceeded. Indeed, ICMs predominantly identify AF by quantifying the variability in R-R intervals (i.e., by quantifying the variability in the timing of ventricular contractions).

When an IMD detects an episode of AF, information about the episode may be recorded and a corresponding EGM segment (and/or other information) can be transmitted from the IMD to a patient care network for clinician review. False positive AF detections are highly undesirable, as the burden of sorting through large numbers of clinically irrelevant episodes of AF can be time consuming and costly.

SUMMARY

Certain embodiments of the present technology described herein relate to methods and apparatus (e.g., devices or systems) that use multiple AF discriminators to determine whether to classify an AF detection as a false positive detection. In other words, certain embodiments described herein can be used to reject an AF detection.

A method according to an embodiment of the present technology includes obtaining a signal indicative of cardiac electrical or mechanical activity, identifying one or more characteristics of the signal, and detecting AF based at least in part on a measure of variability of at least one of the one or more characteristics of the signal. The method also includes, in response to detecting AF, analyzing at least one of the one or more characteristics of the signal within a window leading up to the AF detection to thereby determine to what extent the measure of variability was based on inaccurate identifying of at least one of the one or more characteristics of the signal. The method further includes determining whether to classify the AF detection as a false positive detection based on results of the analyzing.

In accordance with certain embodiments, the signal that is obtained comprises an electrogram (EGM) or electrocardiogram (ECG) signal indicative of cardiac electrical activity, and the one or more identified characteristics of the signal comprises R-waves and R-R intervals identified based on the EGM or ECG signal. In certain such embodiments, detecting AF based at least in part on a measure of variability of at least one of the one or more characteristics of the signal comprises detecting the measure of variability based on R-waves and/or the R-R intervals. Further, in response to detecting AF, the R-waves and/or the R-R intervals within the window leading up to the AF detection are analyzed to thereby determine to what extent the measure of variability was based on inaccurate identifying of the R-waves and/or the R-R intervals. Additionally, determining whether to classify the AF detection as a false positive is based on results of the analyzing the R-waves and/or the R-R intervals within the window leading up to the AF detection.

In accordance with certain embodiment, the analyzing and determining include using one or more time-based AF discriminators to analyze one or more temporal characteristics of the EGM or ECG signal within the window leading up to the AF detection to thereby determine whether to classify the AF detection as a false positive based on the one or more temporal characteristics. Additionally, in response to not classifying the AF detection as a false positive using the one or more time-based AF discriminators, one or more morphology-based AF discriminators is/are used to analyze one or more morphological characteristics of the EGM or ECG signal within the window leading up to the AF detection to thereby determine whether to classify the AF detection as a false positive based on the one or more morphological characteristics. In such embodiments, use of a time-based AF discriminator is less computationally intensive than, and consumes less power than, use of a morphology-based AF discriminator.

In accordance with certain embodiments, the one or more time-based AF discriminators, used to analyze one or more temporal characteristics of the EGM or ECG signal, is/are used to determine at least one of the following: whether an extent (e.g., a number or a percent) of false R-R intervals due to R-wave undersensing or intermittent AV conduction block, detected based on R-R intervals within the window leading up to the AF detection, exceeds a corresponding threshold (e.g., a number or a percent threshold); or whether an extent of false R-R intervals due to at least one of T-wave or P-wave oversensing, detected based on R-R intervals within the window leading up to the AF detection, exceeds a corresponding threshold (e.g., a number or a percent threshold). In certain embodiments, in response to the number of false R-R intervals due to R-wave undersensing or intermittent AV conduction block not exceeding the corresponding threshold, and the number of false R-R intervals due to at least one of T-wave or P-wave oversensing not exceeding the corresponding threshold, the method further comprises determining whether a dominant repeated R-R interval pattern, detected based on R-R intervals within the window leading up to the AF detection, exceeds a corresponding threshold.

In accordance with certain embodiments, the one or more morphology-based AF discriminators, used to analyze one or more morphological characteristics of the EGM or ECG signal, is/are used to determine: whether an extent (e.g., a number or a percent) of over-sensed P-waves, detected based on magnitudes of portions of the EGM or ECG signal within the window leading up to the AF detection, exceeds a corresponding threshold (e.g., a number or a percent threshold). In certain embodiments, in response to the number of over-sensed P-waves not exceeding the corresponding threshold, the method further comprises determining whether an extent of actual P-waves, detected based on comparisons between one or more P-wave templates and portions of the EGM or ECG signal within the window leading up to the AF detection, exceeds a corresponding threshold (e.g., a number or a percent threshold).

In accordance with certain embodiments, a plurality of the time-based AF discriminators and a plurality of the morphology-based AF discriminators are used over time when determining whether to classify each of a plurality of AF detections as a false positive. In certain such embodiments, the method also includes tracking how often individual ones of the time-based and the morphology-based AF discriminators are used to classify AF detections as false positives, and selectively disabling one or more of the time-based or the morphology-based AF discriminators based on how often individual ones of the time-based and the morphology-based AF discriminators are used to classify AF detections as false positives.

In accordance with certain embodiments, where a plurality of the time-based AF discriminators and a plurality of the morphology-based AF discriminators are used over time when determining whether to classify each of a plurality of AF detections as a false positive, the method further comprises: for each condition of a plurality of different conditions, tracking how often individual ones of the time-based and the morphology-based AF discriminators are used to classify AF detections as false positives during the condition. The method also includes, for a condition, selectively disabling one or more of the time-based or the morphology-based AF discriminators based on how often individual ones of the time-based and the morphology-based AF discriminators are used to classify AF detections as false positives during the condition. The plurality of different conditions can include, for example, a plurality of different patient activity levels, a plurality of different heart rate ranges, a plurality of different times of day, or a plurality of different respiration patterns.

In accordance with certain embodiments, one of the methods summarized above is performed by an implantable medical device (IMD), and the method further comprises at least one of the following: the IMD preventing transmitting, to an external device that is communicatively coupled to a patient care network, of data corresponding to an AF detection that is detected by the IMD but is thereafter determined by the IMD as being a false positive detection; the IMD allowing overwriting of stored data corresponding to the AF detection that was detected by the IMD but is thereafter determined by the IMD as being a false positive detection; or the IMD not storing in memory data corresponding to the AF detection that is detected by the IMD but is thereafter determined by the IMD as being a false positive detection.

In accordance with certain embodiments, an AF detection is classified as a true positive detection in response to none of the time-based and the morphology-based AF discriminators being used to classify the AF detection as a false positive.

In accordance with certain embodiments, in response to none of the time-based and the morphology-based AF discriminators being used to classify the AF detection as a false positive, the method includes the IMD storing, in memory of the IMD, data corresponding to the AF detection. Alternatively, or additionally, the IMD transmits, to an external device that is communicatively coupled to a patient care network, data corresponding to the AF detection.

Certain embodiments of the present technology are directed to an apparatus (e.g., a system or device) that comprises at least one electrode or sensor configured to obtain a signal indicative cardiac electrical or mechanical activity of a patient's heart. The apparatus also comprises at least one processor configured to identify one or more characteristics of the signal, and detect AF based at least in part on a measure of variability of at least one of the one or more characteristics of the signal. Additionally, the at least one processor is configured to analyze at least one of the one or more characteristics of the signal within a window leading up to the AF detection to thereby determine to what extent the measure of variability was based on inaccurate identifying of at least one of the one or more characteristics of the signal. Further, the at least one processor is configured to determine whether to classify the AF detection as a false positive detection based on the extent the measure of variability was based on inaccurate identifying of at least one of the one or more characteristics of the signal.

In accordance with certain embodiments, where the signal comprises an EGM or ECG signal indicative of cardiac electrical activity of the patient's heart, the at least one processor is configured to identify R-waves and R-R intervals based on the EGM or ECG signal, and detect the AF based at least in part on a measure of variability of the R-R intervals. Additionally, the at least one processor is configured to analyze the R-waves and/or the R-R intervals within the window leading up to the AF detection to thereby determine to what extent the measure of variability was based on inaccurate identification of the R-waves and/or the R-R intervals, and determine whether to classify the AF detection as a false positive based on the extent the measure of variability was based on inaccurate identification of the R-waves and/or the R-R intervals.

In accordance with certain embodiments, the at least one processor is configured to use one or more time-based AF discriminators to analyze one or more temporal characteristics of the EGM or ECG signal within the window leading up to the AF detection to thereby determine whether to classify the AF detection as a false positive based on the one or more temporal characteristics. Further, in response to the AF detection not being classified as a false positive using the one or more time-based AF discriminators, the at least one processor is configured to use one or more morphology-based AF discriminators to analyze one or more morphological characteristics of the EGM or ECG signal within the window leading up to the AF detection to thereby determine whether to classify the AF detection as a false positive based on the one or more morphological characteristics. In certain such embodiments, use of a time-based AF discriminator is less computationally intensive than, and consumes less power than, use of a morphology-based AF discriminator.

In accordance with certain embodiments of the present technology, the one or more time-based AF discriminators, used to analyze one or more temporal characteristics of the EGM or ECG signal, is/are used to determine at least one of the following: whether an extent of false R-R intervals due to R-wave undersensing or intermittent AV conduction block, detected based on R-R intervals within the window leading up to the AF detection, exceeds a corresponding threshold; whether an extent of false R-R intervals due to at least one of T-wave or P-wave oversensing, detected based on R-R intervals within the window leading up to the AF detection, exceeds a corresponding threshold; or whether a dominant repeated R-R interval pattern, detected based on R-R intervals within the window leading up to the AF detection, exceeds a corresponding threshold.

In accordance with certain embodiments of the present technology, the one or more morphology-based AF discriminators, used to analyze one or more morphological features of the EGM or ECG signal, is/are used to determine at least one of the following: whether an extent of over-sensed P-waves, detected based on magnitudes of portions of the EGM or ECG signal within the window leading up to the AF detection, exceeds a corresponding threshold; or whether an extent of actual P-waves, detected based on comparisons between one or more P-wave templates and portions of the EGM or ECG signal within the window leading up to the AF detection, exceeds a corresponding threshold.

In accordance with certain embodiments of the present technology, a method for use with an IMD comprises: sensing an ECG or ECG indicative of cardiac electrical activity; detecting R-waves within the EGM or ECG signal, determining R-R intervals based on the R-waves, and detecting AF based on the R-R intervals. The method also includes, in response to detecting AF, using one or more time-based AF discriminators to analyze one or more temporal features of the EGM or ECG signal within a window leading up to the AF detection to thereby determine whether to classify the AF detection as a false positive based on the one or more temporal features. The method further includes, in response to not classifying the AF detection as a false positive using the one or more time-based AF discriminators, using one or more morphology-based AF discriminators to analyze one or more morphological features of the EGM or ECG signal within the window leading up to the AF detection to thereby determine whether to classify the AF detection as a false positive based on the one or more morphological features. In certain such embodiments, use of a time-based AF discriminator is less computationally intensive than, and consumes less power than, use of a morphology-based AF discriminator.

In accordance with certain embodiments of the present technology, an apparatus comprises at least one electrode configured to sense an EGM or ECG signal indicative of cardiac electrical activity. The apparatus also comprises at least one processor configured to detect R-waves within the EGM or ECG signal, determine R-R intervals based on the R-waves, and detect AF based on the R-R- intervals. The at least one processor is also configured to use one or more time-based AF discriminators to analyze one or more temporal features of the EGM or ECG signal within a window leading up to the AF detection to thereby determine whether to classify the AF detection as a false positive based on the one or more temporal features. Additionally, in response to the AF detection not being classified as a false positive using the one or more time-based AF discriminators, the at least one processor is configured to use one or more morphology-based AF discriminators to analyze one or more morphological features of the EGM or ECG signal within the window leading up to the AF detection to thereby determine whether to classify the AF detection as a false positive based on the one or more morphological features.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

FIG. 15 shows a table including a list of forty R-R intervals within the thirty-second window shown in FIG. 14.

DETAILED DESCRIPTION

Figure 1:
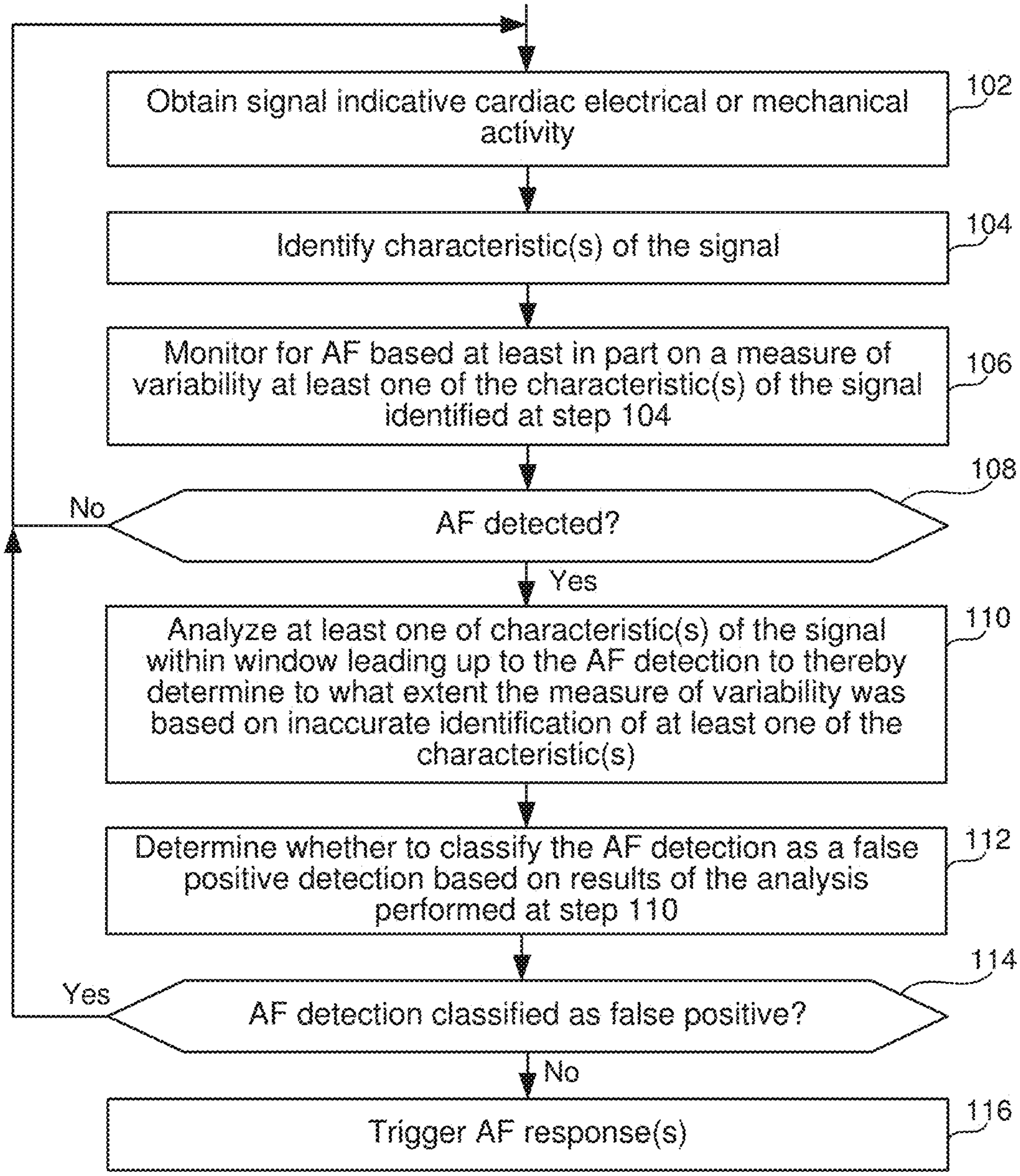
FIG. 1 is a high level flow diagram used to describe certain embodiments of the present technology that can be used determine whether to classify an AF detection as a false positive, i.e., to reject the AF detection.

It is well known that each cardiac cycle represented within an EGM or ECG typically includes a P-wave, followed by a QRS complex, followed by a T-wave, with the QRS complex including Q-, R-, and S-waves. The P-wave is caused by depolarization of the atria. This is followed by atrial contraction, which is indicated by a slight rise in atrial pressure contributing to further filling of the ventricle. Following atrial contraction is ventricular depolarization, as indicated by the QRS complex, with ventricular depolarization initiating contraction of the ventricles resulting in a rise in ventricular pressure until it exceeds the pulmonary and aortic diastolic pressures to result in forward flow as the blood is ejected from the ventricles. Ventricular repolarization occurs thereafter, as indicated by the T-wave and this is associated with the onset of ventricular relaxation in which forward flow stops, the pressure in the ventricle falls below that in the atria at which time the mitral and tricuspid valves open to begin to passively fill the ventricle during diastole. The terms EGM, EGM signal, and EGM waveform are used interchangeably herein. Similarly, the terms ECG, ECG signal, and ECG waveform are used interchangeably herein. Both ECG and EGM signals are signals indicative of cardiac electrical activity of a patient's heart.

The R-wave is typically the largest wave in the QRS complex, and it often identified by comparing samples of an EGM or ECG to an R-wave threshold. Various measurements can be obtained based on the EGM or ECG waveform, including measurements of R-R intervals, where an R-R interval is the duration between a pair of consecutive R-waves. R-waves and R-R intervals are examples of characteristics of an EGM or ECG signal, or more generally, of a signal indicative of cardiac electrical activity of a patient's heart.

IMDs often use algorithms to detect AF, wherein such algorithms are often based on the detection of R-waves and R-R intervals, or more generally, based on one or more characteristics of a signal indicative of electrical activity of a patient's heart. For an example, certain such algorithms are trained with AF and non-AF data. Then, after the algorithm has been trained, the algorithm is used at each beat to analyze a prior predetermine number of beats (e.g., the prior 64 beats) and based thereon classify a patient's cardiac rhythm as AF or non-AF. In a specific implementation, an AF detection algorithm has three components including: a first probability component, which is a Markov-Chain Based Probability ($P_{MC}$); a second probability component, which is a Variance Probability ($P_{VAR}$); and a Sudden Onset Score component. The first probability component, i.e., the Markov-Chain Based Probability ($P_{MC}$), quantifies the irregularity of R-R intervals. The second probability component, i.e., the Variance Probability ($P_{VAR}$), is used to differentiate random versus patterned changes in R-R interval (e.g., bigeminy). An AF detection that is based on the Markov-Chain Based Probability ($P_{MC}$) and the Variance Probability ($P_{VAR}$) can be more accurately referred to as a potential AF detection, or a detection of a potential AF episode, since it is possible that what appears to be an AF detection is a false AF detection, i.e., a false positive AF detection. Additional details of using the aforementioned Markov-Chain Based Probability ($P_{MC}$), the Variance Probability ($P_{VAR}$), and the Sudden Onset Score, are described in U.S. Pat. No. 8,121,675 to Shaquer et al., titled "Device and method for detecting atrial fibrillation," which issued Feb. 21, 2012, which is incorporated herein by reference. It would also be possible to detect AF based on just R-R variability, or using other techniques.

Instead of, or in addition to, monitoring for AF based on one or more characteristics of a signal indicative of cardiac electrical activity, such as an EGM or ECG, it is also possible to monitor for AF based on one or more characteristics of a signal indicative of cardiac mechanical activity. Examples of signals that are indicative of cardiac mechanical activity, based upon which AF can be detected, include a cardiogenic impedance signal, a photoplethysmography signal, an impedance plethysmography signal, and a heart sounds signal, but is not limited thereto. AF can be detected based on such a signal, e.g., by determining peak-to-peak intervals, determining the variability of the peak-to-peak intervals, and comparing the variability to a threshold. Alternative and/or additional techniques for monitoring for AF based on one or more characteristics of a signal indicative of cardiac mechanical activity can be used.

When monitoring for AF based on one or more characteristics (e.g., R-waves, R-R intervals, or peak-to-peak intervals) of a signal indicative of cardiac electrical or mechanical activity, it is possible that certain characteristics, such as R-waves and/or R-R intervals, are inaccurately identified, which can lead to false positive AF detections. In accordance with certain embodiments of the present technology, initially described below with reference to FIG. 1, at least one characteristic (e.g., R-R intervals) of the signal indicative of cardiac electrical or mechanical activity, based upon which AF is detected, is/are analyzed within a window leading up to the AF detection to thereby determine to what extent the AF detection was based on inaccurate identifying the at least one characteristic (e.g., R-R intervals), and then based on such analysis, there is a determination of whether to classify the AF detection as a false positive detection. For a specific example, if at least 10 percent of the R-R intervals, upon which an AF detection was based, are determined to be false R-R intervals, then the AF detection may be classified as a false AF detection. Alternative and additional details of such embodiments will be appreciated from the below discussion, which begins with a description of the flow diagram in FIG. 1.

Referring to FIG. 1, step 102 involves obtaining a signal indicative of cardiac electrical or mechanical activity of a patient's heart. Where the signal is indicative of cardiac electrical activity, the signal can be an EGM or ECG signal, as note above. Where the signal is indicative of cardiac mechanical activity, the signal can be a cardiogenic impedance signal, a photoplethysmography signal, an impedance plethysmography signal, or a heart sounds signal, as noted above, but is not limited thereto. For much of the remaining discussion, it is assumed that the signal obtained at step 102 is an EGM signal, but as can be appreciated from the above discussion, that need not be the case.

Step 104 involves identifying one or more characteristics of the signal obtained at step 102. Where the signal obtained at step 102 is an EGM signal (or an ECG signal), characteristics of the EGM signal (or ECG signal) that are identified at step 104 can include R-waves and R-R intervals, but are not limited thereto.

Step 106 involves monitoring for AF based at least in part on a measure of variability of at least one of the one or more characteristics of the signal obtained at step 102, which characteristics were identified at step 104. For example, at step 106 AF may be monitored for based on a measure of variability of R-R intervals, but is not limited thereto. At step 108 there is a determination of whether AF was detected. If the answer to the determination at step 108 is No, then flow returns to step 102. If the answer to the determination at step 108 is Yes, then flow goes to step 110. While steps 106 and 108 are shown as two separate steps in FIG. 1, it is also possible to combine those steps into a single step.

Step 110 involves analyzing at least one of the characteristic(s) (e.g., R-wave and/or R-R intervals) of the signal (e.g., the EGM) within a window leading up to the AF detection to thereby determine to what extent the measure of variability was based on inaccurate identifying of at least one of the characteristic(s) (e.g., R-wave and/or R-R intervals). Example details of how a characteristic, such as R-R intervals, can be analyzed to determine to what extent they are inaccurate, are described further below.

Step 112 involves determining whether to classify the AF detection based on results of the analyzing performed at step 110. For example, assuming AF was detected at steps 106 and 108 based on a measure of variability of R-R intervals, at step 112 the AF detection may be classified as a false positive if at least a specified threshold of the R-R intervals within the window (e.g., a 30 second window) leading up to the AF detection are determined to be inaccurate (e.g., false R-R intervals). The specified threshold can be a percent, e.g., 10 percent, or some other specified percent. Alternatively the specified threshold can be a number, e.g., 5, or some other specified number. At step 114 there is a determination of whether the AF detection was classified as a false positive. If the answer to the determination at step 114 is Yes, then flow returns to step 102. If the answer to the determination at step 114 is No, then flow goes to step 116. While steps 112 and 114 are shown as two separate steps in FIG. 1, it is also possible to combine those steps into a single step.

At step 116 one or more AF responses is/are triggered, since the AF detection was not classified as a false positive.

For example, if the method described with reference to FIG. 1 is performed by an IMD that is configured to transmit, to an external device that is communicatively coupled to a patient care network, data corresponding to an AF episode, then the response performed at step 116 can be transmitting of data corresponding to the AF episode that was detected. However, if the AF detection was classified as being a false positive, then step 116 is skipped, and thus, the IMD is prevented from transmitting (to the external device) data corresponding to the AF episode that was detected, but was thereafter determined by the IMD as being a false positive detection.

An additional or alternative response to an AF detection, which is performed by an IMD, is storing (in memory of the IMD) data corresponding to an AF episode that is detected by the IMD. Such storing of data corresponding to an AF episode may be prevented if the AF episode that is detected is thereafter determined by the IMD as being a false positive detection. Alternatively, if data corresponding to an AF episode is already stored in memory, but thereafter the detection of the AF episode is classified as being a false positive, then the IMD can allow overwriting in the memory of data corresponding to an AF episode that was detected by the IMD but was thereafter determined by the IMD as being a false positive detection.

Embodiments of the present technology described herein can be used with various types of IMDs, including, but not limited to, an insertable cardiac monitor (ICM), a cardiac pacemaker to which one or more leads is/are attached, a leadless cardiac pacemaker (LCP), or an implantable cardioverter defibrillator (ICD). Such an ICD can be a transvascular ICD, or a nonvascular ICD, wherein the nonvascular ICD can be a subcutaneous (SubQ) ICD. Where embodiments of the present technology are implemented by an ICM, such embodiments can be used, e.g., to reduce the number of false positive AF detections that are transmitted from the ICM to a patient care network for clinician review. This is beneficially because false positive AF detections are highly undesirable, as the burden of sorting through large numbers of clinically irrelevant episodes of AF can be time consuming and costly. Where embodiments of the present technology are used by an ICD, or by an IMD in communication with an ICD, such embodiments can reduce how often defibrillation shocks are delivered in response to false positive AF detections. This is beneficial because defibrillation shocks are typically painful, and delivering such shocks in response to false positive AF detections subjects the patient to unnecessary shocks and may prematurely deplete the energy stored in a battery.

In accordance with certain embodiments of the present technology, the analyzing and the determining that are performed at step 110 and 112 can involve using one or more time-based AF discriminators to analyze one or more temporal characteristics of an EGM or ECG within the window leading up to the AF detection to thereby determine whether to classify the AF detection as a false positive based on the one or more temporal characteristics. Time-based AF discriminators can also be referred to temporal-based AF discriminators. In certain such embodiments, in response to not classifying the AF detection as a false positive using the one or more time-based AF discriminators, one or more morphology-based AF discriminators may be used to analyze one or more morphological characteristics of the EGM or ECG within the window leading up to the AF detection to thereby determine whether to classify the AF detection as a false positive based on the one or more morphological characteristics. Morphology-based AF discriminators can also be referred to as morphological-based AF discriminators. Examples of time-based AF discriminators and morphology-based AF discriminators are discussed below with reference to FIGS. 4-21. Use of a time-based AF discriminator is less computationally intensive than, and consumes less power than, use of a morphology-based AF discriminator. Accordingly, it is more computationally and energy efficient to use one or more time-based AF discriminators, to determine whether to classify an AF detection as a false positive detection, prior to using one or more morphology-based AF discriminators. In other words, using time-based AF discriminators prior to morphology-based discriminators can conserve processing resources and can extend battery life, and thus, device longevity.

When using the various AF discriminators, to determine whether or not to classify an AF detection as a false positive, the AF discriminators need not all use the entirety of the window leading up to the AF detection. Rather, some of the AF discriminators may just use one or more portions of the window. Further, it is noted that classifying an AF detection as a false positive, as the phrase is used herein, is the same as rejecting or overturning an AF detection. Further, classifying an AF detection as a true positive is the same as confirming an AF detection. In certain embodiments, an AF detection is classified as a true positive detection in response to none of the time-based and the morphology-based AF discriminators being used to classify the AF detection as a false positive.

In accordance with certain embodiments, the time-based AF discriminator(s), which is/are used to analyze one or more temporal characteristics of the EGM or ECG, may be used to determine whether an extent of false R-R intervals due to R-wave undersensing or intermittent AV conduction block, detected based on R-R intervals within the window leading up to the AF detection, exceeds a corresponding threshold. Additionally details of how to make such a determination are described below with reference to FIGS. 4-9. Alternatively, or additionally, the time-based AF discriminator(s) may be used to determine whether an extent of false R-R intervals due to at least one of T-wave or P-wave oversensing, detected based on R-R intervals within the window leading up to the AF detection, exceeds a corresponding threshold. Additionally details of how to make such a determination are described below with reference to FIGS. 10-13. It is noted that the term R-R interval, unless specified otherwise, can refer to a true R-R interval or a false R-R interval, wherein an over-sensed R-R interval is an example of a false R-R interval. More specifically, example types of intervals that may be mistakenly identified as an R-R interval, and thus are examples of false R-R intervals, include, but are not limited to, P-R intervals, R-T intervals, P-T intervals, and T-P intervals. False R-R intervals that are due to T-wave oversensing include, e.g., R-T intervals, P-T intervals, and T-P intervals.

In accordance with certain embodiments of the present technology, a plurality of different time-based AF discriminators and a plurality of different morphology-based AF discriminators can be used over time to determine whether to classify each of a plurality of AF detections as a false positive. In certain such embodiments, how often individual ones of the time-based and the morphology-based AF discriminators are used to classify AF detections as false positives can be tracked. Then based on such tracked information, one or more of the time-based or the morphology-based AF discriminators can be selectively disabled based on how often individual ones of the time-based and the morphology-based AF discriminators are used to classify AF detections as false positives. For an example, if a specific time-based AF discriminator is used to analyze fifty different AF detections, but the specific time-based AF discriminator is never used to classify an AF detection as a false positive, yet twenty percent (i.e., ten of the fifty) of the AF detections are classified as being false positives (using other AF discriminators), then it can be concluded that the specific time-based AF discriminator is not very effective for the specific patient, and thus can be disabled to conserve processing resources and extend battery life, and thus, device longevity.

In accordance with certain embodiments, a plurality of the time-based AF discriminators and a plurality of the morphology-based AF discriminators are used over time when determining whether to classify each of a plurality of AF detections as a false positive. In certain such embodiments, for each condition of a plurality of different conditions (e.g., a plurality of different patient activity levels, different heart rate ranges, different times of day, and/or different respiration patterns) that is/are detected by an IMD, the IMD can track how often individual ones of the time-based and the morphology-based AF discriminators are used to classify AF detections as false positives during the condition. The IMD, or more specifically, a processor thereof, can for each of the conditions, selectively disable one or more of the time-based or the morphology-based AF discriminators based on how often individual ones of the time-based and the morphology-based AF discriminators are used to classify AF detections as false positives during the said condition. For an example, an IMD implanted in a patient may determine that a specific AF discriminator is never or rarely used to classify AF detections as false positives when the patient is active, but is often used classify AF detections as false positives when the patient is at rest. Based on such tracked information, the IMD can selectively disable the specific AF discriminator when the patient is determined to be active (e.g., based on information obtained from an accelerometer or other sensor), and can enable the specific AF discriminator when the patient is determined to be at rest.

Figure 2:
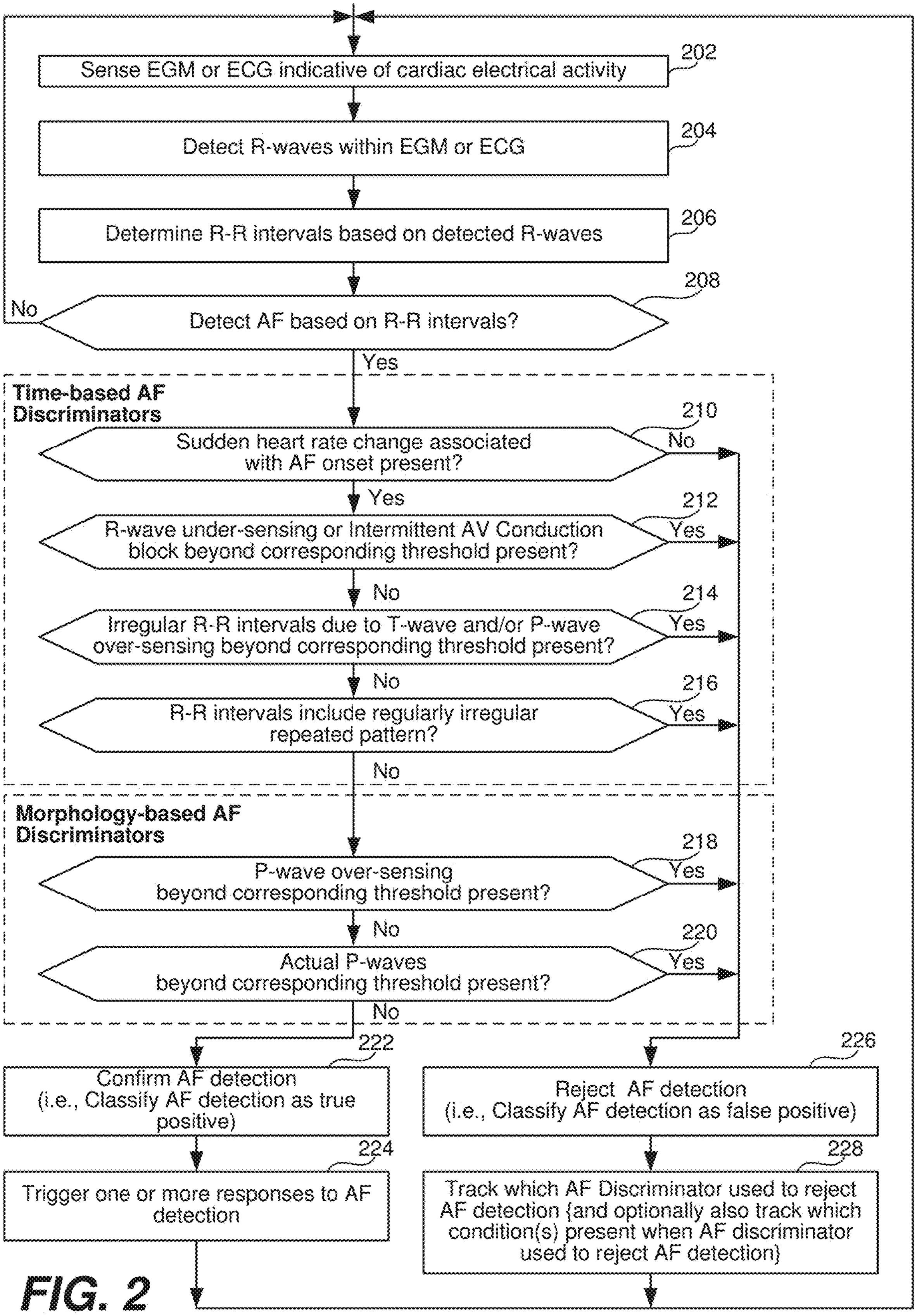
FIG. 2 is a high level flow diagram used to describe certain embodiments of the present technology that, after an AF detection, use one or more time-based AF discriminators prior to using one or more morphology-based AF discriminators to determine whether to reject the AF detection.

The high level flow diagram of FIG. 2 will now be used to explain how time-based AF discriminators may be used before morphology-based AF discriminators, in accordance with certain embodiments of the present technology. As noted above, use of a time-based AF discriminator is less computationally intensive than, and consumes less power than, use of a morphology-based AF discriminator. Accordingly, it is more computationally and energy efficient to use one or more time-based AF discriminators, to determine whether to classify an AF detection as a false positive detection, prior to using one or more morphology-based AF discriminators, as was also noted above. In other words, using time-based AF discriminators prior to morphology-based discriminators can conserve processing resources and can extend battery life, and thus, device longevity.

Referring to FIG. 2, step 202 involves sensing an EGM or ECG, or more generally, a signal indicative of cardiac electrical activity. Such sensing can be performed using one or more electrodes on a lead and/or a housing of an IMD, as is known in the art. Step 204 involves detecting R-waves within the sensed EGM or ECG. R-waves can be detected by comparing the EGM or ECG to an R-wave threshold and/or by comparing the morphology of the EGM or ECG to an R-wave morphological template, as is known in the art, but is not limited thereto. Step 206 involves determining R-R intervals based on the detected R-waves, where an R-R interval is the duration between a pair of consecutive R-waves, as is known in the art.

Step 208 involves determining whether AF is detected based on the R-R intervals. Any one or more known or future developed techniques for detecting AF based on R-R intervals can be used at step 208. For an example, at step 208 a measure of R-R interval variability can be determined and compared to a variability threshold, and AF can be detected when the variability threshold is exceeded. Various other techniques for detecting AF based on R-waves and/or R-R intervals can additionally or alternatively be used. For example, as noted above, three components can be determined, including: a Markov-Chain Based Probability (PMC), a Variance Probability (PVAR), and a Sudden Onset Score component, and can be used to detect AF, as described in U.S. Pat. No. 8,121,675 to Shaquer et al., which was incorporated herein by reference above. It would also be possible to detect AF based on just R-R variability, or using other techniques. If the answer to the determination at step 208 is No, the flow returns to step 202. If the answer to the determination at step 208 is Yes, then one or more AF discriminators is/are used to determine whether to classify the AF detection as a false positive.

Still referring to FIG. 2, steps 210-216 involve using various different time-based AF discriminators to determine whether to classify the AF detection (aka the detected AF episode) as a false positive detection. While a specific order of the time-based AF discriminators is shown in FIG. 2, it is within the scope of the embodiments described herein to change the order and/or to use less than all of the time-based AF discriminators shown in FIG. 2. Each of steps 210-216 can be performed based on a window (e.g., a 30 second window) leading up to the AF detection, wherein R-R intervals within the window were used to detect AF at step 208.

At step 210 there is a determination of whether there is a sudden heart rate change associated with AF onset present, since a sudden heart rate change should have occurred if AF was actually detected. If the answer to the determination at step 210 is No, then flow goes to step 226 and the AF detection is rejected, i.e., the AF detection is classified as a false positive detection. Following step 226, step 228 is performed. Step 228 involves tracking which AF discriminator was used to reject the AF detection. Step 228 can also optionally involve tracking which condition(s) was/were present when the AF discriminator was used to reject the AF detection. Examples of the conditions that may be tracked include, but are not limited to, the activity level of the patient, the heart rate of the patient, the time of day, and/or the respiration pattern of the patient. If the answer to the determination at step 210 is Yes, then flow goes to step 212.

At step 212 there is a determination of whether R-wave under-sensing or intermittent AV conduction block beyond a corresponding threshold occurred within the window leading up to the AF detection. Example details of how step 212 can be performed, in accordance with certain embodiments of the present technology, are described below with reference to FIGS. 4-9. If the answer to the determination at step 212 is Yes, then flow goes to step 226, and then to step 228. If the answer to the determination at step 212 is No, then flow goes to step 214.

At step 214 there is a determination of whether irregular R-R intervals, due to T-wave and/or P-wave oversensing, beyond a corresponding threshold were present within the window leading up to the AF detection. Example details of how step 214 can be performed, in accordance with certain embodiments of the present technology, are described below with reference to FIGS. 10-13. If the answer to the determination at step 214 is Yes, then flow goes to step 226, and then to step 228. If the answer to the determination at step 214 is No, then flow goes to step 216.

At step 216 there is a determination of whether the R-R intervals within the window leading up to the AF detection include a regularly irregular pattern. Example details of how step 216 can be performed, in accordance with certain embodiments of the present technology, are described below with reference to FIGS. 14-17. If the answer to the determination at step 216 is Yes, then flow goes to step 226, and then to step 228. If the answer to the determination at step 216 is No, then flow goes to step 218, or more generally, then one or more morphology-based AF discriminator(s) is/are used to determine whether the AF detection should be classified as a false positive.

Still referring to FIG. 2, steps 218-220 involve using various different morphology-based AF discriminators to determine whether to classify the AF detection (aka the detected AF episode) as a false positive detection. While a specific order of the morphology-based AF discriminators is shown in FIG. 2, it is within the scope of the embodiments described herein to change the order and/or to use less than all of the morphology-based AF discriminators shown in FIG. 2. Each of steps 218-220 can be performed based on a window (e.g., a 30 second window) leading up to the AF detection, wherein R-R intervals within the window were used to detect AF at step 208.

At step 218 there is a determination of whether P-wave oversensing beyond a corresponding threshold occurred within the window leading up to the AF detection. Example details of how step 218 can be performed, in accordance with certain embodiments of the present technology, are described below with reference to FIGS. 18-21. If the answer to the determination at step 218 is Yes, then flow goes to step 226, and then to step 228. If the answer to the determination at step 218 is No, then flow goes to step 220.

At step 220 there is a determination of whether actual P-waves beyond a corresponding threshold are present within the window leading up to the AF detection. Step 220 is performed because P-waves should not be present during an episode of AF. Example details of how step 220 can be performed by analyzing the morphology of an ECG or EGM, are described further below. If the answer to the determination at step 220 is Yes, then flow goes to step 226, and then to step 228. If the answer to the determination at step 220 is No, then flow goes to step 222.

At step 222 the AF detection is confirmed (i.e., classified as a true positive), and at step 224 one or more responses are triggered in response to the AF detection, or more specifically, confirmation thereof. Example responses to an AF detection were described above, and thus, need not be repeated.

In embodiments described with reference to FIG. 2, once AF is detected, regardless of the specific technique that was used to detect AF, one or more time-based AF discriminators is/are used to determine whether to classify the AF detection as a false positive based on the one or more temporal features of an EGM or ECG. Thereafter, if none of the time-based AF discriminators was used to classify the AF detection as a false positive, then one or more morphology-based AF discriminators is/are used to analyze one or more morphological features of the EGM or ECG within the window leading up to the AF detection to thereby determine whether to classify the AF detection as a false positive based on the one or more morphological features. In other words, in response to the AF detection not being classified as a false positive using the one or more time-based AF discriminators, then one or more morphology-based AF discriminators is/are used to thereby determine whether to classify the AF detection as a false positive based on the one or more morphological features of the EGM or ECG within the window leading up to the AF detection. When using the various AF discriminators, they need not all use the entirety of the window leading up to the AF detection. Rather, some of the AF discriminators may just use one or more portions of the window.

Each of the time-based AF discriminators is less computationally intensive than, and consumes less power than, each morphology-based AF discriminators. Further, because the time-based AF discriminators are less computationally intensive than the morphology-based AF discriminators, each of the time-based AF discriminators can be executed more quickly than each of the morphology-based AF discriminators. Accordingly, utilizing the time-based AF discriminator(s) prior to utilizing the morphology-based AF discriminator(s) will have the overall effect of optimizing computational resources and battery longevity, and thus, IMD longevity.

Figure 3:
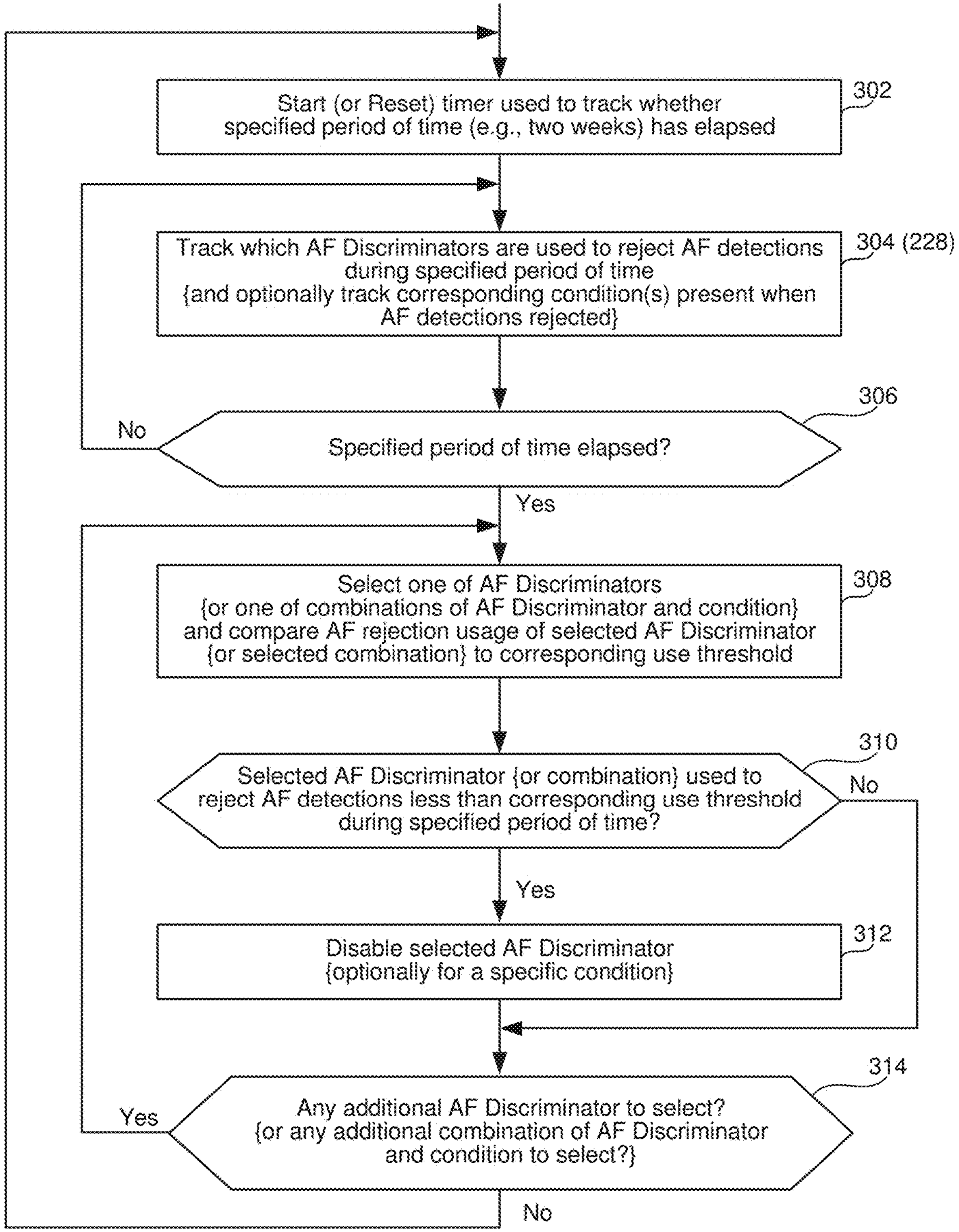
FIG. 3 is a high level flow diagram that is used to summarize certain embodiments of the present technology that are used to selectively disable one or more AF discriminators that are used to determine whether to reject AF detections.

The high level flow diagram of FIG. 3 will now be used to describe specific embodiments of the present technology that can be used to selectively disable certain AF discriminators, so as to not waste limited processing and energy resources implementing one or more AF discriminators that are not used, or are minimally used, to reject AF detections. Referring to FIG. 3, step 302 involves starting (or resetting) a timer that is used to track whether as specified period of time (e.g., two weeks) has elapsed.

Still referring to FIG. 3, step 304 involves tracking which AF discriminators are used to reject AF detections during the specific period of time (e.g., two weeks). The tracking that is performed at step 304 can be achieved at various instance of step 228 that were described above in the discussion of FIG. 2. Additionally, step 304 can also include tracking corresponding condition(s) that were present when the AF detection was rejected, or more specifically, that coincided with window leading up and analyzed to make the AF detection. As mentioned above, examples of the conditions that may be tracked include, but are not limited to, the activity level of the patient, the heart rate of the patient, the time of day, and/or the respiration pattern of the patient.

At step 306 there is a determination of whether the specified period has elapsed. If the answer to the determination at step 306 is No, then flow returns to step 304. If the answer to the determination at step 306 is Yes, then flow goes to step 308. At step 308 one of the AF discriminators is selected, and there is comparison between how many time the selected AF discriminator was used to reject an AF detection and a corresponding threshold. Alternatively, if different conditions that coincide with the AF detection and rejection are also tracked, then one of the combinations of AF discriminators and conditions is selected at step 308, and there is comparison between how many time the selected AF discriminator was used to reject an AF detection (while that condition existed) and a corresponding threshold. An example combination selected at step 308 is the combination of the AF discriminator used at step 212 (i.e., R-wave understanding or intermittent AV conduction block resulting in an AF rejection) and the patient being at rest. Another example combination that can be selected at an instance of step 308 is the combination of the AF discriminator used at step 214 (i.e., irregular R-R intervals due to T-wave and/or P-wave over-sensing resulting in an AF rejection) and the patient having a heart rate within first specified range. Still another example of a combination that can be selected at an instance of step 308 is the combination of the AF discriminator used at step 218 (i.e., P-wave overseeing resulting in an AF rejection), the time of day being in the early afternoon, and the patient being active. These are just a few examples which are not meant to be all encompassing and inclusive.

Still referring to FIG. 3, at step 310 that is a determination of whether the number (or percentage) of time the AF discriminator (or the combination of AF discriminator and characteristic) selected at step 308 was used to reject AF, during the period of time, is less than a specified threshold. If the answer to the determination at step 310 is No, the flow skips to step 314. If the answer to the determination at step 310 is Yes, the flow goes to step 312 and the AF discriminator (or the combination of AF discriminator and characteristic) is disabled. After step 312 flow goes to step 314.

At step 314 there is a determination of whether there is any additional AF discriminator (or any additional combination of AF discriminator and characteristic) to select. If the answer to the determination at step 314 is Yes, the flow returns to step 308. If the answer to the determination at step 314 is No, the flow returns to step 302. Using the embodiments summarized with reference to the high level flow diagram of FIG. 3, certain AF discriminators that are not used, or a rarely used, to reject AF detections are disabled, so that only those AF discriminators that are effectively used to reject AF detections are used. This should have the effect of reducing overall processing and make determinations of whether to reject AF detections quicker.

Periodically, e.g., every three months, all of the AF discriminators that are available, even if previously disabled, can be enabled, and the process described with reference to FIG. 3 can be repeated. This may be beneficial because which AF discriminators are the most useful may change over time as the patient's physiology and underling cardiac health changes.

Referring briefly back to FIG. 2, which was described above, various different time-based AF discriminators can be used to determine whether to classify an AF detection as a false positive, i.e., to reject an AF detection. Additionally, various morphological AF discriminators can also be used to determine whether to classify an AF detection as a false positive, i.e., to reject an AF detection. Example details of these various AF discriminators, introduced in FIG. 2, are provided below.

Sudden Onset

When AF occurs, there is a sudden change in a patient's heart rate that occurs, and more specifically, a sudden onset of irregularity of ventricular events. Accordingly, one time-based AF discriminator that can used (e.g., at step 210 in FIG. 2) to determine whether to classify an AF detection as a false positive analyzes whether a sudden onset criterion is satisfied. Such a sudden onset AF discriminator can scan beats within a window leading up to the AF detection to characterize the change of heart rate. The beats scanned may include all beats within the window or a subset of beats. An AF discriminator algorithm can be used to determine whether there was a "significant change" in heart rate being associated with potential AF onset. If the change of heart rate assessed by the sudden onset discriminator is determined to be "sudden", then the AF detection is not rejected (i.e., not classified as a false positive). Otherwise, an additional time-based AF discriminator can be used.

In one example implementation, a sudden onset AF discriminator algorithm can calculate a moving average R-R interval for each beat within the window based on a plurality of previous beats. For example, the moving average R-R interval for the current beat may be based on the instant R-R intervals associated with the four beats preceding the current beat. For each beat, there are two interval values associated with it—an instant R-R interval and a moving average R-R interval—and these two values are stored separately. In some configurations of the algorithm, if the instant R-R interval of one of the preceding four beats is outside a specified range, e.g. less than 300 msec or greater than 1300 msec, then the R-R interval of the outside beat may be replaced with another RR interval. Possible other R-R intervals may include a fixed RR interval (e.g., 800 msec), the instant RR interval of a neighboring beat or the average RR interval of a previous number of beats.

Once the moving average RR interval of the current beat is determined, it is compared to the moving average RR intervals of a set of previous beats. In one configuration the set of previous beats includes the $2^{nd}$, $4^{th}$, $6^{th}$ and $8^{th}$ and beat preceding the current beat. The difference between the maximum moving average R-R interval (max $R\text{-}R_{AVG}$) within the set of previous beats and the current beat moving average R-R interval ($R\text{-}R_{CURRENT}$) is calculated. This difference is referred to a "Δ moving average" and is compared to a threshold, such as 100 msec. If the different exceeds the threshold then a "significant change" in heart rate exists with respect to the current beat. This process is repeated for each of the remaining beats (e.g., 55 beats) in the window. The number of beats within the beat window for which a significant change has been detected is counted. If the total count exceeds a sudden onset (SO) threshold, e.g., 16, then the change in heart rate is considered "sudden" for the current beat and sudden onset is deemed detected for the current beat. In an alternate configuration, a running count of significant changes may be maintained and sudden onset detected as soon as the count exceeds the SO threshold. This may eliminate the need to process all beats within the window. Additional details of the aforementioned sudden onset detection techniques are described in U.S. Pat. No. 8,121,675 to Shaquer et al., titled "Device and Method for Detecting Atrial Fibrillation," which is incorporated herein by reference.

R-Wave Undersensing or Intermittent AV Conduction Block

R-wave undersensing can lead to false positive detections of AF. Another reason for false positive detections of AF is intermittent AV conduction block, which can result in R-R interval variability measurements that results in false positive detections of AF, even if the R-R intervals sensed by the IMD are correctly sensed during the intermittent AV conduction block. Interestingly, both R-wave undersensing and intermittent AV conduction block result in R-R interval measurements that are close to integer-multiples of neighboring R-R intervals.

For various reasons, including an implant angle of an IMD relative to the heart, the dynamically changing R-wave amplitude may occasionally be too small to detect leading to R-wave undersensing, unless clinicians lower the programmable R-wave sensing threshold to correct this. In other cases, R-wave oversensing resulting from P-wave and/or T-wave amplitudes exceeding the R-wave sensing threshold may lead clinicians to raise the programmable R-wave sensing threshold, which may also result in R-waves undersensing. Where T-waves and/or P-waves are falsely identified as R-waves, false R-R intervals can be identified which have a high variability, leading to false detections of AF. In other words, over-sensed P-waves and/or over-sensed T-waves can lead to false positive AF detections. An over-sensed P-wave, as the term is used herein, refers to a P-wave that is falsely identified as an R-wave. Similarly, an over-sensed T-wave, as the term is used herein, refers to a T-wave that is falsely identified as an R-wave. An under-sensed R-wave, as the term is used herein, refers to an R-wave that is not detected. An over-sensed R-wave, as the term is used herein, refers to a feature (e.g., a P-wave or a T-wave) of an EGM or ECG that is falsely identified as an R-wave.

As briefly discussed above with reference to step 212 in FIG. 2, a time-based AF discriminator can be used to detect R-wave undersensing or intermittent AV conduction block, if present, and based thereon, can determine whether to classify an AF detection as a false positive detection. Such an AF discriminator can rely on the fact that one under-sensed or blocked R-wave effectively doubles the perceived R-R interval. Likewise, two successively under-sensed or blocked R-waves triple the R-R interval, and so on. Thus, the ratio of each R-R interval to its neighboring R-R intervals can be used to identify potential instances of R-wave undersensing or AV conduction block. If the ratio is sufficiently close to an integer (e.g. 2.05, 3.96, etc. . . . ) and the R-R interval is sufficiently long (e.g., greater than 0.6 seconds, and thus, corresponding to a heart rate of less than 100 bpm), then the R-R interval is likely the result of one or more under-sensed and/or blocked R-waves. Explain another way, the duration of an R-R interval relative to the durations of its neighboring R-R intervals can be used to identify potential instances of R-wave undersensing or AV conduction block. More specifically, where the duration of an R-R interval is sufficiently close to being an integer multiple (e.g. 2.05, 3.96, etc. . . . ) of the durations of its neighboring R-R intervals and the R-R interval is sufficiently long (e.g., greater than 0.6 seconds, and thus, corresponding to a heart rate of less than 100 bpm), then the R-R interval is likely the result of one or more under-sensed and/or blocked R-waves. Because these aforementioned criteria may still be met during actual AF, each AF detection should preferably be verified (i.e., reevaluated) after removing or otherwise ignoring the potentially under-sensed/blocked R-R intervals.

Such an AF discriminator can use sensed R-R intervals to determine whether R-wave undersensing and/or AV conduction block has occurred, and more generally, to distinguish true R-R intervals from false R-R intervals. A true R-R interval, as the term is used herein, refers to an actual R-R interval corresponding to a period of non-AV condition block. A false R-R interval, as the term is used herein, refers to an interval that is mistakenly identified as an R-R interval, but is not an actual R-R interval. A false R-R interval may occur because of R-wave undersensing, e.g., if R-waves are correctly identified in portions of an EGM corresponding to an nth cardiac cycle and an (n+2)th cardiac cycle, but the R-wave is not identified due to R-wave undersensing in the (n+1)th cardiac cycle, leading to an R-R interval measurement being about double the true R-R interval. A false R-R interval may alternatively or additionally occur because of AV conduction block, e.g., if R-waves are present and correctly identified in portions of an EGM corresponding to an nth cardiac cycle and an (n+2)th cardiac cycle, but the R-wave is not present in the (n+1)th cardiac cycle because of AV conduction block, leading to an R-R interval measurement being about double the true R-R interval.

Other example types of intervals that may be mistakenly identified as an R-R interval, and thus are examples of false R-R intervals, include, but are not limited to, P-R intervals, R-T intervals, P-T intervals, and T-P intervals. A P-R interval can be mistakenly identified as an R-R interval where a P-wave is over-sensed. An R-T interval can be mistakenly identified as R-R interval where a T-wave is over-sensed. A P-T interval or a T-P interval can be mistakenly identified as an R-R interval where T- and P-waves are over-sensed and an R-wave is under-sensed. These types of false R-R intervals can also be referred to as over-sensed R-R intervals.

R-wave understanding or AV conduction block effectively causes a measured R-R interval to be substantially similar to an integer multiple (e.g., 2× or 3×) of a normal R-R interval, which can also be referred to as a true R-R interval or an actual R-R interval. Thus, certain embodiments identify intervals that are similar to an integer multiple of either the previous three (or some other number of) intervals or the next three (or some other number of) intervals, which are the real R-R intervals and do not correspond to R-wave undersensing or AV conduction block. Further analysis (e.g., arrythmia detection analysis) can then proceed using only the remaining R-R intervals.

In accordance with certain embodiments, a list of sensed R-R intervals is obtained for a recorded EGM clip (or ECG clip), which can also be referred to as a segment of an EGM, or an EGM segment. Because this list of R-R intervals may actually include one or more false R-R intervals, e.g., due to R-wave undersensing and/or intermittent AV conduction block, unless specifically referred to as being a “true R-R interval”, any interval referred to herein generally as an R-R interval may be a false R-R interval or a true R-R interval. It is also noted that the term potential R-R interval refers to an R-R interval that may be a false R-R interval or a true R-R interval. Further, it is noted that while a large portion of the following description and the patient example discussed below describes R-wave undersensing, the same principles also apply to intermittent AV conduction block.

Figure 4:
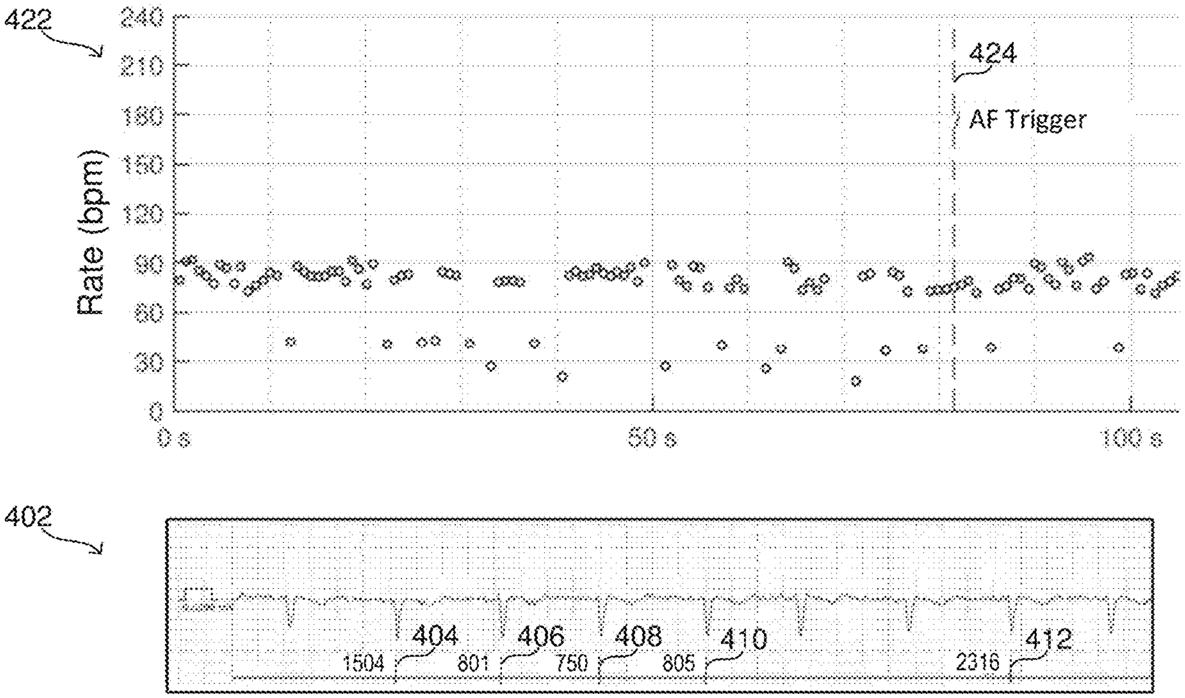
FIG. 4 includes a portion of an EGM segment that resulted in an AF detection due to under-sensed R-waves, and also includes a corresponding graph of heart rate (HR) versus time.

An example of R-wave undersensing is shown if FIG. 4. Although this specific example corresponds to an R-R interval pattern that resulted from R-wave undersensing, the same R-R interval pattern may be the result of intermitted AV conduction block, and the same principles would apply. At the bottom of FIG. 4 is shown a portion of an EGM segment 402 that resulted in an AF detection due to under-sensed R-waves. At the top of FIG. 4 is shown a graph or plot 422 that includes heart rate (HR) in beats per minute (bpm) along the vertical axis, and time in seconds (s) along the horizontal axis. The dashed vertical line 424 corresponds to an AF detection occurring at a point in time corresponding to ~82 seconds, and thus, the vertical line 424 is also marked AF Trigger. Because the AF detection represented by the dashed vertical line 424 may actually be a false AF detection, it can also be referred to more specifically as a potential AF detection, wherein the potential AF detection may or may not be a true AF detection. The potential AF detection may have been detected, e.g., if a measure of R-R interval variability exceeds a corresponding threshold, but is not limited thereto. Example techniques for detecting an AF episode, or more specifically, an AF episode, are described in U.S. Pat. No. 8,121,675 to Shaquer et al., titled “Device and Method for Detecting Atrial Fibrillation,” which is incorporated herein by reference. The use of other techniques for detecting potential AF episodes are also possible and within the scope of the embodiments described herein.

Figure 5:
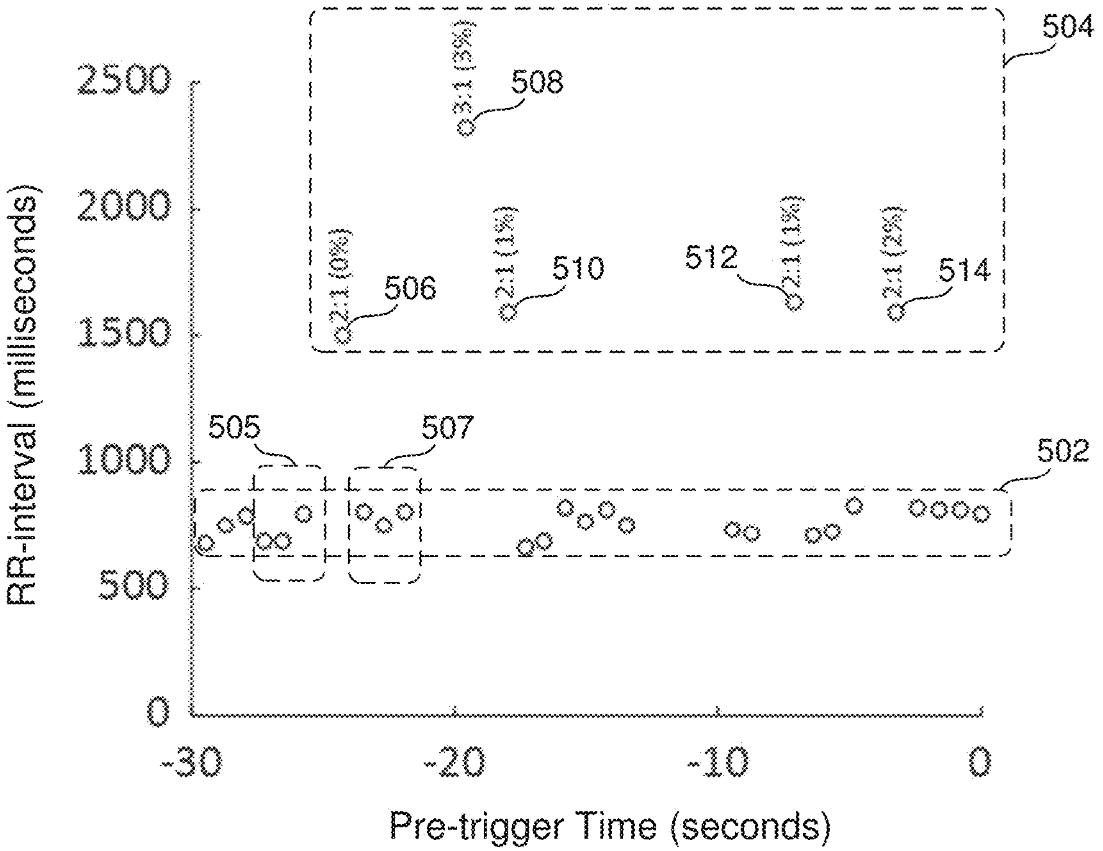
FIG. 5 includes a graph of R-R intervals for a window preceding the AF detection in FIG. 4, which R-R intervals correspond to the inverse of the heart rates shown in FIG. 4.

FIG. 5 illustrates a graph or plot of R-R intervals in milliseconds (ms) for a 30 second (s) window preceding the AF trigger 424 in FIG. 4, which R-R intervals correspond to the inverse of the heart rates that were shown in FIG. 4. In FIG. 5, the circles within the dashed outline 502 correspond to R-R intervals that are true R-R intervals, and the circles within the dashed outline 504 correspond to R-R intervals associated with under-sensed R-waves (with the maximum ratio and % difference relative to neighboring R-R intervals indicated next to each circle within the dashed outline 504).

Since the R-R intervals within the dashed outline 504 are not true R-R intervals, they can be referred to as false R-R intervals.

Figure 6:
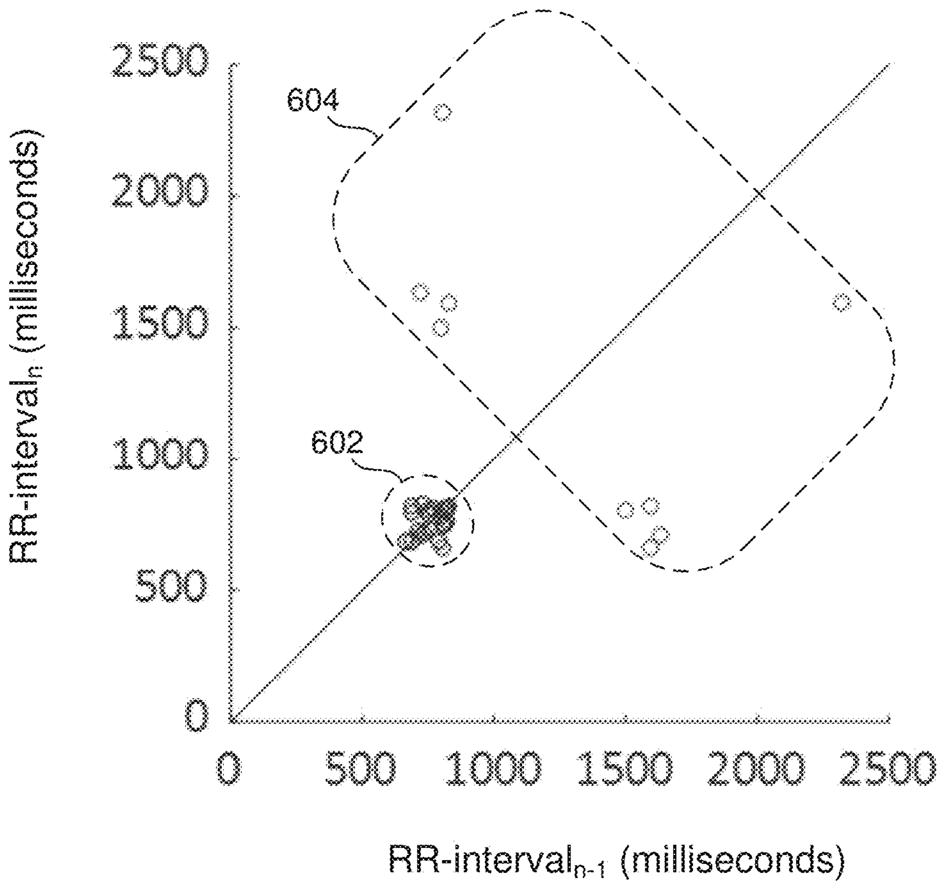
FIG. 6 includes a Poincare plot that illustrates the relationship between each R-R interval in the EGM segment shown in FIG. 4 and its immediately following R-R interval, i.e., illustrates the relationship between successive R-R intervals.

The Poincare plot shown in FIG. 6 plots the relationship between each R-R interval in the EGM segment 102 and its immediately following R-R interval, i.e., illustrates the relationship between successive R-R intervals. The circles within the dashed outline 602 correspond to true R-R intervals. The circles within the dashed outline 604 correspond to false R-R intervals that result from R-wave undersensing. Similar false R-R intervals may result for intermittent AV conduction block, instead of R-wave undersensing.

In accordance with certain embodiments, for each R-R interval in a window (e.g., a 30 second window) preceding the AF trigger (i.e., leading up to the detection of an AF episode), a ratio ("r") is calculated relative to each of a number of neighboring R-R intervals (e.g., the immediately preceding three intervals and immediately following three intervals). In specific embodiments, the analysis skips the first three (or some other number of) R-R intervals and last three (or some other number of) R-R intervals in the 30 second window, since the R-R intervals near the start and the end of the window have minimal neighbors to one side. All the ratios that round to less than 2 are eliminated.

Next, after the R-R intervals having a rounded ratio of less than 2 are eliminated, an indicator of a difference between each remaining analyzed R-R interval and its neighboring R-R intervals is determined. In certain embodiments, the indicator of the difference between each analyzed R-R interval and its neighboring R-R intervals is a percent difference that is calculated using the following equation:

$$\%\ \text{difference}=100\times|r-\text{round}(r)|/\text{round}(r)$$

where,

- r is the ratio of the analyzed R-R interval relative to a neighboring R-R interval, and
- round (r) is the calculated ratio rounded to the nearest integer.

The minimum percent difference (or more generally, the minimum indicator of the difference) for an analyzed R-R interval relative to all six (or some other number of) neighbors is then used to potentially flag the analyzed R-R interval as being associated with undersensing or AV conduction block. These rounded ratios and percent differences are listed next to each of the circles within the dashed outline 504 in FIG. 5. More specifically, for the circle labeled 506 (at approximately 25 seconds prior to the AF trigger) the rounded ratio is 2:1 and the percentage difference is 0%; for the circle labeled 208 (at approximately 20 seconds prior to the AF trigger) the rounded ratio is 3:1 and the percentage difference is 3%; for the circle labeled 510 (at approximately 18 seconds prior to the AF trigger) the rounded ratio is 2:1 and the percentage difference is 1%; for the circle labeled 512 (at approximately 7 seconds prior to the AF trigger) the rounded ratio is 2:1 and the percentage difference is 1%; and for the circle labeled 514 (at approximately 4 seconds prior to the AF trigger) the rounded ratio is 2:1 and the percentage difference is 2%.

Referring specifically to the circle labeled 506 (at approximately 25 seconds prior to the AF trigger), the under-sensed R-R interval has a duration (aka value) of 1500 milliseconds (ms). The durations (aka values) of the three neighboring R-R intervals immediately preceding the 1500 ms under-sensed R-R interval (represented by the three circles within the dashed outline labeled 205) are 700 ms, 700 ms, and 750 ms. The durations of three neighboring R-R intervals immediately following the 1500 ms under-sensed R-R interval (represented by the circles within the dashed outline labeled 207) are 760 ms, 740 ms, and 750 ms. The ratios of the under-sensed R-R interval (having the value of 1500 ms) relative to the three neighboring R-R intervals on either side are as follows: [1500/700, 1500/700, 1500/750, 1500/760, 1500/740, 1500/750]=[2.14, 2.14, 2.00, 1.97, 2.03, 2.00]. These correspond to % differences of: [7%, 7%, 0%, 1.5%, 1.5%, 0%]. The minimum % difference of 0% indicates that the current interval (1500 ms) is "close to" an integer multiple of a neighboring R-R interval (in this case, a 0% difference from 2× a neighboring R-R interval).

In accordance with certain embodiments, two criteria are ultimately applied in order to determine whether an R-R interval being analyzed (aka an analyzed R-R interval) should be classified as being a false R-R interval associated with R-wave undersensing or AV conduction block (which can be collectively referred to as R-wave undersensing/block), and thus, can be more generally classified as a false R-R interval.

One criteria is that the minimum percent difference of the ratios relative to all six (or some other number) of its neighbors is less than a specified difference threshold, e.g., less than 10%. This criterion ensures that the interval in question is reasonably close to an integer multiple of at least one of its neighboring R-R intervals, where the integer multiple is at least 2. Note that the minimum percent difference threshold may also be programmable depending on the clinical need. For example, it may be specified as less than 10% if AF sensitivity is important, but may alternatively be specified as greater than 10% (e.g., 15%) if a reduction in false positive AF detections (aka AF specificity) is preferred.

Another criteria is that the interval value is greater than a specified duration threshold, e.g., greater than 600 ms (i.e., corresponding to a HR of less than 100 bpm). This criterion ensures that P-wave or T-wave oversensing midway between an R-R interval does not result in a true R-R interval being flagged as a false R-R interval for being twice the duration of a neighboring R-R interval.

Once the false R-R-intervals (due to R-wave undersensing and/or AV conduction block) within the 30 second window (leading up to the AF detection) have been identified, there is a determination of what percent of the R-R intervals were identified as false R-R intervals (due to R-wave undersensing and/or AV conduction block). This false R-R interval percentage, which can also be referred to more specifically as the "undersensing/AV conduction block percent," quantifies the incidence of R-wave undersensing and/or AV conduction block within the window.

In addition, the identified false R-R intervals (due to R-wave undersensing and/or AV conduction block) are removed from the ordered list of R-R intervals (included in the window leading up to the AF detection) to thereby produced a corrected list of R-R intervals. Based on the corrected list of R-R intervals, a median interval-interval % difference is calculated (using the above described equation % difference=100×|r−round(r)|/round(r)) to thereby produce a "corrected interval variability."

Ultimately, the entire window is classified (aka flagged) as being a false positive AF detection (due to R-wave undersensing and/or AV conduction block) if the following criteria are met: (1) the "undersensing/AV conduction block percent" is greater than a specified false-detection threshold (e.g., >5%), which criterion ensures that a sufficient number of undersensing/AV conduction block-related false R-R intervals exist, such that they may have influenced AF detection; and (2) the "corrected interval variability" is less than a specified variability threshold (e.g., <5%). Note that, during actual AF, some intervals may still be labeled as false R-R intervals (due to R-wave undersensing and/or AV conduction block) if they randomly are similar to integer-multiples of neighboring R-R intervals. This second criterion is used to recognize when the rhythm is otherwise stable, after false R-R intervals (due to R-wave undersensing and/or AV conduction block) have been removed.

The example window leading up to the AF detection, described above with reference to FIGS. 4-6, was associated with an "undersensing/AV conduction block percent" of 20.0% and a "corrected interval variability" of 3.4%, thus satisfying the above criteria to be flagged as a false AF detection.

Additional details of the embodiments summarized above are described below with reference to the high level flow diagrams in FIGS. 7A and 7B, which can be collectively referred to as FIG. 7. More specifically, FIG. 7 is used to summarize certain methods for improving R-R interval detection specificity, and AF episode detection specificity. Such a method may be triggered in response to a detection of an AF episode. In other words, the methods summarized with reference to the high level flow diagram in FIG. 7 can be used to identify false R-R intervals that are due to R-wave undersensing and/or AV conduction blow, as well as to detect false positive AF detections.

Figure 7A:
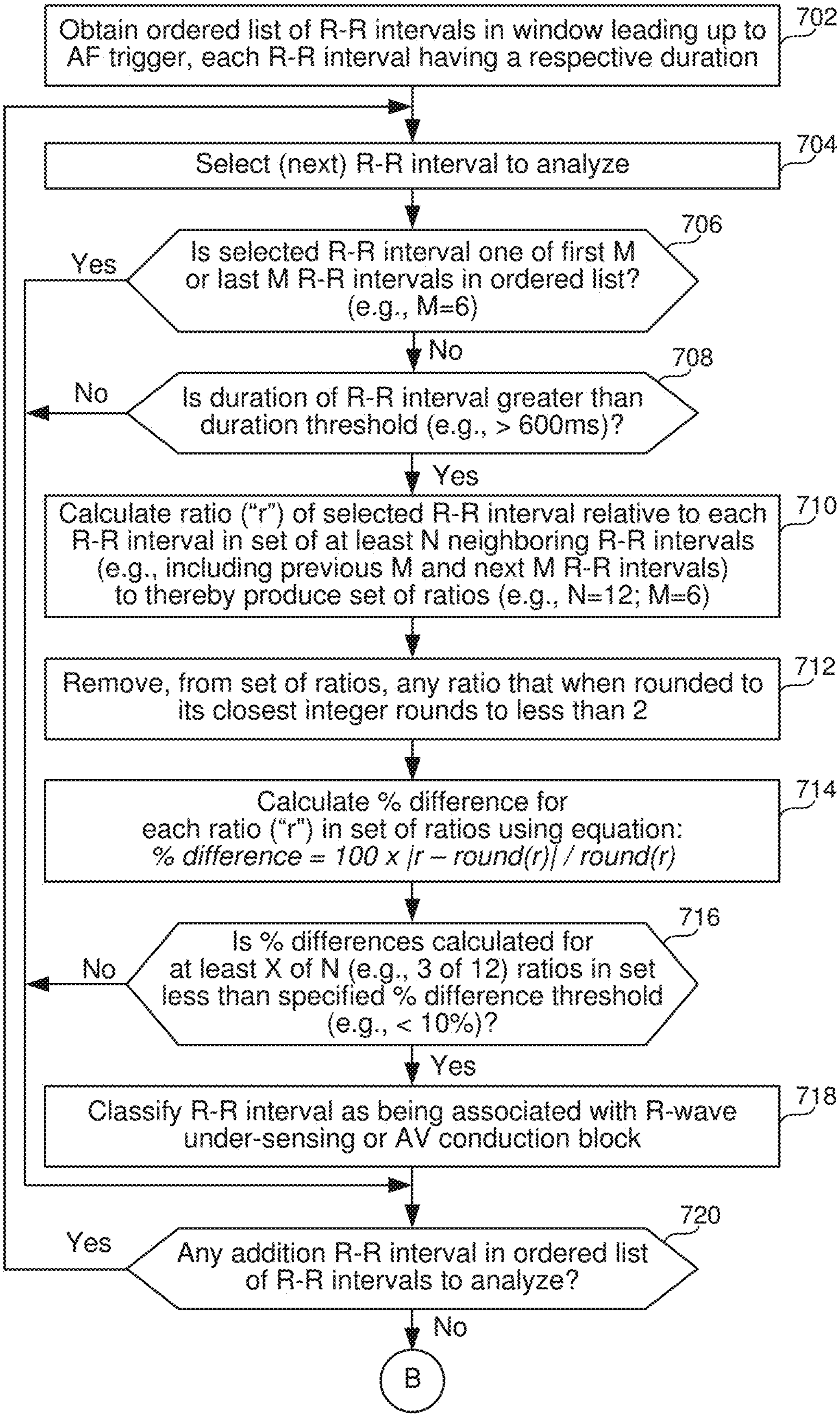
FIGS. 7A and 7B, which can be collectively referred to as FIG. 7, includes a high level flow diagram that is used to describe how true R-R intervals can be distinguished from false R-R intervals associated with R-wave undersensing or AV conduction block, and how the results of such an analysis can be used to determine whether to classify a detection of an AF episode as a false positive detection.

Referring to FIG. 7A, step 702 involves obtaining an ordered list of R-R intervals within a window leading up to a detection of an AF episode, wherein each of the R-R intervals has a respective duration. The ordered list of R-R intervals can be obtained, for example, by identifying R-waves within an EGM or ECG segment, and determining intervals between consecutive ones of the R-waves to thereby produce the ordered list of R-R intervals. Such R-waves can be identified within the EGM or ECG segment by comparing the EGM or ECG segment, or samples thereof, to an R-wave sensing threshold, and identifying R-waves when the R-wave sensing threshold is reached or exceeded. Other variations are also possible and within the scope of the embodiments described herein. For example, R-waves can alternatively or additionally be identified using R-wave or QRS complex morphology templates.

The ordered list of R-R intervals, obtained at step 702, would preferably include only true R-R intervals. However, due to R-wave oversensing and/or AV conduction block, the ordered list of intervals obtained at step 702 may also include one or more false R-R intervals. In other words, the ordered list of R-R intervals, included in the window leading up to the detection of the AF episode (aka an "AF trigger"), in addition to including true R-R intervals, may also include one or more false R-R intervals that may be present, e.g., if R-waves are under-sensed (i.e., present but not detected) and/or if the patient experiences AV conduction block that results in one or more missing R-waves. In order to maximize the specificity of the methods summarized with reference to FIG. 7A, one or more techniques for identifying and removing or otherwise compensating for other types of false R-R intervals can be performed prior to step 702, as part of step 702, or between step 702 and the next step 704.

Step 704 involves selecting an R-R interval (from the ordered list of R-R intervals obtained at step 702) to analyze. The first time step 704 is performed (for an ordered list of intervals), the first R-R interval in the ordered list can be selected. The second time step 704 is performed (for the ordered list of intervals), the second R-R interval in the ordered list can be selected, and so on.

At step 706 there is a determination of whether the R-R interval (selected at step 704 for analysis) is the one of the first M or last M R-R intervals in the ordered list of intervals (e.g., M=3). If the selected interval is one of the first M or last M R-R intervals in the list (i.e., if the answer to the determination at step 706 is Yes), then flow goes to step 720 (thereby skipping steps 708-718). If the selected interval is not one of the first M or last M R-R intervals in the list (i.e., if the answer to the determination at step 706 is No), then flow goes to step 708.

At step 708 there is a determination of whether a duration of the R-R interval (selected at step 704 for analysis) is greater than a specified duration threshold, e.g., greater than 600 ms (i.e., corresponding to a HR of less than 100 bpm). As noted above, this criterion ensures that P-wave or T-wave oversensing midway between an R-R interval does not result in a true R-R interval being flagged as a false R-R interval for being twice the duration of a neighboring R-R interval.

At step 710, for the R-R interval being analyzed a ratio ("r") is calculated relative to each of the N neighboring R-R intervals (e.g., the immediately preceding M intervals and immediately following M intervals), or more generally, relative to each R-R interval in a set of N neighboring R-R intervals, where N is at least 6, and M is at least 3. The result of step 710 is a set of ratios.

Step 712 involves removing, from the set of ratios, any ratio that when rounded to its closest integer rounds to less than two. In other words, any ratio (in the set of ratios) having a value that is less than 1.5 is removed from the set, since when rounded to the closest integer it would round to one, which is less than two.

Step 714 involves determining an indicator of a difference between a duration of the R-R interval (selected at step 704 for analysis) and those of its N neighboring R-R intervals that were not removed at step 712. In certain embodiments, the indicator of the difference between the analyzed R-R interval and its neighboring R-R intervals (that were not removed at step 712) is a percent difference that is calculated using the equation:

$$\%\ \text{difference}=100\times|r-\text{round}(r)|/\text{round}(r)$$

where, r is the ratio of the analyzed R-R interval relative to a neighboring R-R interval, and round (r) is the calculated ratio rounded to the nearest integer.

Step 716 involves determining whether the % differences (or more generally, indicators of the difference), for at least a specified number X of the ratios in the set, is less than a specified difference threshold (e.g., <10%). This criterion ensures that the interval in question is reasonably close to an integer multiple of at least X of its neighboring R-R intervals, where the integer multiple is at least 2, and where X is a specified integer that is at least 1. If the answer to the determination at step 716 is Yes, then flow goes to step 718 and the R-R interval being analyzed is classified as being a false R-R interval associated with R-wave undersensing or AV conduction block. If the answer to the determination at step 716 is No, then flow goes to step 720. Still referring to step 716, the minimum percent difference threshold may be programmable depending on the clinical need, as noted above. Similarly, the value for X may be programmable depending on the clinical need. For example, the specified difference threshold can be 10%, and the value for X can be 1, if AF sensitivity is important; or the specified difference threshold can be 15%, and the value for X can be 2, if specificity is more important that sensitivity.

At step 720 there is a determination of whether there is any additional R-R interval in the ordered list of R-R intervals (obtained at step 702) to analyze. If the answer to step 720 is Yes, then flow returns to step 704 and the next R-R interval in the list (obtained at step 702) is selected for analysis. In this manner, steps 704-720 are repeated until the answer to the determination at step 720 is No, at which point flow goes to step 722 in FIG. 7B.

Figure 7B:
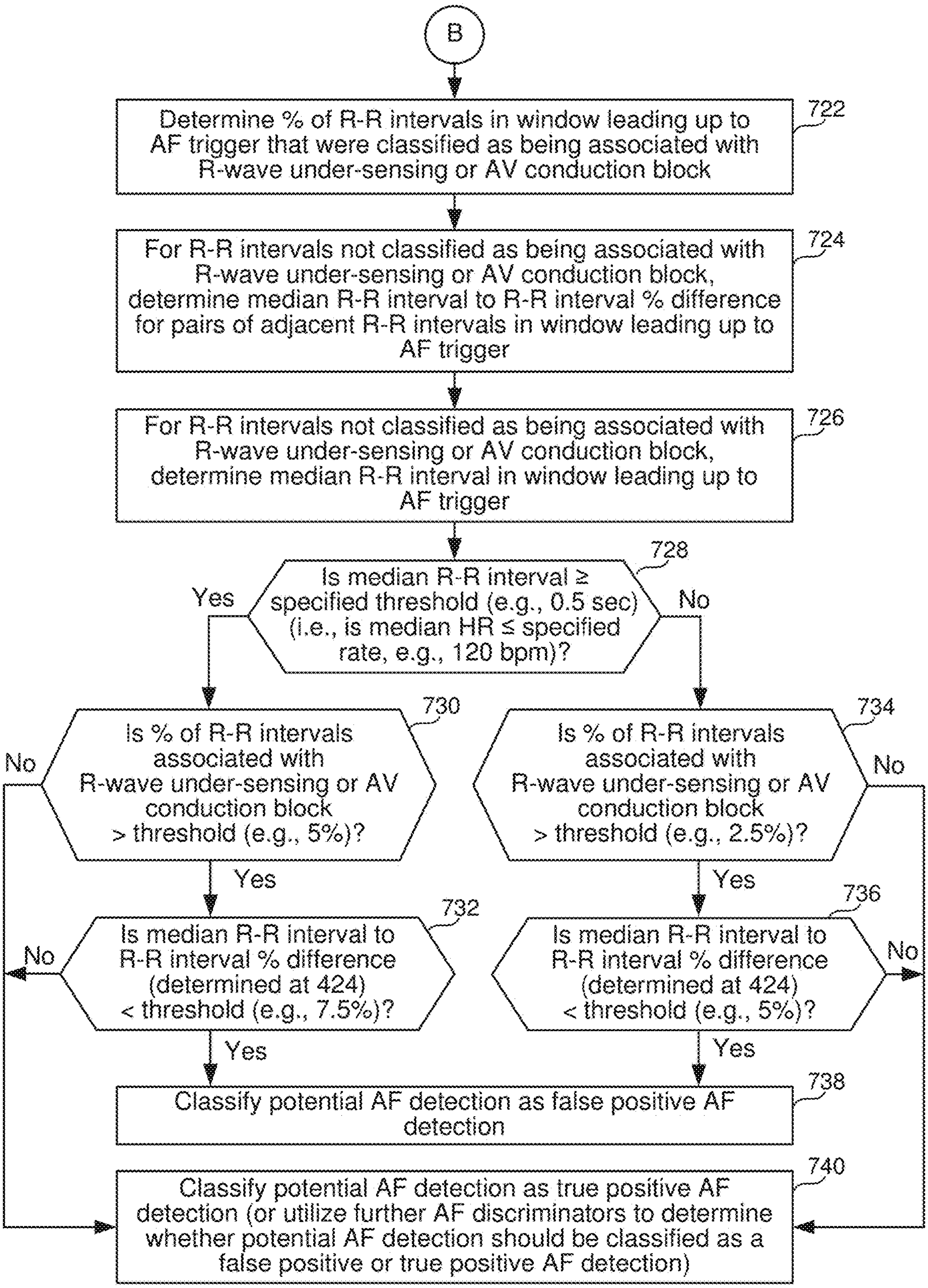

Referring to FIG. 7B, at step 722 there is a determination of what percent of the R-R intervals, in the window leading up to the detection of the AF episode, were classified as being associated with at least one of R-wave undersensing or AV conduction block. For an example, if there were 70 R-R intervals in the window leading up to the detection of the AF episode, and 10 of those R-R intervals were classified as being associated with at least one of R-wave undersensing or AV conduction block, then the result of step 722 would be 25 percent. The percent that is determined at step 722 can also be referred to herein as the R-wave undersensing/block percent.

At step 724 there is a determination of the median R-R interval to R-R interval percentage difference, for those R-R intervals (in the window leading up to the detection of the AF episode) that were not classified as being associated with at least one of R-wave undersensing or AV conduction block. Continuing with the above example, where 10 of 40 R-R intervals were classified as being associated with at least one of R-wave undersensing or AV conduction block, at step 724 there is a determination of the median R-R interval to R-R interval percentage difference for the remaining 30 R-R intervals (that were not classified as being associated with R-wave undersensing/ block). This would involve determining the % differences between the $1^{st}$ and $2^{nd}$ R-R intervals, between the $2^{nd}$ and $3^{rd}$ R-R intervals, between the $3^{rd}$ and $4^{th}$ R-R intervals, . . . between the $29^{th}$ and $30^{th}$ R-R intervals, thereby resulting in 29 separate % differences, or more generally Z−1 separate % differences (where Z is how many R-R intervals within the window were not classified as being associated with R-wave undersensing/ block). To find the median of the Z−1 separate % differences (e.g., the 29 separate % differences), the % differences can be arranged in order from least to greatest, and the median is the value that is halfway into the set, i.e., the middlemost value. If there is an even number of values in the data set, then the median can be determined by determining the mean (average) of the two middlemost numbers, or selecting either one of the two middlemost numbers, depending upon the specific implementation. The idea here is that R-R intervals associated with "true" R-waves should be relatively consistent and not vary wildly when a patient is not experiencing an actual AF episode. If the remaining R-R intervals (i.e., those not associated with R-wave undersensing/block) are not relatively consistent and vary wildly, then that is indicative of the patient likely having experienced an actual AF episode.

At step 726 there is a determination of the median R-R interval of those R-R in intervals (in the window leading up to the detection of the AF episode) that were not classified as being associated with at least one of R-wave undersensing or AV conduction block (aka R-wave undersensing/block).

At step 728 there is a determination of whether the median R-R interval (determine at step 726) is greater than or equal to a specified duration threshold, such as 0.5 seconds. This is equivalent to determining whether the median HR for the patient (corresponding to the R-R intervals in the window leading up to the detection of the AF episode, which were not classified as being associated with R-wave undersensing/block) is less than or equal to a specified HR threshold, e.g., 120 beats per minute (bpm). If the answer to the determination at step 728 is Yes, then flow goes to step 730. If the answer to the determination at step 730 is No, then flow goes to step 734.

At step 730 there is a determination whether the R-wave undersensing/block percent (that was determined at step 722) is greater than a first specified percent threshold, e.g., >5%. This criterion is used to determine whether enough R-waves were classified as being associated with R-wave undersensing/block, such that they may have influenced the initial AF detection/trigger. If the answer to the determination at step 730 is Yes, then flow goes to step 732.

At step 732 there is a determination of whether the median R-R interval to R-R interval % difference (that was determined at step 724) is less than a first median percent difference threshold, e.g., <7.5%. This criterion is used to determine whether the R-R intervals associated with "true" R-waves (i.e., not associated with R-wave undersensing/block) are relatively consistent and do not vary wildly, which would be indicative of the patient not experiencing an actual AF episode. Explain another way, during actual AF, some R-R intervals may still be classified as being associated with R-wave undersensing/block if the R-R intervals randomly are similar to integer-multiples of neighboring R-R intervals. This criterion checks whether, without these R-wave undersensing/block-related R-R intervals, the rhythm is otherwise stable. If the answer to the determination at step 732 is Yes, then flow goes to step 738. At step 738 the AF episode is classified as a false positive detection. Explained another way, at step 738 the AF trigger or detection of the AF episode is rejected. The order of steps 730 and 732 can be reversed. Similarly, the orders of steps 722, 724, and 726 can be rearranged.

If the answer to either one of steps 730 or 732 is No, then flow goes to step 740. At step 740 the AF episode can be classified as a true AF episode, or a confidence level or probability that the AF episode was actually a true AF episode can be increased, or one or more further AF discriminators can be used to determine whether the potential AF detection should be classified as a true positive or false positive AF detection.

Referring back to step 728, if the answer to the determination at step 728 is No, then flow goes to step 734. At step 734 there is a determination whether the R-wave undersensing/block percent (that was determined at step 722) is greater than a second specified percent threshold, e.g., >2.5%, which is less than the first specified percent threshold used at step 730. If the answer to the determination at step 734 is Yes, then flow goes to step 736.

At step 736 there is a determination of whether the median R-R interval to R-R interval % difference (that was determined at step 724) is less than a second median percent difference threshold, e.g., <5%., which is less than the first median percent difference threshold used at step 732. If the answer to the determination at step 736 is Yes, then flow goes to step 738, at which the AF detection is classified as a false positive detection. The order of steps 734 and 736 can be reversed.

If the answer to either one of steps 734 or 736 is No, then flow goes to step 740. As noted above, at step 740 the detected AF episode can be classified as a true AF episode, or a confidence level or probability that the AF episode was actually a true AF episode can be increased, or one or more further AF discriminators can be used to determine whether the AF detection should be classified as a true positive or false positive AF detection.

The thresholds used in the branch at the right in FIG. 7B (which includes steps 734 and 736) are lower than the respective thresholds used in the branch at the left in FIG. 7B (which includes step 730 and 732). This is to account for there being less of a chance that an AF detection is a false positive, if the answer to the determination at step 728 is No. More specifically, the second specified percent threshold (e.g., 2.5%) used at step 734 is less than the first specified percent threshold (e.g., 5%) used at step 730 to account for the fact that an AF detection algorithm (used to detect the AF episode in the first place) likely has a greater sensitivity at higher heart rates and can be easily triggered by a few just a few under-sensed/blocked R-waves. Additionally, the second median percent difference threshold (e.g., 5%) used at step 736 is less than the first median percent difference threshold (e.g., 7.5%) used at step 732 to be more conservative when labeling faster rhythms as being associated with R-wave undersensing/block, as fast rhythms are more likely to truly be AF.

In an alternative embodiment, the branch on the right (which includes steps 734 and 736) is eliminated, and if the answer to the determination at step 728 is No, then flow goes directly to step 740.

In accordance with certain embodiments, an IMD may perform the method described above with reference to FIG. 7 in response to an AF episode being detected. The detection of an AF episode can also be referred to as an AF trigger. Such an IMD may be configured to transmit, to an external device that is communicatively coupled to a patient care network, data corresponding to an AF episode that is detected by the IMD. In certain such embodiments, the IMD does not (is prevented from) transmitting (to the external device that is communicatively coupled to the patient care network) data corresponding to an AF episode that is detected by the IMD, but is thereafter determined by the IMD as being a false positive detection. The IMD can also be configured to allow overwriting in the memory of data corresponding to an AF episode that was detected by the IMD but is thereafter determined by the IMD as being a false positive detection. Alternatively, the IMD can prevent storing in the memory of data corresponding to an AF episode that is detected by the IMD but is thereafter determined by the IMD as being a false positive detection.

In accordance with certain embodiments, the medical device (e.g., IMD) that performs the method described above with reference to FIG. 7 may monitor the HR of a patient based on R-R intervals identified from a segment of an EGM or ECG, and the medical device can determine based on the results of the method whether a monitored HR is inaccurate due to oversensing and thus should be ignored or recalculated. For an example, if at least a specified amount of R-R intervals classified as being associated with R-wave oversensing/block exceeds a corresponding threshold, the medical device can conclude that a HR that was determined based on sensed interval is inaccurate and should not be used, or should be recalculated.

The example thresholds described herein were conservatively chosen to limit the number of true AF episodes being incorrectly classified as false detections due to R-wave undersensing/block. However, the basic logic of the embodiments described herein can extend beyond the above limitations. The specific values of each threshold can be more systematically optimized for a narrow patient population, a broader patient population, or for individual patients. Accordingly, embodiments described herein should not be limited to use with the example thresholds described herein.

Figure 8:
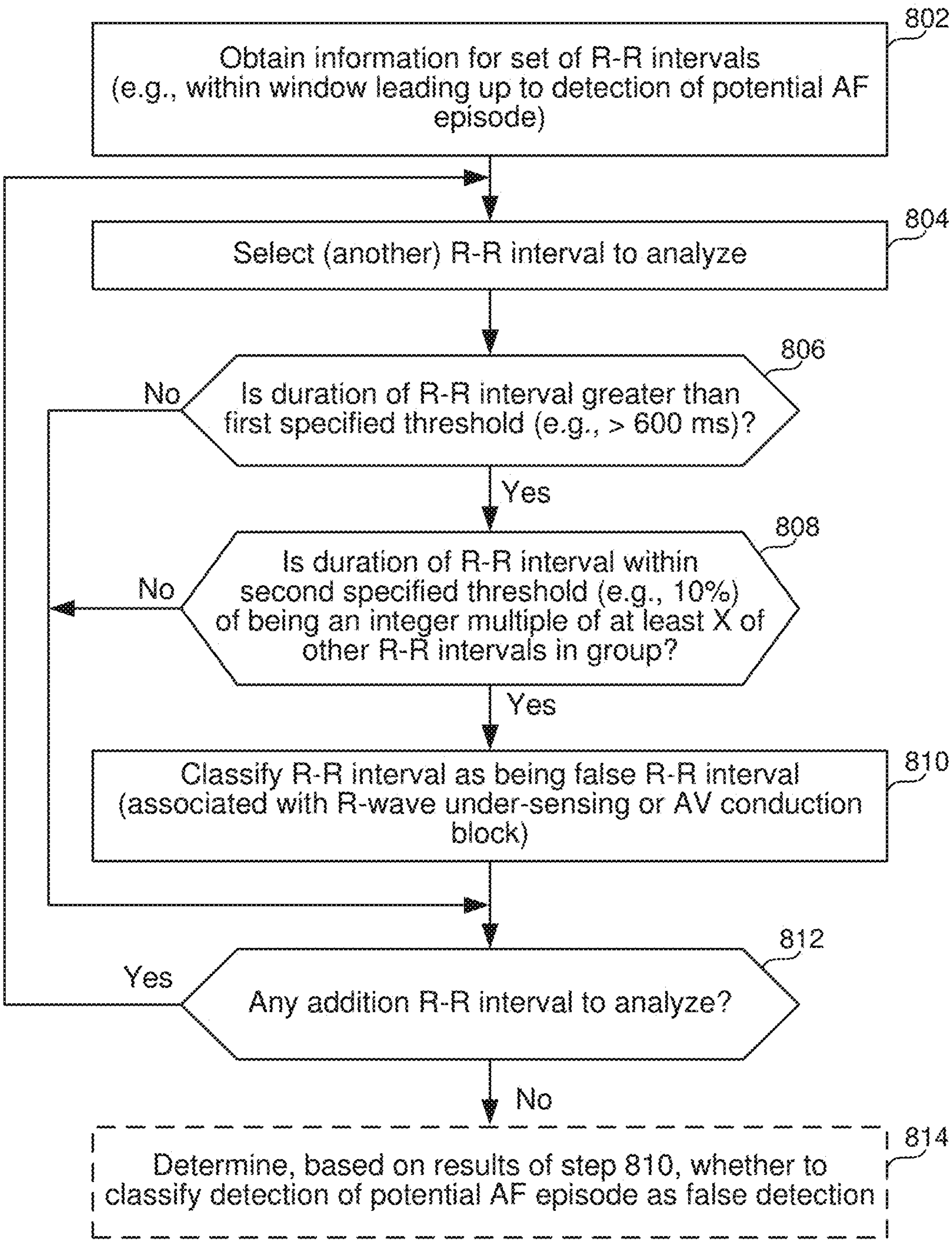
FIG. 8 is a high level flow diagram that is used to summarize methods, for use by a device or system that monitors cardiac activity, wherein such a method can be used to identify false R-R intervals and/or false AF detections.

The high level flow diagram of FIG. 8 is used to summarize certain methods for use by a device or system that monitors cardiac activity, wherein such a method can be used to identify false R-R intervals and/or false AF detections. The embodiments summarized above with reference to FIG. 7 are specific implementations of the methods summarized with reference to FIG. 8.

Referring to FIG. 8, step 802 involves obtaining information for a set of R-R intervals, wherein each of the R-R intervals has a respective duration, and each of the R-R intervals may be a true R-R interval or a false R-R interval. Such a set of R-R intervals can be, e.g., the R-R intervals within a window (e.g., a 30 second window) leading up to the detection of an AF episode, but is not limited thereto. This set should include at least three R-R intervals, but will likely include much more, e.g., at least twenty R-R intervals, but not limited thereto.

Step 804 involves selecting an R-R interval to analyze. Step 806 involves determining whether the duration of the R-R intervals is greater than a first specified threshold (e.g., 600 ms), and step 808 involves determining whether the duration of the R-R interval is within a second specified threshold (e.g., 10%) of being an integer multiple of at least X of the other R-R intervals for which information is obtained, wherein the integer multiple is at least 2, and wherein X is a specified integer that is 1 or greater. Step 810 involves classifying one of the R-R intervals as being a false R-R interval, in response to both the duration of the R-R interval being greater than the first specified threshold (e.g., 600 ms), and the duration of the R-R interval being within the second specified threshold (e.g., 10%) of being an integer multiple of at least X of the other R-R intervals for which information is obtained. At step 812 there is a determination of whether there is an additional R-R interval to analyze. If the answer to the determination at step 812 is Yes, then flow returns to step 804. At optional step 814 there is a determination of whether to classify an AF episode as a false detection, e.g., if at least a specified percent or number of R-R intervals are classified as false R-R intervals, and/or if after removing the false R-R intervals, the variability and/or other characteristics of the remaining R-R intervals are indicative of the AF episode actually being a true AF episode.

Figure 9:
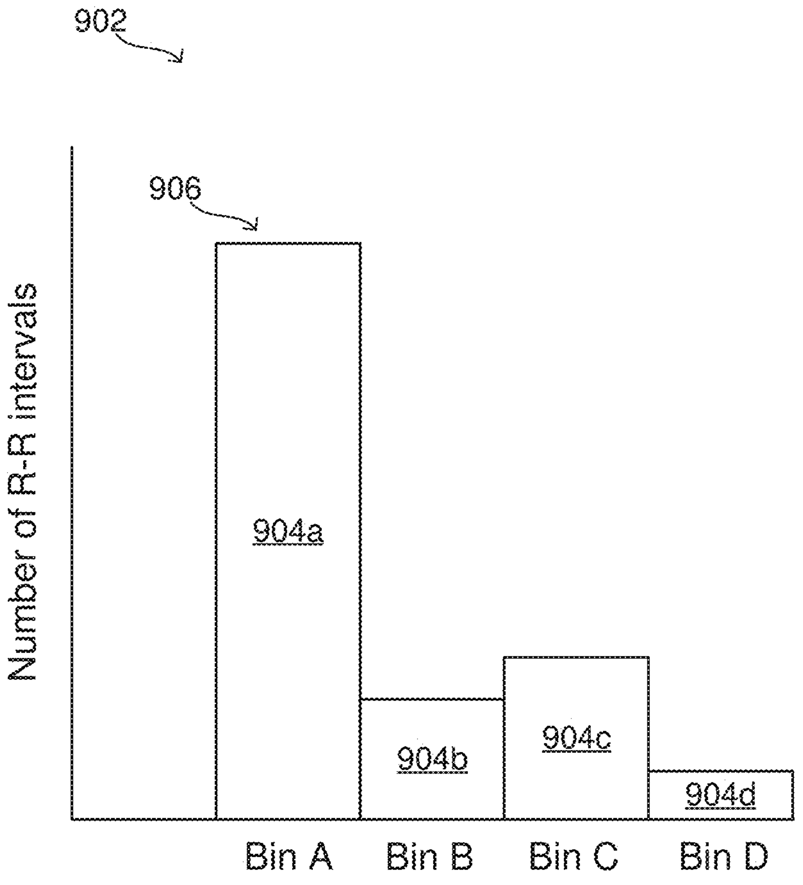
FIG. 9 illustrates an exemplary histogram that can be generated and used to determine which group of R-R intervals within a set of R-R intervals is the dominant group, and thus, likely includes true R-R intervals that can be compared to R-R intervals outside the dominant group to determine whether the R-R intervals group are false R-R intervals associated with R-wave undersensing or AV conduction block.

In accordance with certain embodiments, between steps 802 and 804, the R-R intervals in the set are grouped into two or more groups based on the durations of the R-R intervals, such that R-R intervals that are within a third specified threshold (e.g., within 15%) of one another are grouped into a same one of the groups, and the group that includes a greatest number of R-R intervals is classified as a dominant group. In such embodiments, the other R-R intervals in the group, that are used at instances of step 808, are the R-R intervals that are within the dominant group, which are most likely true R-R intervals. Such a grouping can result in a histogram, such as the one shown in FIG. 9. Referring to FIG. 9, the example histogram 902 shown therein includes a plurality of bins 904*a*, 904*b*, 904*c*, 904*d*, each of which corresponds to R-R intervals that are within the third specified threshold (e.g., 15% or 20%) of one another. Using such a histogram, the dominant group 906 can be identified by identifying the one of the bins having the greatest number of R-R intervals therein. It can be presumed that R-R intervals that are within the dominant group are true R-R intervals. Accordingly, in certain embodiments, at instances of step 804 (in FIG. 8), it may be that only R-R intervals that are not in the dominant group are selected for analysis. Unless otherwise specified, when selecting an R-R interval at instances of step 804, the R-R intervals need not be selected in any specific order.

Irregular R-R-Intervals Due to T-Wave and/or P-Wave Over-Sensing

As noted above, a common technique for detecting AF is based on measures of R-R interval variability. However, where T-waves and/or P-waves are falsely identified as R-waves, false R-R intervals can be identified which have a high variability, leading to false detections of AF. In other words, over-sensed P-waves and/or over-sensed T-waves can lead to false positive AF detections. An over-sensed P-wave, as the term is used herein, refers to a P-wave that is falsely identified as an R-wave. Similarly, an over-sensed T-wave, as the term is used herein, refers to a T-wave that is falsely identified as an R-wave. An under-sensed R-wave, as the term is used herein, refers to an R-wave that is not detected, as was noted above As briefly discussed above with reference to step 214 in FIG. 2, a time-based AF discriminator can be used to detect irregular R-R intervals due to T-wave and/or P-wave over-sensing, if present, and based thereon, can determine whether to classify an AF detection as a false positive detection. Details of such a time-based AF discriminator are described below with reference to FIGS. 10-13.

Certain embodiments described herein relate to methods and devices that use sensed intervals to determine whether P-wave and/or T-wave oversensing has occurred, and more generally, to distinguish true R-R intervals from false R-R intervals. These embodiments can beneficially be used, for example, to prevent or reject false positive AF detections before they are transmitted to a clinician, consequently improving AF detection specificity and reducing down-stream clinical resources. A true R-R interval, as the term is used herein, refers to an actual R-R interval. A false R-R interval, as the term is used herein, refers to an interval that is mistakenly identified as an R-R interval, but is not an actual R-R interval. Exemplary types of intervals that may be mistakenly identified as an R-R interval, and thus are examples of false R-R intervals, include, but are not limited to, P-R intervals, R-T intervals, P-T intervals, and T-P intervals. A P-R interval can be mistakenly identified as an R-R interval where a P-wave is over-sensed. An R-T interval can be mistakenly identified as R-R interval where a T-wave is over-sensed. A P-T interval or a T-P interval can be mistakenly identified as an R-R interval where T- and P-waves are over-sensed and an R-wave is under-sensed. These are just a few examples of types of false R-R intervals and how they may occur, which examples are not intended to be all inclusive. False R-R intervals are also referred to herein as over-sensed R-R intervals.

Over-sensed P-waves and/or T-waves can be detected by relying on the phenomenon that an over-sensed P-wave or an over-sensed T-wave effectively divides a normal R-R interval into two shorter intervals (e.g. an R-T interval and a T-R interval), the sum of which is an actual R-R interval, which can also be referred to as the true R-R interval. Thus, an over-sensed P-wave or an over-sensed T-wave can be detected by identifying intervals that are similar to the sum of either the last two intervals or the next two intervals, which are the real R-R intervals, and do not correspond to oversensing. Further analysis (e.g., arrythmia detection analysis) can then proceed using only the remaining intervals. Of the remaining R-R intervals, intervals are flagged if, looking at the next two intervals, they follow a "short-long-short" pattern, wherein the terms "short" and "long" are relative terms, as both groups of intervals are much shorter than true R-R intervals. Of these flagged intervals, an "oversensing score" can be calculated as the percentage of these intervals which are (i) sufficiently similar in duration to the neighboring flagged intervals, (ii) sufficiently different in duration from the neighboring (unflagged) intervals, and (iii) sufficiently short in duration. This "oversensing score" can be an estimate of the percentage of intervals that either start or end with an over-sensed R-wave. Explained another way, the "oversensing score" can be an estimate of the percentage of short intervals that classified as over-sensed R-R intervals. If the "oversensing score" in the window preceding an AF trigger exceeds a specified threshold (e.g. 50%), then the AF trigger can be associated with oversensing (i.e., false positive AF), and can be rejected. Further and alternative details of such embodiments are described below.

In accordance with certain embodiments, a list of potential sensed R-R intervals is obtained for a recorded EGM clip, which can also be referred to as a segment of an EGM, or an EGM segment. Because this list of potential R-R intervals may actually including P-R intervals, R-P intervals, T-R intervals, and/or R-T intervals, due to oversensing of P-waves and/or T-waves, these potential R-R intervals may be referred to more generally as "intervals" in this document for simplicity. While a large portion of the following description and patient example discussed below describes T-wave oversensing, the same principles apply to P-wave oversensing.

Figure 10:
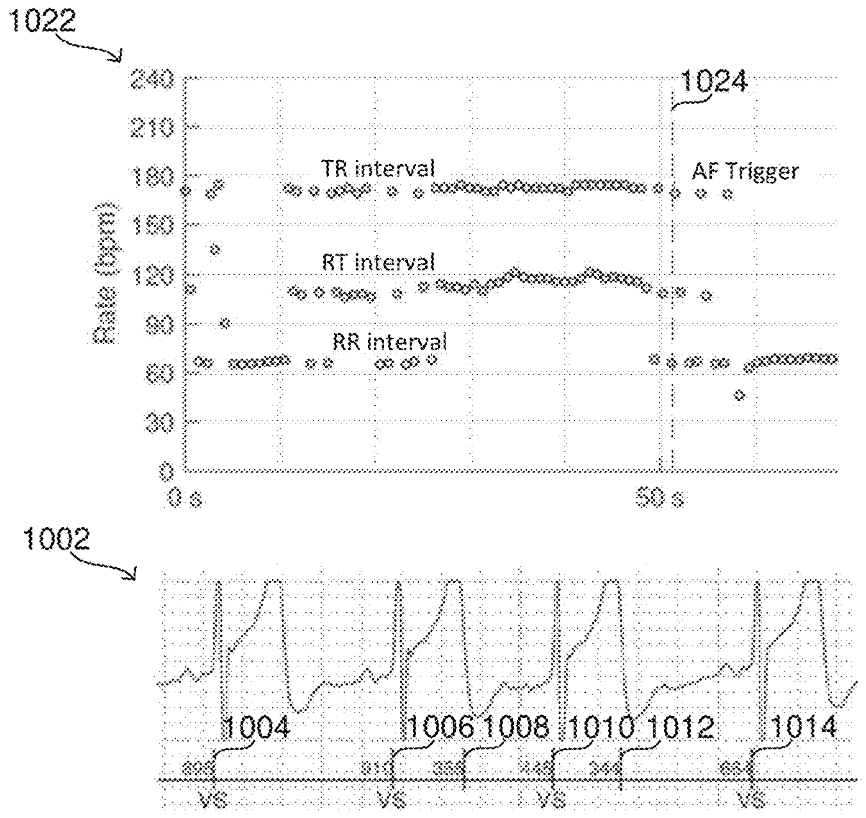
FIG. 10 includes a portion of an EGM segment that resulted in an AF detection due to over-sensed T-waves and includes a graph of HR versus time.

An example of T-wave oversensing is shown if FIG. 10. At the bottom of FIG. 10 is shown a portion of an EGM segment 1002 that resulted in an AF detection due to over-sensed T-waves. At the top of FIG. 10 is shown a graph or plot that includes HR in beats per minute (bpm) along the vertical axis, and time in seconds (s) long the horizontal axis. The dashed vertical line 1024 corresponds to an AF detection occurring at a point in time corresponding to ~52 seconds, and thus, the vertical line 1024 is also marked AF Trigger.

Referring to the portion of the EGM segment 1002 shown at the bottom of FIG. 10, actual R-waves in the EGM segment 1002 that correspond to actual ventricular sensed (VS) events are marked VS. Next to the first vertical line 1004 marked VS is the number 895, referring to an R-R interval of 895 ms. Next to the second vertical line 1006 marked VS is the number 910, referring to an R-R interval of 910 ms. Following the second vertical line 1006 marked VS is another vertical line 1008, which is not marked VS, and actually corresponds to an over-sensed T-wave. Next to the vertical line 1008 is the number 355, referring to an R-T interval of 355 ms. Following the vertical line 1008 is the vertical line 1010 marked VS, which corresponds to a true R-wave. Next to the vertical line 1010 is the number 445, referring to a T-R interval of 455 ms. Following the vertical line 1010 is the vertical line 1012, which corresponds to another over-sensed T-wave. Next to the vertical line 1012 is the number 344, referring to an R-T interval of 344 ms. Following the vertical line 1012 is the vertical line 1014 marked VS, which corresponds to a true R-wave. Next to the vertical line 1014 is the number 664, referring to a T-R interval of 664 ms. In summary, the ordered list of intervals obtained from the portion of the EGM segment 1002 shown at the bottom of FIG. 10 have intervals of: 895 ms, 910 ms, 355 ms, 445 ms, 344 ms, and 664 ms.

Note that the interval between the vertical line labeled 1006 and the vertical line labeled 1010 (both marked VS, and thus corresponding to true R-waves) is 900 ms (i.e., 355 ms+445 ms=900 ms). Also note that the interval between the vertical line labeled 1010 and the vertical line labeled 1014 (both marked VS, and thus corresponding to true R-waves)

is 1008 ms (i.e., 344 ms+664 ms=1008 ms). Accordingly, if the over-sensed T-waves (corresponding to the vertical lines 1008 and 1012) were not detected, then the ordered list of intervals obtained from the portion of the EGM segment 1002 shown at the bottom of FIG. 10 would instead have intervals of: 895 ms, 910 ms, 900 ms, and 1008 ms.

In the example shown in FIG. 10, the true R-R intervals are associated with a HR of approximately 65 bpm. Thus, the true R-R intervals are approximately 923 milliseconds (ms), because 60 sec/min divided by 65 bpm=0.923 seconds=923 ms. However, where there are over-sensed T-waves, every over-sensed T-wave results in two shorter intervals with HRs of approximately 110-120 bpm (R-T intervals) and 170-175 bpm (T-R intervals). For an example, where there is an over-sensed T-wave detected between a pair of true R-waves, rather than the list of intervals including a true R-R interval (having a duration of 873 ms), the list can instead include an R-T interval of approximately 520 ms and a T-R interval of approximately 353 ms.

In accordance with certain embodiments, in order to simplify implementation, techniques for identifying P-wave and/or T-wave oversensing are based on intervals, rather than heart rates. For the following discussion, such techniques focus on a 30 second window preceding an AF trigger. However, it is noted that windows of other (i.e., longer or shorter) lengths can instead be used while still being within the scope of the embodiments described herein. The AF trigger can be detected in various different manners, such as by analyzing heart rate variability and/or R-R interval variability, but is not limited thereto.

Figure 11:
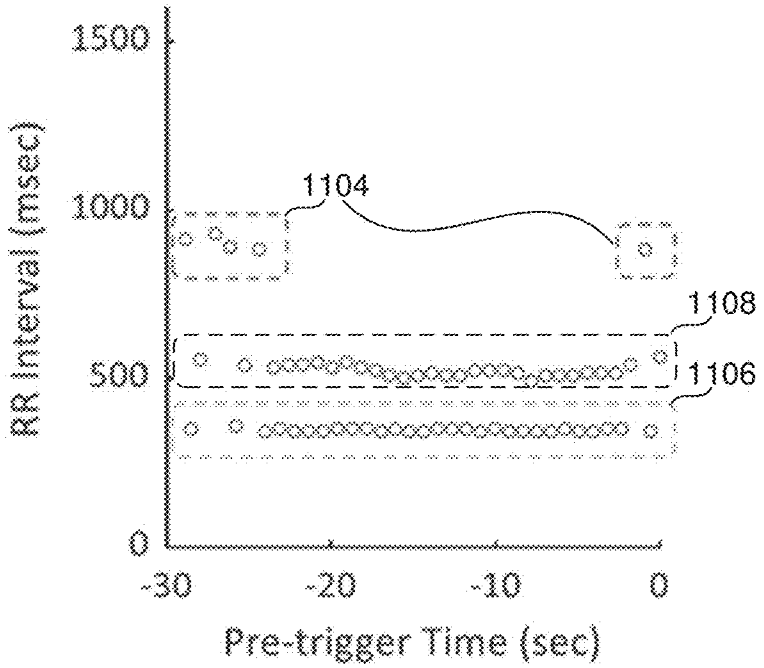
FIG. 11 includes a graph of sensed intervals for a window preceding an AF trigger, which sensed intervals correspond to the inverse of the heart rates shown in FIG. 10.

FIG. 11 illustrates a graph or plot of sensed intervals (in ms) for a 30 ms window preceding an AF trigger, which sensed intervals correspond to the inverse of the heart rates that were shown in FIG. 10. In FIG. 11, the dashed blocks 1104 corresponds to sensed intervals that are true R-R intervals, the dashed block 1106 corresponds to the shorter of the two groups of over-sensed intervals, and the dashed block 1108 corresponds to the longer of the two groups of over-sensed intervals. More specifically, the dashed block 1106 corresponds to R-T intervals, and the dashed block 1108 corresponds to the T-R intervals.

Where a T-wave is mistakenly detected as an R-wave, it can be said that T-wave oversensing occurred, or that an over-sensed R-wave was detected. As can be appreciated from FIGS. 10 and 11, with every over-sensed R-wave (resulted from T-wave oversensing), the true R-R interval is bisected into two shorter intervals, the sum of which is the true R-R interval. Similarly, where a P-wave is mistakenly detected as an R-wave, it can be said that P-wave oversensing occurred, or that an over-sensed R-wave was detected. If P-wave oversensing occurs (instead of T-wave oversensing), with every over-sensed R-wave (resulted from P-wave oversensing), the true R-R interval is also bisected into two shorter intervals, the sum of which is the true R-R interval.

Certain embodiments described herein identify intervals that are not true R-R intervals. In other words, certain embodiments identify false R-R intervals, which can also be referred to as over-sensed R-R intervals. Examples of over-sensed R-R intervals include R-T intervals and T-R intervals, as can be appreciated from the above discussion of FIGS. 10 and 11. Other examples of over-sensed R-R intervals include P-R intervals and R-P intervals.

When attempting to identify over-sensed R-R intervals, it is useful to remove true R-R intervals from the list of intervals being analyzed. This can be accomplished by removing all intervals that are within a specified percentage (e.g., 10%) of the sum of either the immediately preceding two or the immediately following two intervals within the list, as such intervals are likely true R-R intervals with a neighboring over-sensed interval. However, depending on how frequently oversensing occurs, a true R-R may not be neighbored by over-sensed R-waves. Thus, R-R intervals are also classified at true R-R intervals and removed from the list if they are within a specified percentage (e.g., 10%) of the median or mean of the previously-removed "true" R-R intervals. Henceforth, the algorithm will rely only on the remaining intervals that were not removed (i.e., questionable R-R intervals) to identify over-sensed R-R intervals.

For the remaining intervals, oversensing would result in a consistent "short-long-short" alternation. In the case of T-wave oversensing, this pattern corresponds to a short R-T interval (ventricular repolarization time) followed by a slightly longer T-R interval (from ventricular repolarization until the next ventricular depolarization). In the case of P-wave oversensing, this pattern corresponds to a short P-R interval (atrioventricular conduction time) followed by a slightly longer R-P interval (from ventricular depolarization until the next atrial depolarization).

To quantify how often this "short-long-short" pattern occurs, each remaining interval is labeled or classified as either "short" (shorter than the next non-removed interval, which next non-removed interval is longer than the following non-removed interval) or "long" (longer than the next non-removed interval, which next non-removed interval is in turn shorter than the following non-removed interval). In other words, interval (i)<interval (i+1), and interval (i+1) >interval (i+2). Note that both the "short" and "long" intervals are both much shorter than the true R-R interval—they are "short" or "long" relative to each other. However, certain rhythms can also produce a short-long-short pattern by happenstance, such as premature ventricular contractions (PVCs) or AF. Thus, in accordance with certain embodiments, three more discrimination criteria are used to count the number of "short" intervals associated with oversensing. In other words, these discrimination criteria are used to determine whether individual short intervals are over-sensed R-R intervals. Such three additional discrimination criteria, each of which are discussed below, include: short interval variability, short-long interval discrepancy, and short interval duration.

Short Interval Variability—First, during P-wave or T-wave oversensing, the "short" intervals (i.e., P-R interval or R-T interval) should have relatively consistent values, as they depend on either atrioventricular conduction times (P-R) or ventricular repolarization times (R-T). In contrast, the longer intervals (e.g. R-P or T-R) depend on the heart rate, which is much more variable than conduction times or repolarization times. Furthermore, AF or PVCs, which may also demonstrate a "short-long-short" pattern, would result in highly variable "short" interval durations. Therefore, the "short" intervals that truly correspond to oversensing should have low interval-interval variability, quantified by a difference from the previous "short" interval of less than 10%, or some other specified threshold.

Short-Long Interval Discrepancy—The second discrimination criterion serves to discriminate oversensing from R-wave undersensing. During R-wave undersensing, one under-sensed R-wave results in an R-R interval that is similar to the sum of the previous two or next two intervals, effectively appearing as a true R-R interval surrounded by intervals associated with oversensing. However, in the case of undersensing, the "short" and "long" intervals would be almost identical in duration. Therefore, the second discrimination criterion ensures a sufficient discrepancy between the "short" and "long" intervals. Specifically, the "short" intervals that truly correspond to oversensing should differ from the next "long" interval by greater than 5% (or some other specified threshold).

Short Interval Duration—The third discrimination criterion handles the possibility that all of the above criteria could be satisfied by slow, yet variable, heart rates. During true oversensing, however, the "short" intervals should correspond to a very fast heart rate. Thus, the third discrimination criterion requires that the "short" intervals should all have values less 444 ms (i.e., greater than 135 bpm), or some other specified threshold. If the over-sensed R-waves corresponding to these "short" intervals are eliminated, the true R-R intervals can be calculated.

Figure 12:
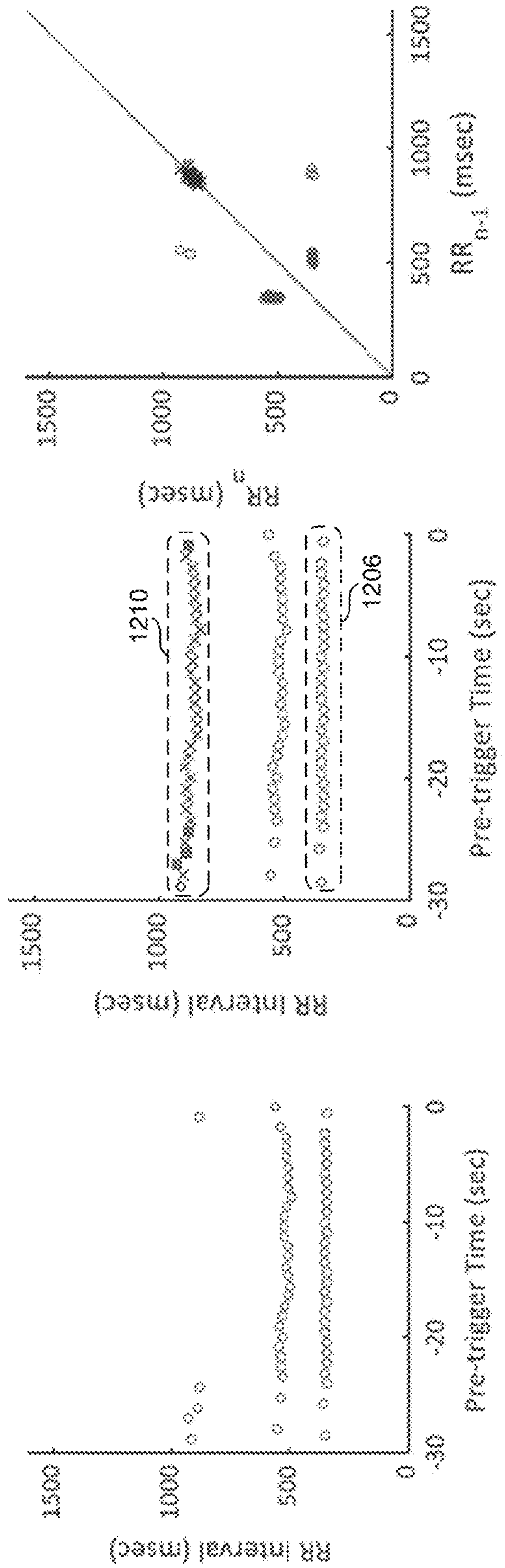
FIG. 12 includes a left panel graph that is the same as FIG. 11, a center panel graph that illustrates how true R-R intervals can be calculated by adding durations of identified R-T and T-R intervals, and a right panel Poincare plot that illustrates actual R-R interval stability after oversensing correction is performed.

FIG. 12 illustrates how certain embodiments can be used to impact the example intervals described with references to FIGS. 10 and 11. The left panel in FIG. 12, which is the same as FIG. 11 discussed above, includes true R-R intervals as well as over-sensed R-R intervals (which include R-T intervals and T-R intervals), as was explained above with reference to FIG. 11. Using embodiments summarized above, and described in additional detail below, the original sensed intervals (shown in the left panel) are corrected by first removing true R-R intervals. Next, the true "short" over-sensed intervals (the lower horizontal line of circles within the dashed block 1206 in the center panel of FIG. 12) are identified. By eliminating the over-sensed R-waves corresponding to these "short" intervals, the true R-R intervals that remain can be calculated, which are shown as Xs within the dashed block 1210 (in the center panel of FIG. 12). More specifically, durations of the true R-R intervals represented by the Xs within the dashed block 1210 (in the center panel of FIG. 12) are calculated by adding (aka summing) the durations of pairs of sensed intervals that include one short interval (an R-T interval) and one long interval (a T-R interval). Note that calculated (aka corrected) R-R intervals in the center panel in FIG. 12 are consistent with the previously identified and removed true R-R intervals. The Poincare plot (shown in the right panel in FIG. 12) plots the relationship between each interval and the immediately preceding interval, showing the same data and markers as the center panel. This Poincare plot illustrates the actual R-R interval stability (Xs), after oversensing correction of the original R-R intervals (circles) is performed. Before oversensing correction, each interval differs, albeit predictably, from the preceding interval. After oversensing correction, all the interval-interval difference is negligible (overlapping Xs).

Additional and alternative details of the embodiments of the present technology, introduced above, are described below with reference to FIGS. 13A, 13B, and 13C, which can be referred to collectively as FIGS. 13A-13C, or even more succinctly as FIG. 13.

Figure 13A:
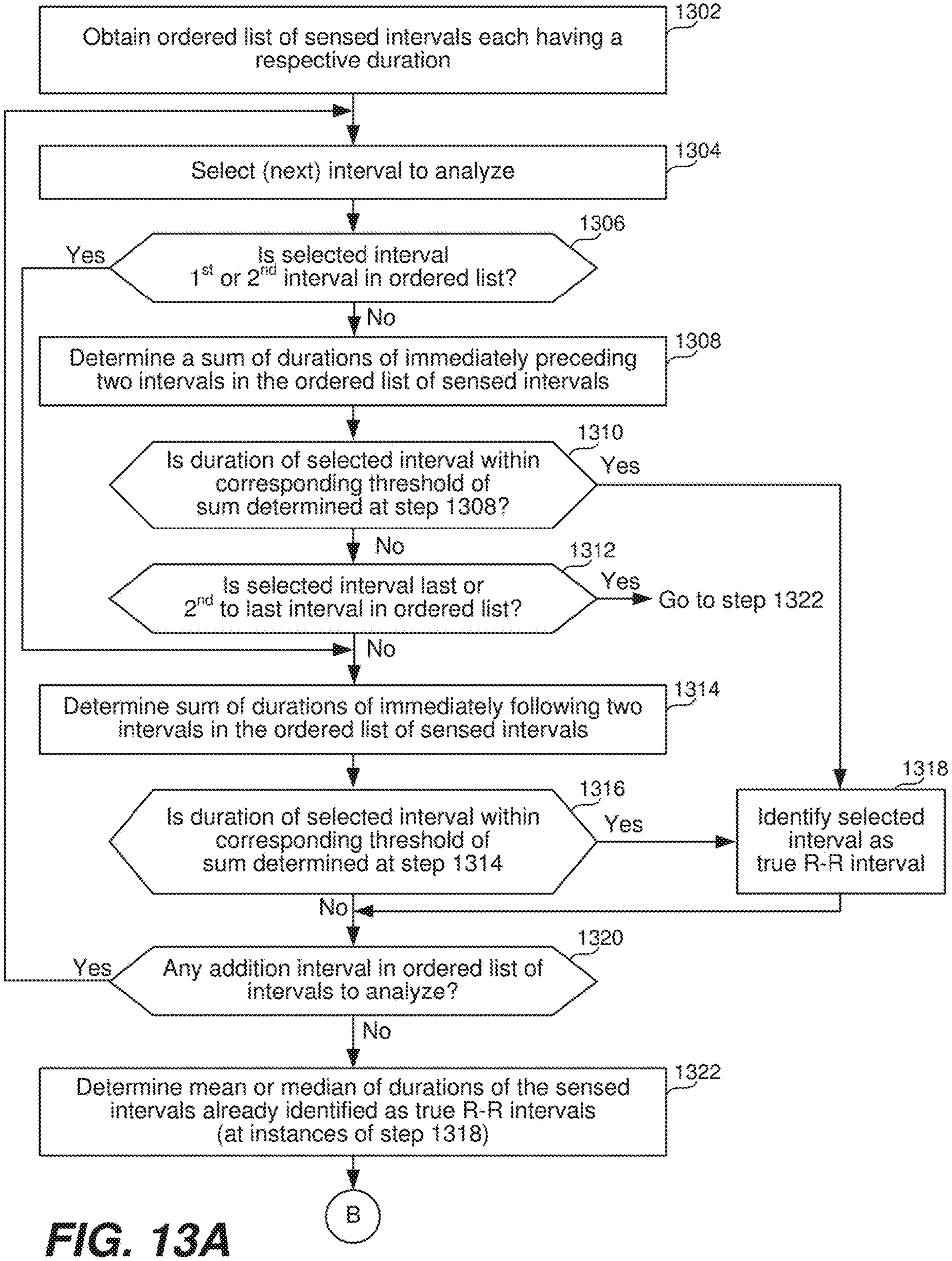
FIGS. 13A, 13B, and 13C, which can be collectively referred to as FIG. 13, includes a high level flow diagram that is used to describe how true R-R intervals can be distinguished from over-sensed R-R intervals, and how an oversensing score can be determined and used to reject an AF detection.
Figure 13B:
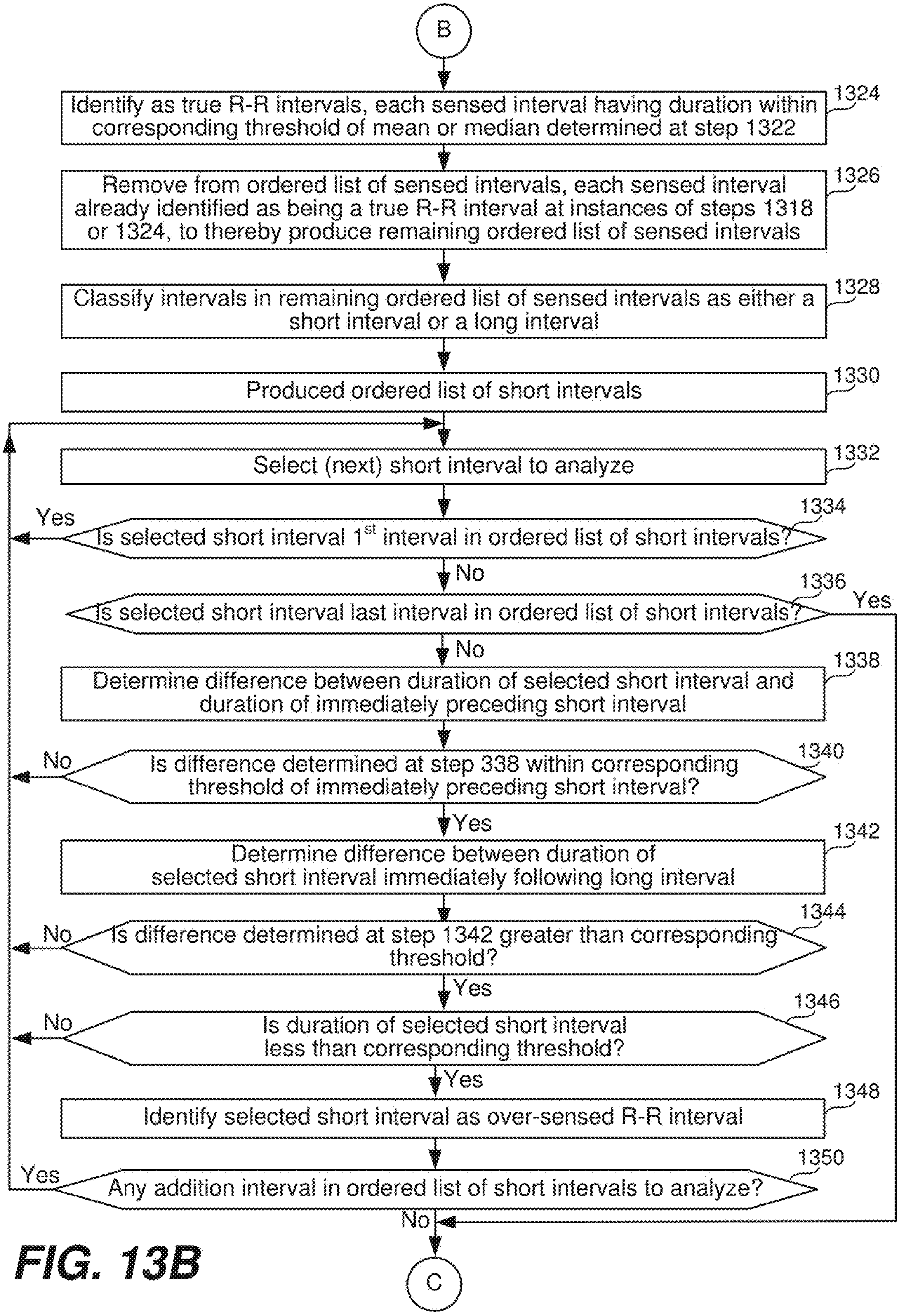

Referring to FIG. 13A, step 1302 involves obtaining an ordered list of intervals that each have a respective duration. The ordered list of intervals, obtained at step 1302, would preferably include only true R-R intervals. However, due to T-wave and/or P-wave oversensing, the ordered list of intervals obtained at step 1302 would likely also include one or more over-sensed R-R intervals. In accordance with certain embodiments, the ordered list of sensed intervals is obtained by sensing or otherwise obtaining an EGM or ECG segment corresponding to a period of time preceding and leading up to an AF episode that was detected, identifying potential R-waves within the EGM or ECG segment, and determining intervals between consecutive ones of the potential R-waves to thereby produce the ordered list of sensed intervals. Such potential R-waves can be identified within the EGM or ECG segment by comparing the EGM segment, or samples thereof, to an R-wave sensing threshold, and identifying potential R-waves when the R-wave sensing threshold is reached or exceeded. Other variations are also possible and within the scope of the embodiments described herein.

Step 1304 involves selecting an interval (from the ordered list of intervals obtained at step 1302) to analyze. The first time step 1304 is performed (for an ordered list of intervals), the first interval in the ordered list is selected. The second time step 1304 is performed (for the ordered list of intervals), the second interval in the ordered list is selected, and so on.

At step 1306 there is a determination of whether the interval (selected for analysis at step 1304) is the first or second interval in the ordered list of intervals. If the selected interval is the first or second interval (i.e., if the answer to the determination at step 1306 is Yes), then flow goes to step 1314 (thereby skipping steps 1308, 1310, and 1312). If the selected interval is not the first or second interval (i.e., if the answer to the determination at step 1306 is No), then flow goes to step 1308.

Step 1308 involves determining a sum of the durations of the immediately preceding two intervals in the ordered list of sensed intervals. At step 1310 there is a determination of whether the duration of the selected interval is within a corresponding threshold (e.g., within 10%) of the sum determined at step 1308. If the duration of the selected interval is within the corresponding threshold (e.g., within 10%) of the sum determined at step 1308 (i.e., if the answer to the determination at step 1310 is Yes), then flow goes to step 1318, and the selected interval is identified (aka classified) as a true R-R interval. If the duration of the selected interval is not within the corresponding threshold (e.g., within 10%) of the sum determined at step 1308 (i.e., if the answer to the determination at step 1310 is No), then flow goes to step 1312.

At step 1312 there is a determination of whether the selected interval is the last or second to last interval in the ordered list of sensed intervals. If the selected interval is the last or second to last interval (i.e., if the answer to the determination at step 1312 is Yes), then flow goes to step 1322 (thereby skipping steps 1314, 1316, and 1320). If the selected interval is not the last or second to last interval (i.e., if the answer to the determination at step 1312 is No), then flow goes to step 1314.

Step 1314 involves determining the sum of the durations of the immediately following two intervals in the ordered list of intervals. At step 1316 there is a determination of whether the duration of the selected interval is within a corresponding threshold (e.g., within 10%) of the sum determined at step 1314. If the duration of the selected interval is within a corresponding threshold (e.g., within 10%) of the sum determined at step 1314 (i.e., if the answer to the determination at step 1316 is Yes), then flow goes to step 1318, and the selected interval is identified (aka classified) as a true R-R interval. If the duration of the selected interval is not within the corresponding threshold (e.g., within 10%) of the sum determined at step 1314 (i.e., if the answer to the determination at step 1316 is No), then flow goes to step 1320.

At step 1320 there is a determination of whether there is at least one additional interval (in the ordered list of sensed intervals) to analyze. If the answer to the determination at step 1320 is Yes, then flow returns to step 1304 where the next interval (in the ordered list of sensed intervals) is selected for analysis. If the answer to the determination at step 1320 is No, then flow goes to step 1322, which is discussed below.

Steps 1304-1320, summarized above, are used to remove true R-R intervals from the ordered list of intervals being analyzed, which is accomplished by removing all intervals that are within a corresponding threshold (e.g., 10%) of the sum of the immediately preceding two intervals within the list, or that are within a corresponding threshold (e.g., 10%) of the sum of the immediately following two intervals within the list, as such intervals are likely true R-R intervals with a neighboring over-sensed R-R interval. While it is likely that the same threshold (e.g., 10%) is used at both step 1310 and step 1316, that need not be the case. The threshold used at step 1310 and/or 1316 can be a percentage, such as 10%, or some higher or lower percentage. Alternatively, the threshold used at step 1310 and/or 1316 can be a specified value, e.g., 80 milliseconds (ms), or some higher or lower value. Other variations are also possible, and within the scope of the embodiments described herein.

Returning to the discussion of step 1322, step 1322 involves determining a mean or median of the durations of the sensed intervals already identified as true R-R intervals (at instances of steps 1318). Accordingly, at step 1322 a likely duration of true R-R intervals is determined. Flow then goes to step 1324 in FIG. 13B. Step 1324 involves identifying (aka classifying) as a true R-R interval, each sensed interval (in the remaining ordered list of sensed intervals) that has a duration that is within a corresponding threshold (e.g., 10%) of the mean or median determined at step 1322. Thus, R-R intervals are also identified as true R-R intervals if they are within a corresponding threshold (e.g., 10%) of the mean or median of the previously identified true R-R intervals. The threshold used at step 1324 can be a percentage, such as 10%, or some higher or lower percentage. Alternatively, the threshold used at step 1324 can be a specified value, e.g., 80 milliseconds (ms), or some higher or lower value. Other variations are also possible, and within the scope of the embodiments described herein. It can be appreciated from the description herein that the terms "identified" and "classified", and the terms "identify" and "classify", are often referred to interchangeably herein.

Step 1326 involves removing from the ordered list of sensed intervals, each sensed interval that was already identified as being a true R-R interval at an instance of step 1318 or 1324, to thereby produce a remaining ordered list of sensed intervals. Step 1328 then involves classifying (aka identifying) intervals in the remaining ordered list of intervals as either a short interval or a long interval. For an example, an interval (in the remaining ordered list of sensed intervals) can be classified as a short interval when a duration of the interval is shorter than an immediately following interval in the remaining ordered list of sensed intervals; and an interval (in the remaining ordered list of sensed intervals) can be classified as a long interval when a duration of the interval is longer than an immediately following interval in the remaining ordered list of sensed intervals. Other ways of classifying intervals as short or long intervals are also possible and within the scope of the embodiments described herein. For example, rather than (or in addition to) comparing a duration of an interval to the duration of the following interval, the duration of the interval can be compared to the duration of the preceding interval. In certain embodiments, the first and/or last interval (in the remaining ordered list of sensed intervals) is removed or ignored.

Step 1330 involves producing an ordered list of the short intervals. This can be accomplished, for example, by removing all the long intervals (identified at step 1328) from the remaining ordered list of sensed intervals (produced at step 1326). This can alternatively be accomplished by creating a new ordered list that just includes the short intervals identified at step 1328. Other variations are also possible and within the scope of the embodiments described herein.

Step 1332 involves selecting an interval (from the ordered list of short intervals produced at step 1330) to analyze. The first time step 1332 is performed (for an ordered list of short intervals), the first interval in the ordered list is selected. The second time step 1332 is performed (for the ordered list of short intervals), the second interval in the ordered list is selected, and so on.

At step 1334 there is a determination of whether the interval (selected for analysis at step 1332) is the first interval in the ordered list of short intervals. If the selected interval is the first interval (i.e., if the answer to the determination at step 1334 is Yes), then flow goes back to step 1332 and the next interval is selected for analysis. If the selected interval is not the first interval (i.e., if the answer to the determination at step 1334 is No), then flow goes to step 1336.

At step 1336 there is a determination of whether the interval (selected for analysis at step 1332) is the last interval in the ordered list of short intervals. If the selected interval is the last interval (i.e., if the answer to the determination at step 1336 is Yes), then flow skips to step 1352. If the selected interval is not the last interval (i.e., if the answer to the determination at step 1336 is No), then flow goes to step 1338.

Step 1338 involves determining a difference between the duration of the selected short interval and the duration of the immediately preceding short interval. At step 1340 there is a determination of whether the difference determined at step 1338 is within a corresponding threshold (e.g., 10%) of the immediately preceding short interval. If the answer to the determination at step 1340 is No, then flow returns to step 1332 where the next short interval to analyze is selected. If the answer to the determination at step 1340 is Yes, then flow goes to step 1342. Steps 1338 and 1340 are used to test the short interval variability criteria, because the "short" intervals that truly correspond to oversensing (i.e., that are over-sensed R-R intervals) should have low interval-interval variability, e.g., quantified by a difference from the previous "short" interval of less than 10% or some other specified threshold.

Step 1342 involves determining a difference between the duration of the selected short interval and the duration of the immediately following long interval. At step 1344 there is a determination of whether the difference determined at step 1342 is greater than a corresponding threshold (e.g., 5%) of the immediately following long interval. If the answer to the determination at step 1344 is No, then flow returns to step 1332 where the next short interval to analyze is selected. If the answer to the determination at step 1344 is Yes, then flow goes to step 1346. The threshold used at step 1344 can be a percentage, such as 5%, or some higher or lower percentage. Alternatively, the threshold used at step 1346 can be a specified value, e.g., 20 milliseconds (ms), or some higher or lower value. Other variations are also possible, and within the scope of the embodiments described herein. Steps 1342 and 1344 are used to test the short-long interval discrepancy, because a short interval that truly correspond to oversensing should differ from the next long interval by more than 5% or some other specified threshold.

Step 1346 involves determining whether the duration of the selected short interval is less than a corresponding threshold, e.g., 444 ms (i.e., greater than 135 bpm). If the answer to the determination at step 1346 is No, then flow returns to step 1332 where the next short interval to analyze is selected. If the answer to the determination at step 1346 is Yes, then flow goes to step 1348. Step 1346 is used to test the short interval duration, which handles the possibility that all of the above criteria could be satisfied by slow, yet variable, heart rates. During true oversensing, a short interval should correspond to a very fast heart rate, which is tested for at step 1346.

At step 1348 the short interval (for which the answers to the determinations at step 1340, 1344, and 1346 were all Yes) is identified (aka classified) as an over-sensed R-R interval. This is because the interval satisfied the short interval variability criteria, the short-long interval discrepancy criteria, and the short interval duration criteria, which were discussed above.

At step 1350 there is a determination of whether there is at least one additional short interval (in the ordered list of short intervals) to analyze. If the answer to the determination at step 1350 is Yes, then flow returns to step 1332 where the next short interval (in the ordered list of short intervals) is selected for analysis. If the answer to the determination at step 1350 is No, then flow goes to step 1352 in FIG. 13C, which is discussed below.

Figure 13C:
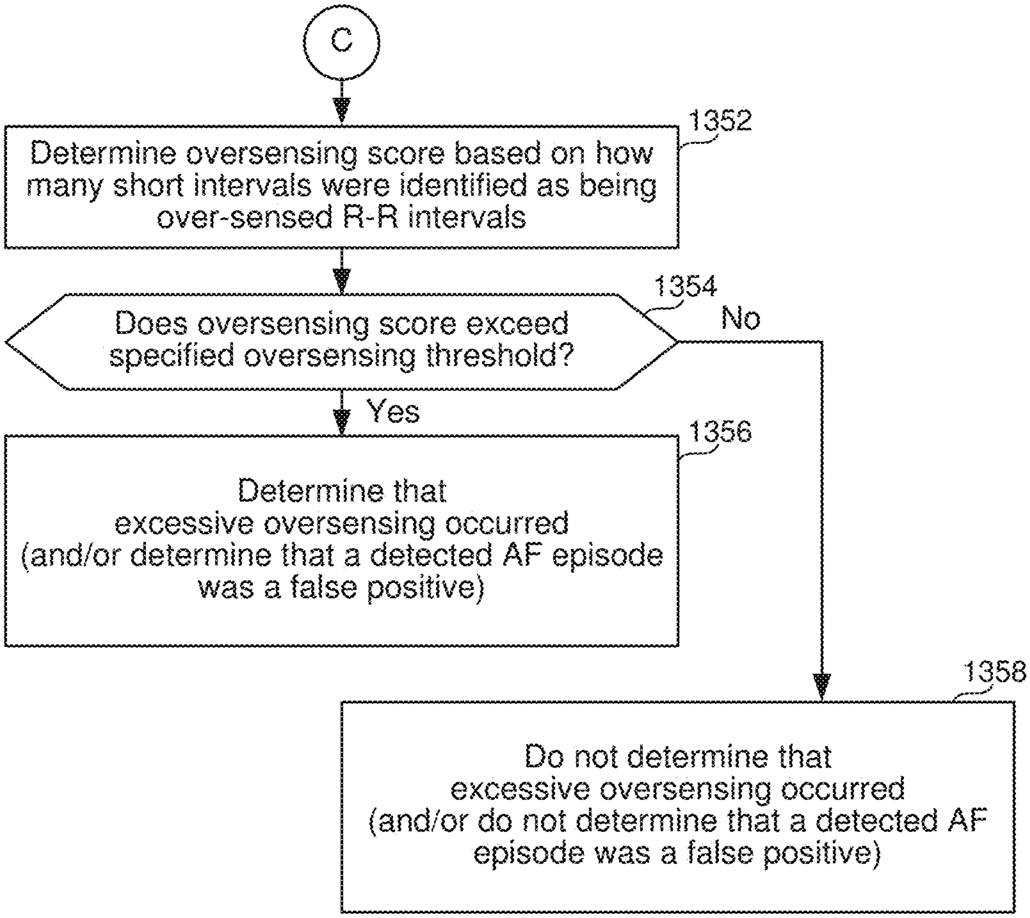

Referring to FIG. 13C, step 1352 involves determining an oversensing score based on how many short intervals were identified as being over-sensed R-R intervals (at instances of step 1348). In accordance with certain embodiments, the oversensing score is determined by determining what percentage of all of the sensed intervals classified as a short interval were identified as being an over-sensed R-R interval. Another way to calculate the oversensing score is using the equation Oversensing Score (OS)=2×[the total number of sensed intervals classified as a short interval that were identified as being an over-sensed R-R interval][total number of all intervals]. The factor of "2" in this equation accounts for the fact that each "short" interval also has a paired "long" interval, so it should count as 2 of the total intervals when calculating a percent. In other words, both intervals associated with (i.e., before and after) an over-sensed P- or T-wave are counted. Other variations are also possible and within the scope of the embodiments described herein.

At step 1354 there is a determination of whether the oversensing score (determined at step 1352) exceeds a corresponding threshold (e.g., 50%). If the oversensing score exceeds the corresponding threshold (e.g., if more than 50% of the short intervals were classified as being over-sensed intervals), then flow goes to step 1356. At step 1356 there is a determination or conclusion that excessive over-sensing had occurred. Such a determination or conclusion can be used to determine that a detected AF episode that was detected based on the sensed intervals was a false positive. If the oversensing score does not exceed the corresponding threshold (e.g., if less than 50% of the short intervals were classified as being over-sensed intervals), then flow goes to step 1358, and there is no conclusion or determination that excessive oversensing occurred.

In accordance with certain embodiments, an IMD may perform the method described above with reference to FIG. 13 in response to an AF episode being detected. The detection of an AF episode can also be referred to as an AF trigger. Such an IMD may be configured to transmit, to an external device that is communicatively coupled to a patient care network, data corresponding to an AF episode that is detected by the IMD. In certain such embodiments, the IMD does not (is prevented from) transmitting (to the external device that is communicatively coupled to the patient care network) data corresponding to an AF episode that is detected by the IMD, but is thereafter determined by the IMD as being a false positive detection.

In accordance with certain embodiments, the medical device (e.g., IMD) that performs the method described above with reference to FIG. 13 may monitor the HR of a patient based on intervals identified from a segment of an EGM or ECG, and the medical device can determine based on the results of the method whether a monitored HR is inaccurate due to oversensing and thus should be ignored or recalculated. For an example, if an oversensing score exceeds a corresponding threshold, the medical device can conclude that a HR that was determined based on sensed interval is inaccurate and should not be used, or should be recalculated.

In accordance with certain embodiments, after identifying true R-R intervals (e.g., at instances of steps 1318 and/or 1324) and identifying (aka classifying) individual over-sensed R-R intervals short or long intervals, pairs of over-sensed R-R intervals can be combined to identify further true R-R intervals. For example, a short interval (e.g., R-T interval) and a following long interval (e.g., T-R interval) can be summed to produce a calculated true R-R interval. For another example, adjacent R-P and P-R intervals can be summed to produce a calculated true R-R interval. A corrected ordered list of sensed intervals can then be produced that includes the true R-R intervals (e.g., identified at instances of steps 1318 and/or 1324) and the further true R-R intervals identified by summing appropriate pairs of over-sensed R-R intervals. HR monitoring and/or monitoring for an arrhythmic episode can then be based on the corrected ordered list of sensed intervals.

R-R Intervals Include Regularly Irregular Repeated Pattern

As noted a few times above, a common technique for detecting AF is based on measures of R-R interval variability. However, relying solely on R-R interval variability for detecting AF can lead to many false positive AF detections. This is because relying solely on R-R interval variability will not detect regularly irregular patterns of R-R intervals that are not indicative of AF, but rather, may result if multiple atrial foci of activity take turns activating the ventricles.

As briefly discussed above with reference to step 216 in FIG. 2, a time-based AF discriminator can be used to detect regularly irregular R-R interval patterns, if present, and based thereon, can determine whether to classify an AF detection as a false positive detection. Details of such a time-based AF discriminator are described below with reference to FIGS. 14-17. As will be described in additional detail below, such embodiments provide for improved AF discrimination by distinguishing between regularly irregular patterns of R-R intervals, which are not indicative of AF, and irregularly irregular patterns that are indeed indicative of AF. Beneficially, such embodiments can be used to reduce false positive AF detections and thereby increase the specificity of AF detections.

An ordered list of R-R intervals within a window leading up to a detection of an AF episode is obtained, wherein each of the R-R intervals has a respective duration. The AF episode, which can also be referred to as an AF trigger or AF detection, may occur because R-R interval variability exceeded a specified threshold for at least a specified period of time, and/or using some other technique for detecting AF episodes. Such a window can be defined, for example, as a specified number N of R-R intervals leading up to the detection of the AF episode. Such a window can alternatively be defined, for example, as a specified number N of seconds leading up to the detection of the AF episode. For more specific examples, N can equal thirty (30), in which case the aforementioned window can include thirty R-R intervals leading up to the AF detection, or the R-R intervals within a thirty second window leading up to the AF detection. The use of smaller or larger values for N are also within the scope of the embodiments described herein.

In certain embodiments, a measure of a dominant repeated R-R interval pattern within the window is determined and compared to pattern threshold. If the measure of the dominant repeated R-R interval pattern is below the pattern threshold, then it is determined that the AF detection does not correspond to an actual AF episode. Conversely, if the measure of the dominant repeated R-R interval pattern is above the pattern threshold, then there is an increased level of confidence that the detected AF episode corresponded to an actual AF episode, i.e., there is an increased level of confidence that the detected AF episode corresponds to a true positive detection.

Figure 14:
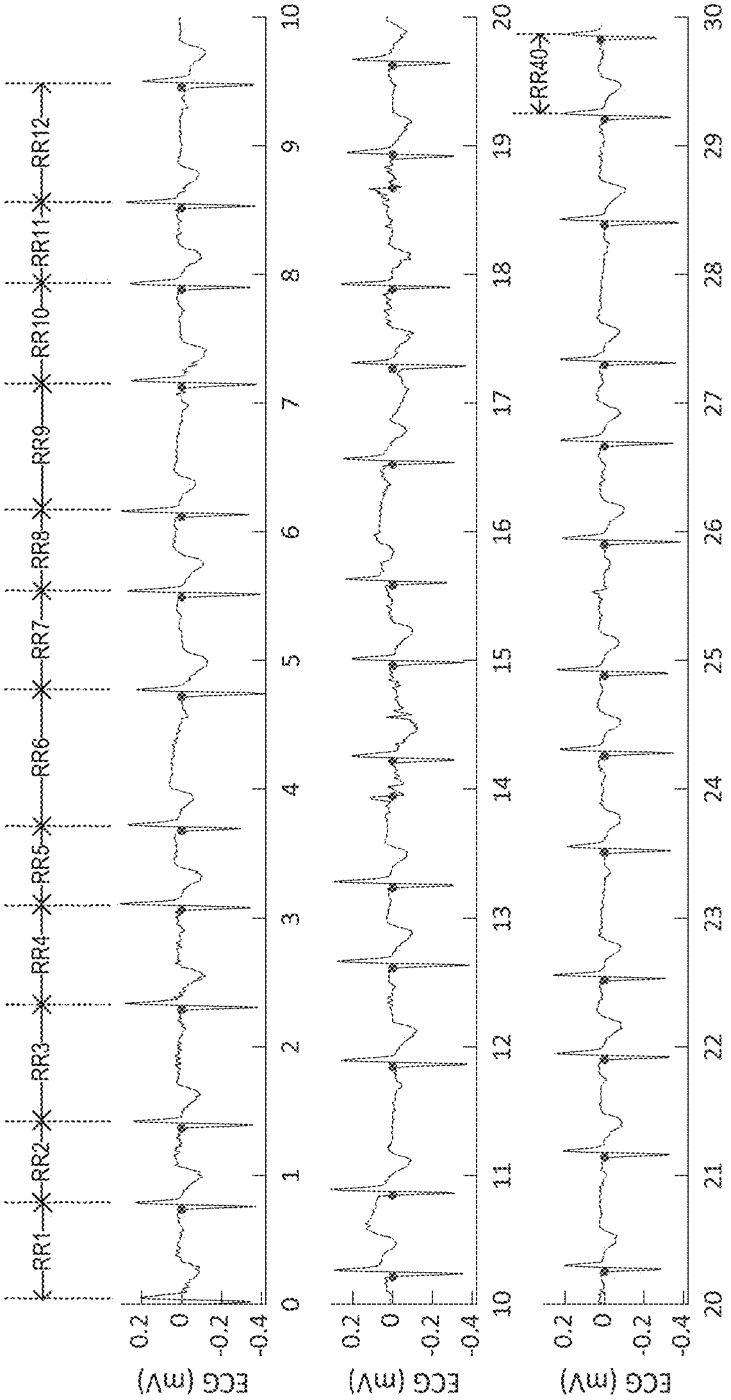
FIG. 14 includes an example an EGM segment within a thirty-second window leading up to a detection of an AF episode.

FIG. 14 includes an example an EGM segment within a thirty (30) second window leading up to a detection of an AF episode, wherein there are forty (40) R-R intervals within the window. A detection of an AF episode may also be referred to herein as an AF detection, an AF trigger, or the like. In order to fit the EGM segment on a single page, the EGM segment in FIG. 14 is separated into three separate ten second panels that are shown one above the other. Example R-R intervals are labeled within FIG. 14. The R-R intervals within the top one of the three ten second panels are labeled RR1, RR2, RR3, . . . RR12, wherein RR1 corresponds to the R-R interval number 1, the RR2 corresponds to the R-R interval number 2, the RR3 corresponds to the RR interval number 3, . . . RR2 corresponds to the R-R interval number 12. Except for the RR40, which corresponds to the R-R interval number 40, the R-R intervals in the other two ten second panels are not labeled so as to minimize clutter in FIG. 14.

The table in FIG. 15 incudes a list of the forty R-R intervals within the thirty-second window shown in FIG. 14. What is shown in the rightmost column in FIG. 15 is an example of an ordered list of R-R intervals within a window leading up to a detection of an AF episode, wherein each of the R-R intervals has a respective duration. Referring to FIG. 15, the duration for the RR1 is 734.4 milliseconds (ms), the duration of the RR2 is 632.8 ms, the duration of the RR3 is 921.9 ms, . . . the duration of the RR40 is 625.0. As can be appreciated from FIG. 15, the minimum R-R interval duration shown therein is 275.8 ms, and the maximum R-R interval duration shown therein is 1085.9 ms. It can be appreciated from FIG. 15 that there is very high R-R interval variability, which is what led to the detection of the AF episode.

Figure 16:
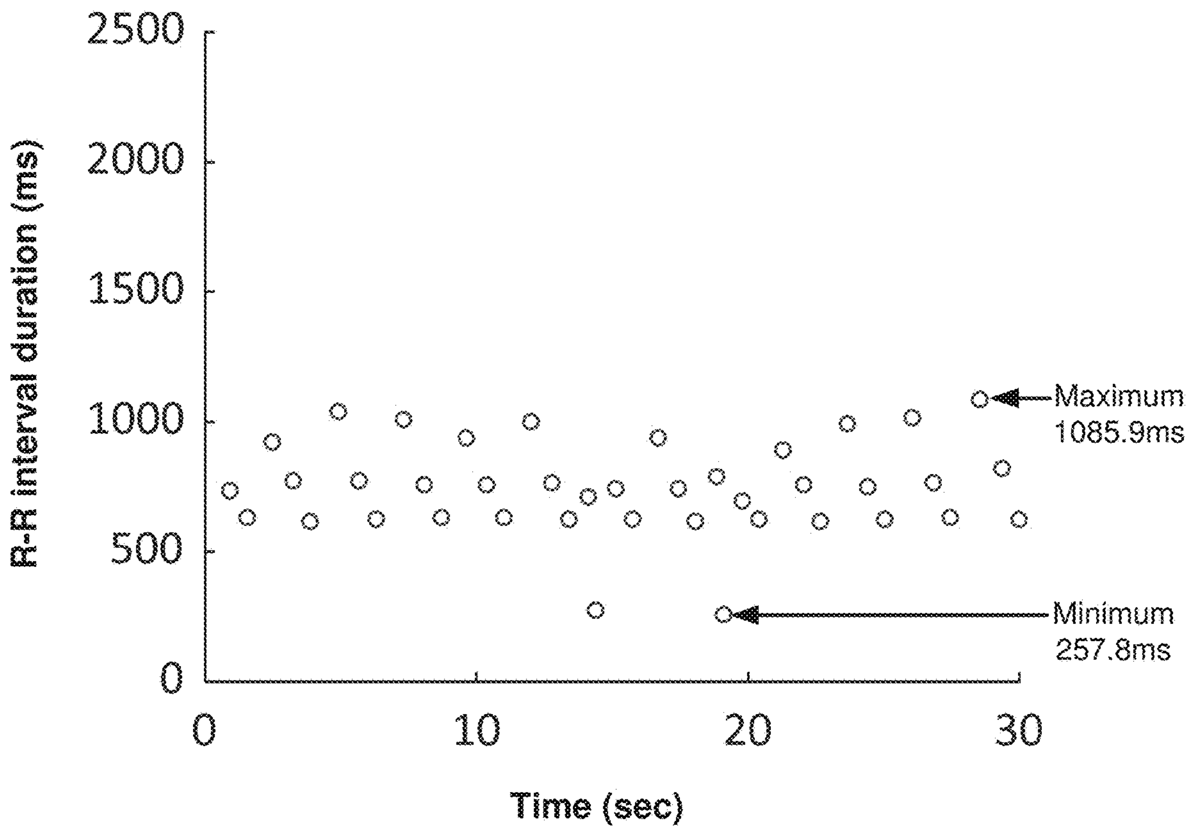
FIG. 16 is a graph showing the forty R-R intervals (within the thirty-second window shown in FIG. 14 and listed in the table in FIG. 15) versus time.

FIG. 16 is a graph showing the forty R-R intervals (within the thirty-second window shown in FIG. 14 and listed in the table in FIG. 15) versus time. The minimum R-R interval duration (275.8 ms) and the maximum R-R interval duration (1085.9 ms) are pointed to by arrows, as was also the case in FIG. 15. It can also be appreciated from FIG. 16 that there is very high R-R interval variability, which is what led to the detection of the AF episode.

In accordance with certain embodiments of the present technology, an ordered list of R-R intervals within a window leading up to a detection of an AF episode is obtained and analyzed to determine whether there is regularly irregular pattern hidden therein, which is indicative of the detection of an AF episode being a false positive detection. More specifically, in certain embodiments, in order to determine whether a regularly irregular pattern of R-R intervals is present within the window, pairwise differences are determined between pairs of R-R intervals that are one interval apart, two intervals apart, three intervals apart, . . . and M intervals apart. This results in M sets of pairwise differences. For example, assuming there are forty R-R intervals within the window being analyzed (as was the case in the example widow described above with reference to FIGS. 14 and 15), the $1^{st}$ set of pairwise differences can include the difference between the $1^{st}$ and $2^{nd}$ R-R intervals, the difference between the $2^{nd}$ and $3^{rd}$ R-R intervals, the difference between the $3^{rd}$ and $4^{th}$ RR-intervals, . . . the difference between the $39^{th}$ and $40^{th}$ R-R intervals. The $2^{nd}$ set of pairwise differences can include the difference between the $1^{st}$ and $3^{rd}$ R-R intervals, the difference between the $2^{nd}$ and $4^{th}$ R-R intervals, the difference between the $3^{rd}$ and $5^{th}$ RR-intervals, . . . the difference between the $38^{th}$ and $40^{th}$ R-R intervals. The $3^{rd}$ set of pairwise differences can include the difference between the $1^{st}$ and $4^{th}$ R-R intervals, the difference between the $2^{nd}$ and $5^{th}$ R-R intervals, the difference between the $3^{rd}$ and $6^{th}$ RR-intervals, . . . the difference between the $37^{th}$ and $40^{th}$ R-R intervals. The $M^{th}$ set of pairwise differences can include the difference between the $1^{st}$ and Mth R-R intervals, the difference between the $2^{nd}$ and $(m+1)^{th}$ R-R intervals, the difference between the $3^{rd}$ and $(M+2)^{th}$ RR-intervals, . . . the difference between the $(40-M)^{th}$ and $40^{th}$ R-R intervals. For each set of pairwise intervals, of the M sets of pairwise intervals, a median (or an indicator of the median) of the set is determined, wherein a relatively low median (or indicator thereof) is indicative of there being a hidden pattern (most likely meaning that AF did not occur), and relative high median (or indicator thereof) is indicative of there being no regular irregular pattern (most likely meaning that AF actually did occur). In certain embodiments, the minimum median (or indicator thereof) for the M sets is identified and compared to a pattern threshold, wherein the minimum median (or indicator thereof) is an example of a measure of the dominant repeated pattern within the window. If the minimum median (or indicator thereof) is below the pattern threshold, then it is determined that the detection of the AF episode does not correspond to an actual AF episode. Conversely, if the minimum median (or indicator thereof) is above the pattern threshold, then there is an increased level of confidence that the detected AF episode corresponded to an actual AF episode, i.e., there in increased level of confidence that the detected AF episode corresponds to a true positive detection. Additional details of the embodiments summarized above are described below with reference to the high level flow diagram in FIG. 17A.

Figure 17A:
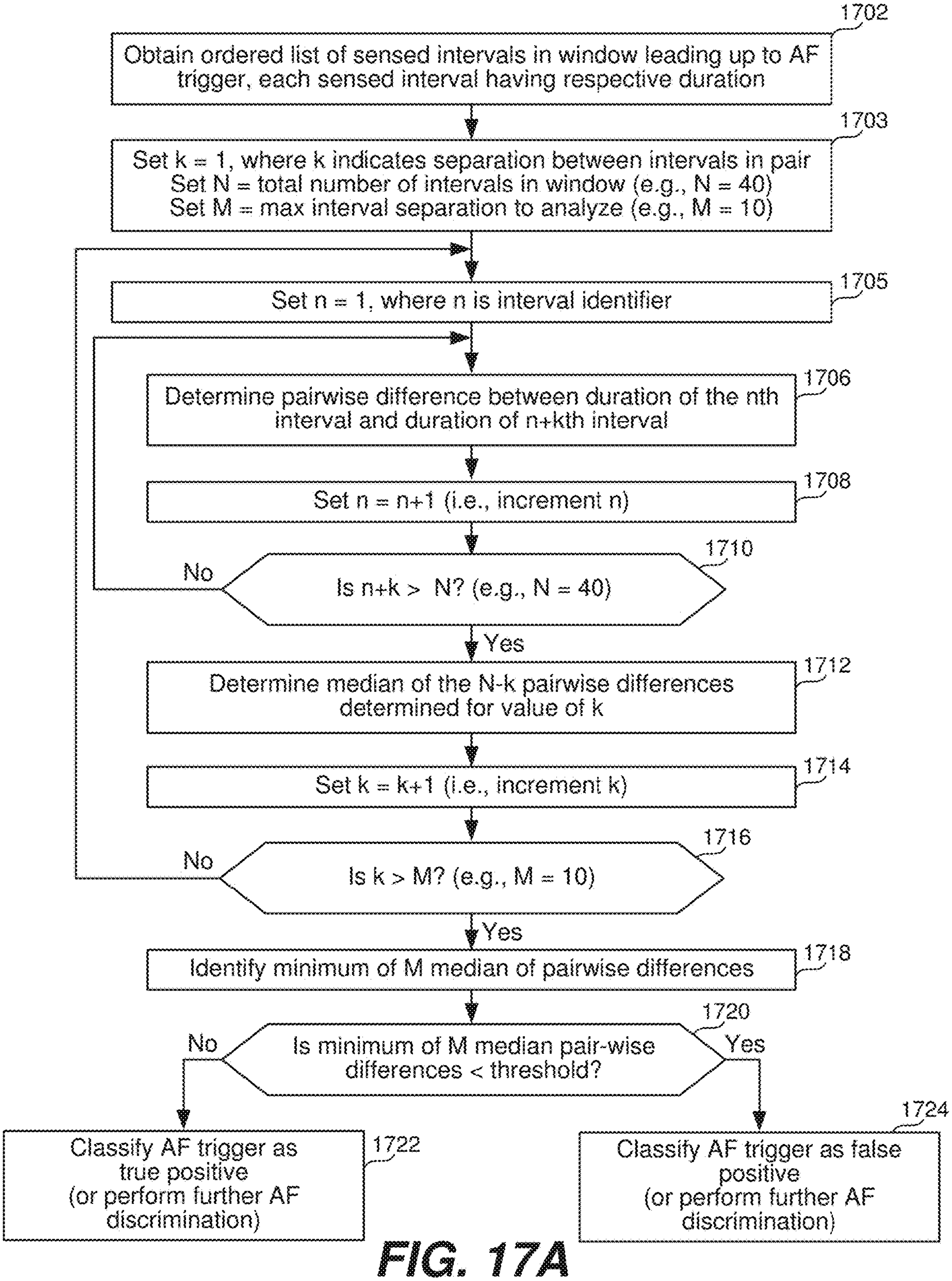
FIGS. 17A, 17B, and 17C, which can be collectively referred to as FIG. 17, are high level flow diagrams used to summarize various different methods of improving AF detection specificity by determining whether a regularly irregular R-R interval pattern is present within a portion of an EGM or ECG.

Referring to FIG. 17A, step 1702 involves obtaining an ordered list of R-R intervals within a window leading up to a detection of an AF episode, wherein each of the R-R intervals has a respective duration. The ordered list of R-R intervals can be obtained, for example, by identifying R-waves within an EGM or ECG segment, and determining intervals between consecutive ones of the R-waves to thereby produce the ordered list of R-R intervals. Such R-waves can be identified within the EGM or ECG segment by comparing the EGM or ECG segment, or samples thereof, to an R-wave sensing threshold, and identifying R-waves when the R-wave sensing threshold is reached or exceeded. Other variations are also possible and within the scope of the embodiments described herein. For example, R-waves can alternatively or additionally be identified using R-wave or QRS complex morphology templates.

An example of the ordered list of R-R interval within a window leading up to a detection of an AF episode is shown in FIG. 15, as noted above. The ordered list of R-R intervals, obtained at step 1702, would preferably include only true R-R intervals. However, due to T-wave and/or P-wave oversensing, the ordered list of intervals obtained at step 1702 may also include one or more over-sensed R-R intervals. In other words, the ordered list of R-R intervals, included in the window leading up to the detection of the AF episode (aka an "AF trigger"), in addition to including true R-R intervals, may also include one or more over-sensed R-R intervals that may be present, e.g., if one or more P-waves and/or T-waves are mistakenly identified as R-waves. In order to maximize the specificity of the methods summarized with reference to FIG. 17A, one or more techniques for identifying and removing over-sensed R-R intervals can be performed prior to step 1702, as part of step 1702, or between step 1702 and the next step 1703.

Still referring to FIG. 17A, at step 1703 the values of various variables are specified. More specifically, at step 1703 there is a setting of k=1, where k indicates the separation between R-R intervals in a pair of R-R intervals. Further, a value for N is specified, wherein N is the total number of R-R intervals within the window leading up to the detection of the AF episode. In the example discussed above with reference to FIGS. 14 and 15, N=40. Additionally, at step 1703 M is set to the maximum interval separation that is to be analyzed. In accordance with certain embodiments, M is an integer that is at least equal to 17. In certain examples described herein, M is set to 10, i.e., M=10 in such examples.

Step 1703 involves setting n=1, where n is an interval identifier.

Step 1706 involves determining a pairwise difference between the duration of the nth interval and the duration of the n+$k^{th}$ interval. Presuming n=1 and k=1 the first time that step 1706 is performed, then step 1706 involves determining the pairwise difference between the duration of the $1^{st}$ interval and the duration of the $2^{nd}$ interval.

At step 1708 the value for n is incremented by setting n=n+1. Thus, the first time step 1708 is performed, n=1+1, thereby setting n=2.

At step 1710 there is a determination of whether n+k is greater than to N. Presuming N=40, the first time that step 1710 is performed n+k will equal 3, which is less than N (i.e., is less than 40), resulting in the answer to the determination at step 1710 being No. If the answer to the determination at step 1710 is No, the flow returns to step 1706. This will result in N−k pairwise differences being determined before the answer to the determination at step 1710 is eventual Yes, at which point flow goes to step 1712. Accordingly, for n=1, the iterations of steps 1706-1710 will result in a pairwise difference between the $1^{st}$ and $2^{nd}$ R-R intervals, a pairwise difference between the $2^{nd}$ and $3^{rd}$ R-R intervals, a pairwise difference between $3^{rd}$ and $4^{th}$ R-R intervals, . . . and a pairwise difference between the $39^{th}$ and $40^{th}$ R-R intervals, resulting in a total of 39 pairwise differences being determined for k=1. More generally, N−k pairwise differences are determined before the answer to the determination at step 1710 is Yes, resulting in flow going to step 1712.

At step 1712 there is a determination of the median of the N−k pairwise differences determined for the value of k. In accordance with certain embodiments, this median value identified at step 1712 is saved at least temporarily so that it can be compared to later determined median values, which are determined at later instances of step 1712. To find the median of N−k pairwise differences for the value of k, the pairwise differences can be arranged in order from least to greatest, and the median is the value that is halfway into the set, i.e., the middlemost value. If there is an even number of values in the data set, then the median can be determined by determining the mean (average) of the two middlemost numbers, or selecting either one of the two middlemost numbers, depending upon the specific implementation.

At step 1714 the value fork is incremented by setting k=k+1. Thus, the first time step 1714 is performed, k=1+1, thereby setting k=2.

At step 1716 there is a determination of whether k is greater than M. If the answer to the determination at step 1716 is No, then flow returns to step 1705, where n is reset to 1.

Steps 1706-1710 are then repeated for k=2, which will result determinations of a pairwise difference between the $1^{st}$ and $3^{rd}$ R-R intervals, a pairwise difference between the $2^{nd}$ and $4^{th}$ R-R intervals, a pairwise difference between $3^{rd}$ and $5^{th}$ R-R intervals, . . . and a pairwise difference between the $38^{th}$ and $40^{th}$ R-R intervals, resulting in a total of 38 pairwise differences. Then, at the next instance of step 1712 there is a determination of the median of the 38 pairwise differences determine for the value of k=2.

At the next instance of step 1714 the value for k is incremented by setting k=k+1. Thus, the second time step 1714 is performed, k=2+1, thereby setting k=3.

At the next instance of step 1716 there is a determination of whether k (which is now equal to 3) is greater than M. Presuming M=10, the answer to the determination at step 1716 is No, returning flow to step 1705, where n is reset to 1.

Steps 1706-1710 are then repeated for k=3, which will result determinations of a pairwise difference between the $1^{st}$ and $4^{th}$ R-R intervals, a pairwise difference between the $2^{nd}$ and $5^{th}$ R-R intervals, a pairwise difference between $3^{rd}$ and $6^{th}$ R-R intervals, . . . and a pairwise difference between the $37^{th}$ and $40^{th}$ R-R intervals, resulting in a total of 37 pairwise differences. Then, at the next instance of step 1712 there is a determination of the median of the 37 pairwise differences determine for the value of k=3.

Assuming M=10, ten instances of step 1712 will be performed before the answer to the determination at step 1716 is Yes, thereby resulting in 10 median pairwise differences being determined (one for each of k=1, k=2, k=3 . . . , and k=10) before flow goes to step 1718. At step 1718 the minimum of the median of the pairwise differences is identified, wherein the value of k corresponding to the minimum of the median of the pairwise differences corresponds to the dominant repeated R-R interval pattern. For example, if the minimum of the 10 median of the pairwise differences corresponds to k=3, then it can be said that most dominant pattern within the window is an R-R interval pattern that repeats every three R-R intervals. This happens to be the case in the example shown above in FIGS. 14 and 15. Referring briefly back to FIG. 15, it can be appreciated that the duration of $1^{st}$ R-R interval is 734.4 ms, the duration of the $4^{th}$ R-R interval is 773.4, the duration of the $7^{th}$ R-R interval is 773.4 ms, the duration of the $10^{th}$ R-R interval is 757.8 ms, the duration of the $13^{th}$ R-R interval is 757.8 ms, . . . the duration of the $36^{th}$ R-R interval is 765.6 ms, the duration of the $39^{th}$ R-R interval is 820.3 ms.

Returning to the discussion of FIG. 17A, after the minimum of the M median pairwise differences is identified at step 1718, flow then goes to step 1720.

At step 1720 there is a determination of whether the minimum of the M median pairwise differences (identified at step 1718) is less than a corresponding threshold. If the answer to the determination at step 1720 is No, that is indicative of a no hidden pattern being identified, and flow goes to step 1722. At step 1722 the AF episode (aka AF trigger) is classified as a true positive, or further AF discrimination is performed. If the answer to the determination at step 1720 is Yes, that is indicative of a hidden regular irregular pattern being identified, and flow goes to step 1724. At step 1724 the AF episode (aka AF trigger) is classified as a false positive, or further AF discrimination is performed.

The method summarized with reference to FIG. 17A essentially performs a pattern recognition, wherein the method first calculates the median R-R interval difference between every interval and the next interval (interval 1 vs. 2, 2 vs. 3, 3 vs. 4, etc. . . . ), i.e., between intervals that are 1 interval apart. This calculation is repeated for intervals that are 2 intervals apart (interval 1 vs. 3, 2 vs. 4, etc. . . . ), 3 intervals apart, . . . , and up to 10 intervals apart (or some other value for M, where M is an integer that is at least 4). This results in 10 (or more generally M) median pairwise differences across all intervals in the window preceding the AF trigger marker. The minimum of these pairwise differences across all intervals is then used to identify the interval period of the dominant pattern. For example, a pattern that repeats itself every 3 intervals would result in the smallest median difference calculated between every interval versus 3 intervals later. If the "minimum median pairwise difference" is below a specified threshold, then the interval variability that caused the AF trigger can be interpreted as actually be associated with a repeating pattern (i.e., false positive AF), and the AF trigger can be rejected.

An example algorithm that can be used to determine a median of N−1 pairwise difference values is shown below, where the median is represented as a median percent difference.

$$\text{Median Percent Difference}=\text{MEDIAN}(100*|RR(n)-RR(n+1)|/RR(n)),\ \text{for intervals}\ n=1{:}N,$$

where

RR(n) is a nth R-R interval within the window,

RR(n+1) is a (n+1)th R-R interval within the window,

IRR(n)−RR(n+1)I is the absolute value of RR(n)−RR (n+1), and

N is a total number of R-R intervals within the window.

The above calculation compares intervals separated by 1 interval, i.e., that are 1 interval apart. This calculation is then repeated for interval separations of 2 through 10, or more generally for 2 though M intervals apart. Expanding the calculation for all interval separations k=1:10, or more generally k=1:M the following equation is used:

$$\text{Median Percent Difference for}\ k=\text{MEDIAN}(100*|RR(n)-RR(n+k)|/RR(n)),\ \text{for intervals}\ n=1{:}N\ \text{and interval separations}\ k=1{:}M.$$

This results in 10 median percent differences, each comparing intervals separated by 1 to 10 intervals. The minimum of these pairwise differences across all intervals is then used to identify the interval period of the dominant pattern (i.e., how many intervals it takes to repeat the pattern).

As noted above, the table in FIG. 15 incudes a list of the forty R-R intervals within a thirty-second window (shown in FIG. 14.) leading up to a detection of an AF episode. Based on these forty R-R intervals, the mean percentage difference for intervals separated by 1 to 10 intervals, calculated using the above note equation, for interval pairs separated by 1, 2, . . . , 10 intervals are as follows: Median Percent Difference=[24.4%, 30.5%, 3.0%, 18.8%, 31.3%, 9.6%, 16.5%, 29.1%, 17.3%, 13.8%]. In this example, the minimum percent difference (3.0%) occurred when each interval was compared to the interval 3 intervals later (i.e., the 3rd of 10 median percent differences). Presuming the threshold is 6%, it can be appreciated that in this example the minimum median percent difference (i.e., 3.0%) is less than the threshold of 6%, and thus it can be concluded that the interval variability that caused the AF trigger was actually associated with a repeating pattern (i.e., false positive AF), and can be rejected.

To reduce processing time, the algorithm may stop calculating the median percent differences as soon as any median R-R interval difference or indicator thereof (e.g., median percent difference) below the threshold is observed. In other words, and more generally, instead of determining all M indicators, then identifying a minimum, and then comparing the minimum to a threshold, the following can be performed instead. Each time a new median R-R interval difference or indicator thereof (e.g., median percent difference) is determined for a value of k, that median R-R interval difference can be compared to the threshold, and then as soon as there is a determination that the median is below the threshold there can be a conclusion that the detection of the AF episode was a false positive AF detection. If the determined median is not less than the threshold, then another value for k is picked and analyzed, until either there is the conclusion of a false positive AF detection or there are no more new values for k to pick and analyze. Using the example window described above with reference to FIGS. 14 and 15, only three median percent differences would need to be calculated (i.e., for values of k=1, 2, and 3) to reject the AF detection as a false positive. An example of such an alternative embodiment is described with reference to FIG. 17B.

Figure 17B:
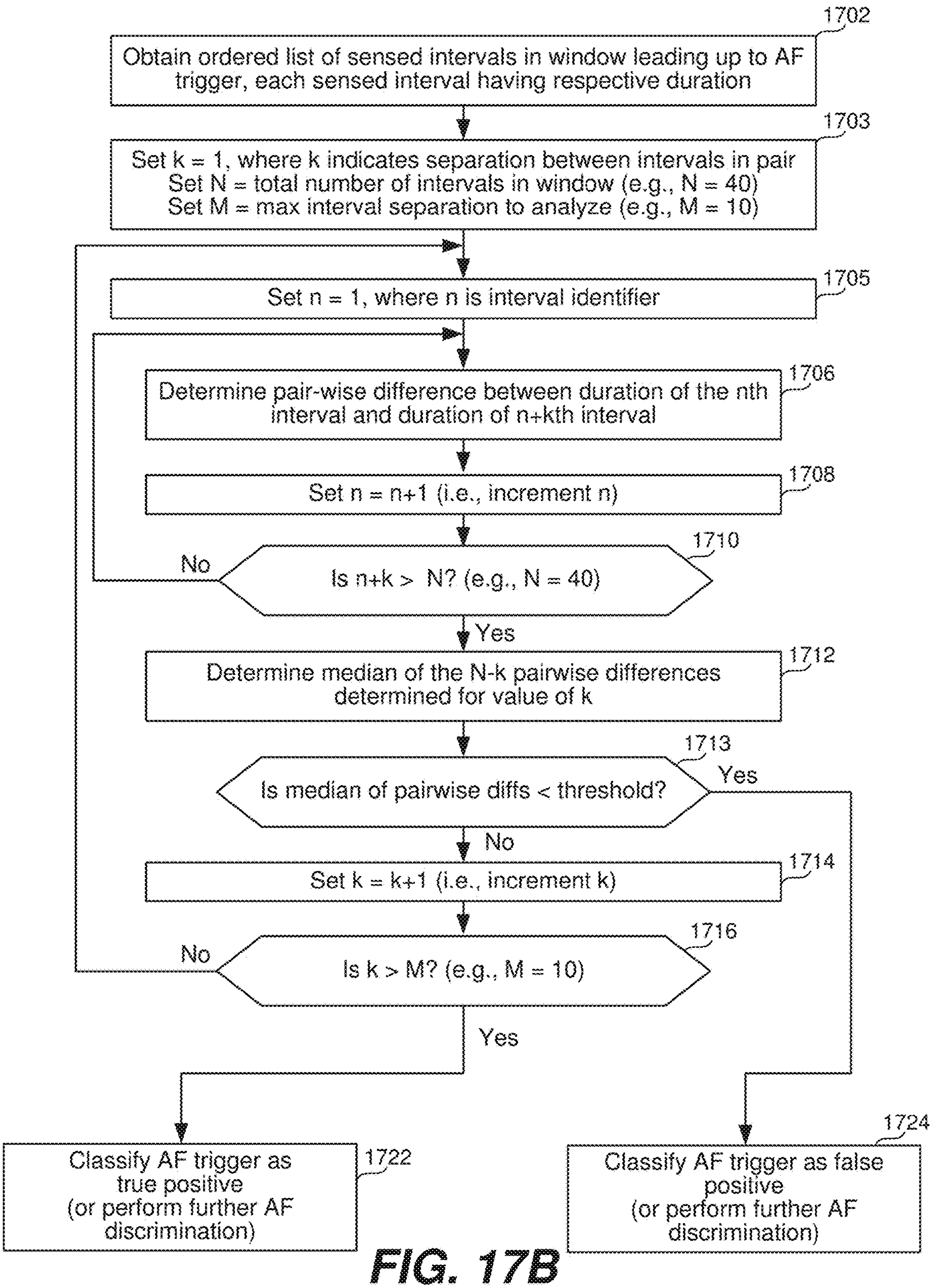

More specifically, FIG. 17B is used to summarize further methods for improving AF episode detection specificity. The steps in FIG. 17B that are the same as those discussed above with reference to FIG. 17A are labeled the same, and need not be described in detail, since reference can be made to FIG. 17A for further details of such steps. Referring to FIG. 17B, steps 1702, 1703, 1705, 1706, 1708, 1710, and 1712 are the same as those commonly numbered steps in FIG. 17A. The first time step 1712 is performed, i.e., for k=1, there is a determination of the median of the N−k (i.e., N−1, e.g., if N=40 then N−k=39 when k=1) pairwise differences determine for the value of k=1, and the median of the N−1 pairwise differences (or an indicator thereof, such as the median percent difference) is compared to a threshold (e.g., 6%) at step 1713. If the median is less than the threshold (i.e., if the answer to the determination at step 1713 is Yes), then flow goes to step 1724. At step 1724 the AF episode (aka AF trigger) is classified as a false positive, or further AF discrimination is performed. If the median is not less than the threshold (i.e., if the answer to the determination at step 1713 is No), then flow goes to step 1714.

At step 1714 the value fork is incremented by setting k=k+1. Thus, the first time step 1714 is performed, k=1+1, thereby setting k=2.

At step 1716 there is a determination of whether k is greater than M. If the answer to the determination at step 1716 is No, then flow returns to step 1705, where n is reset to 1.

Steps 1706-1710 are then repeated for k=2, which will result determinations of a pairwise difference between the 1st and 3rd R-R intervals, a pairwise difference between the 2nd and 4th R-R intervals, a pairwise difference between 3rd and $5^{th}$ R-R intervals, . . . and a pairwise difference between the $38^{th}$ and $40^{th}$ R-R intervals, resulting in a total of 38 pairwise differences. Then, at the next instance of step 1712 there is a determination of the median of the 38 pairwise differences determine for the value of k=2. Then, at the next instance of step 1713, the median of the N−2 pairwise differences for k=2 (or an indicator thereof, such as the median percent difference) is compared to the threshold (e.g., 6%). If the median is less than the threshold (i.e., if the answer to the determination at step 1713 is Yes), then flow goes to step 1724, otherwise flow goes to step 1714.

Presuming the method summarized with reference to FIG. 17B was performed using the R-R intervals within the example window (leading up to the detection of the AF episode) described above with reference to FIGS. 14 and 15, at the third instance of 1713 (i.e., when k=3), the median percent difference for k=3 would be calculated to be 3.0%, resulting in the answer to the determination at step 1713 being Yes, and the detection of the AF episode being classified as a false positive at step 1724. Thus, it can be appreciated that for this example, the median percent differences would only need to be performed three values for k (i.e., for k=1, 2, and 3) before the method came to the false positive conclusion.

Figure 17C:
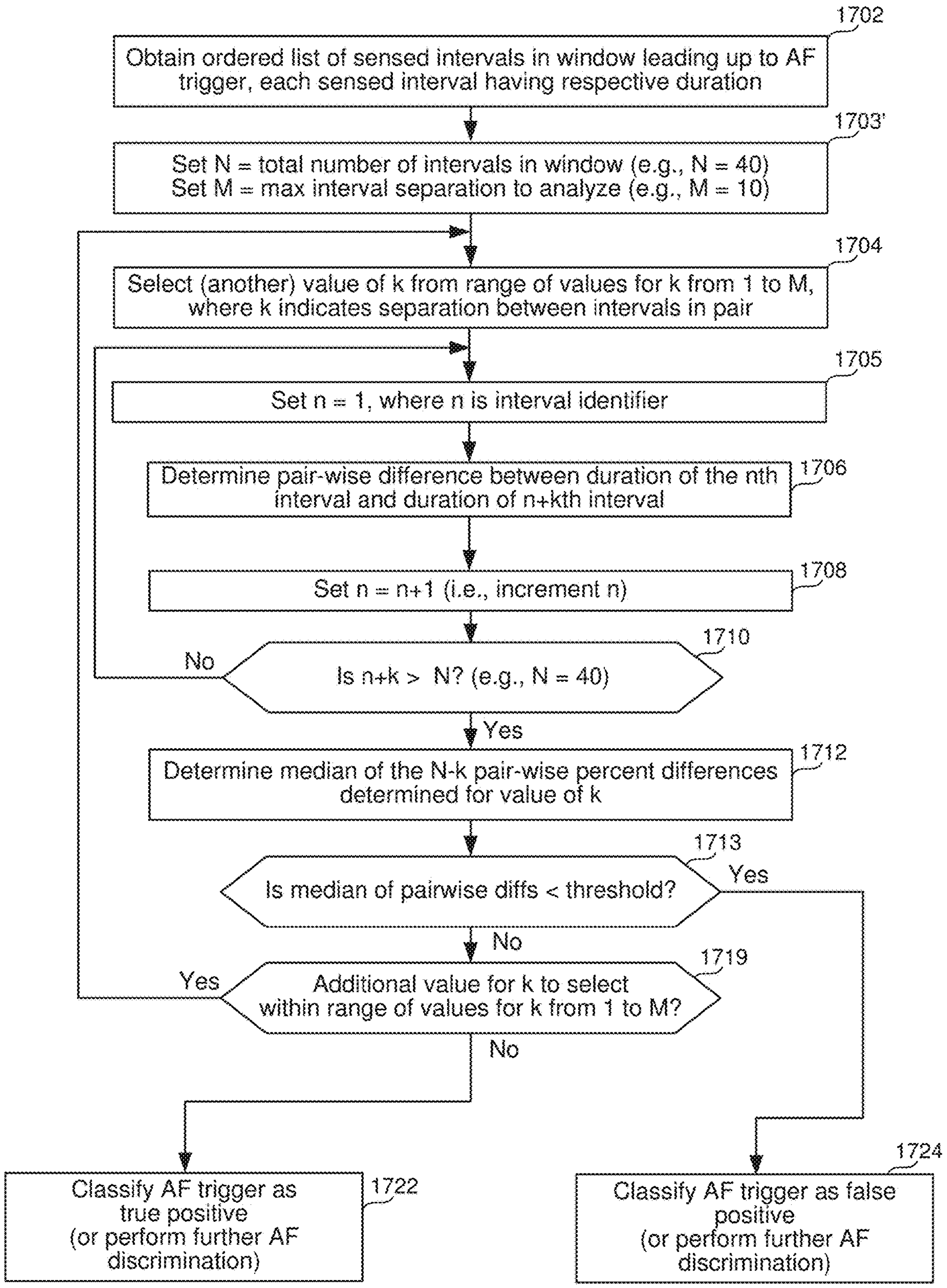

In the methods summarized with reference to with reference to FIG. 17B, a median of the pairwise differences for k=1 (or an indicator thereof) is first determined and compared to a threshold. If the median for k=1 is not less than the threshold, then a median of the pairwise differences for k=2 (or an indicator thereof) is then determined and compared to the threshold. If the median for k=2 is not less than the threshold, then a median of the pairwise differences for k=3 (or an indicator thereof) is then determined and compared to the threshold. This is repeated until a median (or an indicator thereof) is then than the threshold, or until there are not more values for k to analyze within the range of values for k (e.g., until k=M). Accordingly, in FIG. 17A, the initial value for k, that is selected from the range of values for k, is 1, and a median of the pairwise differences (or an indicator thereof) is determined for k=1. Then, if the median is not less than the threshold, steps 1705-1712 are repeated for another selected value of k, wherein the other selected value of k is produced by incrementing k so that k=k+1. In other words, different values for k are tested in ascending numerical order (starting with k=1), where k specifies how many intervals apart the R-R intervals are within each pairwise difference. In alternative embodiments, different values for k can be tested in descending numerical order, starting with k=M, where M is the maximum interval separation that is to be tested, e.g., M=10, or more generally, M is an integer that is at least 4. More generally, values for k can be tested in any order, including in ascending order, descending order, a random order, or some predetermined order. An example of a predetermined order for testing values for k within the range of 1 to 10 can be 6, 5, 7, 4, 8, 3, 9, 2, 1, 10. The flow diagram shown in FIG. 17C summarizes how this can achieved by selecting an initial (or another) value for k at each instance of step 1704 (where k need not start with k=1, but may), and by determining at each instance of step 1719 whether there is at least one additional value for k to select within the range of values for k from 1 to M. The method summarized with reference to FIG. 17B is actually a special case of the method summarized with reference to FIG. 17C, where the different values for k are tested in ascending order starting with k=1. Step 1703' in FIG. 17C differs from step 1703 in FIG. 17B by not initially setting k=1. Rather, any initial value for k (within the range of values from 1 to M) is selected at the first instance of step 1704. The other steps in FIG. 17C that are numbered the same as they are in FIGS. 17A and 17B are the same as those steps described above with reference to FIGS. 17A and 17B and need not be described again.

In certain embodiments, pairwise differences between pairs of intervals that are k intervals apart are represented as percentages, and the medians of N−k pairwise difference percentages are represented as a percentage, i.e., a median percent difference for k, as was described above. In other embodiments, pairwise differences between pairs of intervals that are k intervals apart are represented as simple differences (i.e., |RR(n)−RR(n+k)|), aka deltas, that are not percentages, and the medians of N−k pairwise difference percentages are also represented as simple differences that are not percentages. In still other embodiments, pairwise differences between pairs of intervals that are k intervals apart are represented as ratios, as are the medians thereof. For example, rather than determining the difference between the nth and (n+k)th R-R interval by calculating RR(n)−RR(n+k), the difference can be represented by the ratio of RR(n)/RR(n+k) or RR(n+k)/RR(n), or by the higher of the two R-R intervals over the lower of the two R-R intervals being compared, or vice versa. The closer such a ratio is to unity (i.e., to the value one) the more likely a regular irregular pattern exists, which is an indicator of a non-AF event. Where ratios are used, the threshold used can be a threshold range, e.g., between 0.8 and 1.2, but not limited thereto. Other variations are also possible and within the scope of the embodiments described herein.

Morphology-Based Detection of P-Wave Oversensing

As briefly discussed above with reference to step 218 in FIG. 2, a morphology-based AF discriminator can be used to detect P-wave over-sensing, which if present beyond a specified threshold, can be used to classify an AF detection as a false positive detection. Details of such a morphology-based AF discriminator are described below with reference to FIGS. 18-21.

For various reasons, including an implant angle of an IMD relative to the heart, the dynamically changing R-wave amplitude may occasionally be too small to detect, thereby leading to R-wave undersensing. In other cases, P-wave and/or T-wave amplitudes exceeding the R-wave sensing threshold may result in R-waves oversensing. Where T-waves and/or P-waves are falsely identified as R-waves, false R-R intervals can be identified which have a high variability, leading to false detections of AF. In addition, the ICM systems also have additional algorithms designed to reject false detections of AF if presence of P-waves is identified in the EGM or ECG signal. With T-waves and/or P-waves oversensing, these additional algorithms cannot find the true P-wave segments in the EGM/ECG signal thus may fail to reject false detections of AF. In other words, over-sensed P-waves and/or over-sensed T-waves can lead to false positive AF detections. An over-sensed P-wave, as the term is used herein, refers to a P-wave that is falsely identified as an R-wave. Similarly, an over-sensed T-wave, as the term is used herein, refers to a T-wave that is falsely identified as an R-wave. An under-sensed R-wave, as the term is used herein, refers to an R-wave that is not detected An over-sensed R-wave, as the term is used herein, refers to a feature (e.g., a P-wave or a T-wave) of an EGM or ECG that is falsely identified as an R-wave.

Figure 18:
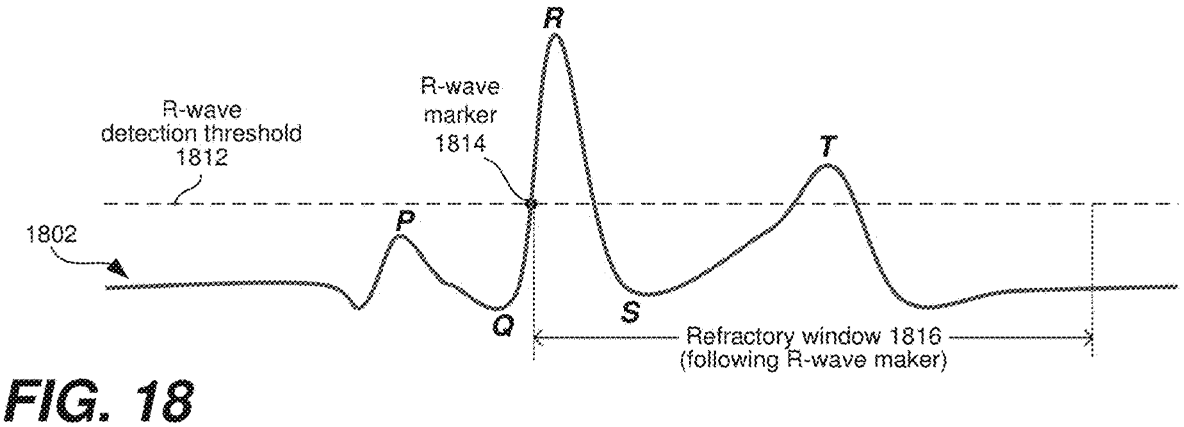
FIG. 18 includes a portion of an EGM and is used to show how a true R-wave can be detected based at least in part on the EGM crossing an R-wave detection threshold.
Figure 19:
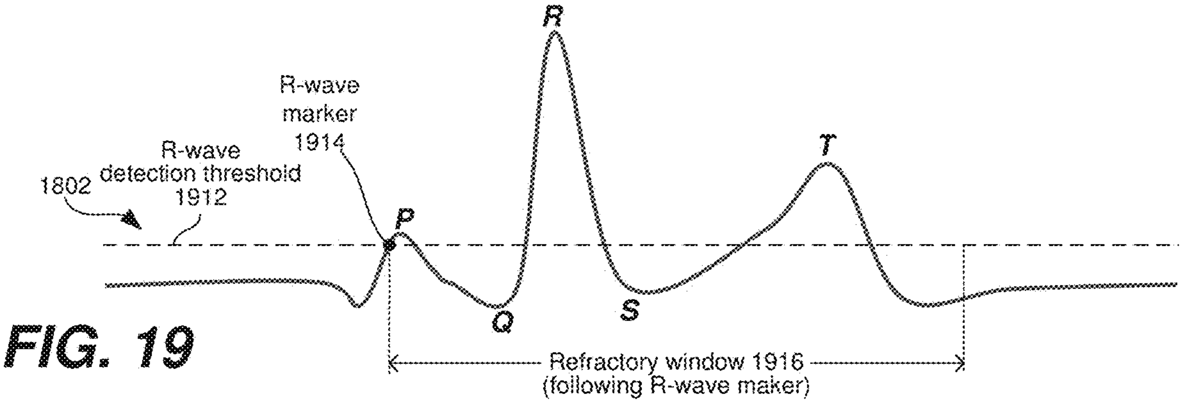
FIG. 19 includes the same portion of the EGM included in FIG. 18, and is used to show how a P-wave can be mistakenly detected as an R-wave, due to a low R-wave detection threshold, which can lead to the true R-wave not being detected.
Figure 20:
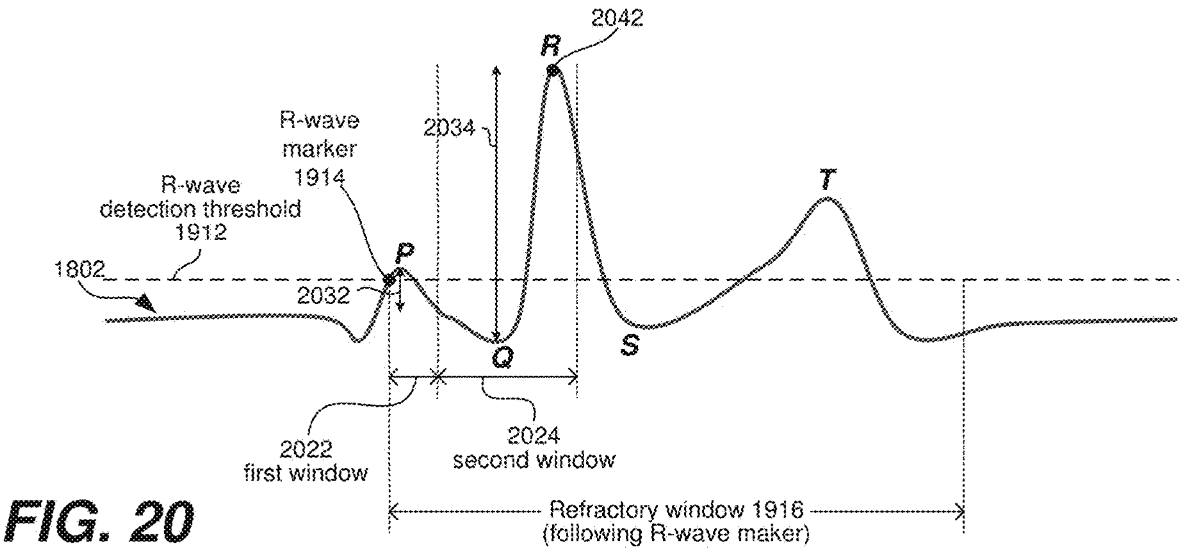
FIG. 20 includes the same portion of the EGM included in FIGS. 18 and 19, and is used to show how a P-wave that is mistakenly detected as an R-wave, can be identified as a false R-wave, which can also allow for identification of the true R-wave which was initially not identified.

FIGS. 18-20 illustrate the same portion of the same EGM 1802, and includes labels indicating where a P-wave, a Q-wave, an R-wave, an S-wave, and a T-wave are actually located within the portion of the EGM 1802. FIG. 18 is used to show how a true R-wave can be detected based on the EGM crossing an R-wave detection threshold 1812. FIG. 2 is used to show how a P-wave can be mistakenly detected as an R-wave, due to P-wave oversensing, which can lead to the true R-wave not being detected. Thereafter, FIG. 20 is used to show how a P-wave that is mistakenly detected as an R-wave, due to P-wave oversensing, can be identified as a false R-wave using an embodiment of the present technology, which can also allow for identification of the true R-wave which was initially not identified.

Referring to FIG. 18, the portion of the EGM 1802 shown therein, as noted above, includes labels indicating where the P-wave, the Q-wave, the R-wave, the S-wave, and the T-wave are actually located. Also shown in FIG. 18 is a dashed line labeled 1812 which is representative of an example R-wave detection threshold. Such an R-wave detection threshold 1812 can be used to detect the R-wave, e.g., by identifying when the EGM 1802 crosses the R-wave detection threshold, but is not limited thereto. In other words, the R-wave shown in FIG. 18 can be detected based on when the EGM 1802 crosses the R-wave detection threshold 1812. It is noted that the term "based on" as used herein, unless stated otherwise, should be interpreted as meaning based at least in part on, meaning there can be one or more additional factors upon which a decision or the like is made. For an example, one or more additional factors can be used to detect an R-wave, or the like, such as a comparison between the morphology of an EGM and a stored R-wave template, EGM slope, and/or the like.

Still referring to FIG. 18, the dot labeled 1814 is representative of an R-wave marker, which in this example, coincides with a crossing of the R-wave detection threshold 1812 by the EGM 1802. However, it may not always be the case that the R-wave marker 1814 coincides with the initial crossing of the R-wave detection threshold 1812 by the EGM 1802. Nevertheless, what will typically be the case is that the R-wave marker 1814, when correctly marking an R-wave, will mark a point in time between an immediately preceding Q-wave and a peak of an R-wave, as is the case in FIG. 18. Also shown in FIG. 18 is an exemplary refractory window 1816, following the R-wave marker 1814, wherein the refractory widow 1816 corresponds to a period of time during which an IMD does not search or sense for an R-wave because an R-wave had just been detected. An example duration of the refractory window 1816, which begins at the R-wave marker 1814, is within the range of 250 msec to 300 msec, inclusive.

Referring now to FIG. 19, the portion of the EGM shown therein is the same as the portion shown FIG. 18, and thus the portion of the EGM is again labeled 1802. Also shown in FIG. 19 is another example R-wave detection threshold 1912, which has a lower magnitude than the R-wave detection threshold 1814 shown in FIG. 18. Additionally shown in FIG. 19 is an R-wave marker 1914 that incorrectly marks a portion of the P-wave as the R-wave, at least in part due to the peak of the P-wave being greater than the R-wave detection threshold 1912. Following the R-wave marker 1914 is the refractory window 1916 during which the IMD does not search or sense for an R-wave because an R-wave had just been detected, albeit incorrectly. Note that in FIG. 19 the actual R-wave is within the refractory window 1916.

Referring now to FIG. 20, the R-wave detection threshold 1912, the R-wave marker 1914, and the refractory window 1916 are the same as they were in FIG. 19, and thus they are labeled the same as they were in FIG. 19. Also shown in FIG. 20 are first and second windows 2022, 2024, which are utilized in accordance with an embodiment of the present invention to determine that the detected R-wave (aka the detected R-wave) was actually a false R-wave detection (aka a false positive detection). The first window 2022 starts at a first time that coincides with the R-wave marker 1914 (or more generally, at a marker for a potential R-wave), ends at a second time after the first time, and has a first duration. An example duration of the first window is 50 milliseconds (msec), but other durations for the first window within the range of 20 msec to 100 msec inclusive are also possible and within the scope of the embodiments described herein. The second window 2024 starts at the end of the first window 2022 (i.e., at a second time), ends at a third time after the second time, and has a second duration that is at least twice the first duration. An example duration of the second window is 200 msec, but other durations for the second window within the range of 150 msec to 350 msec inclusive are also possible and within the scope of the embodiments described herein. The duration of the second window (aka the second duration) is at least twice the duration of the first window (aka the first duration), and in certain embodiments is at least three times the duration of the first window.

The portion of EGM 1802 within the first window 2022 can be referred to herein as a first portion of the EGM, and the portion of the EGM 1802 within the second window 2024 can be referred to herein as a second portion of the EGM. In accordance with certain embodiments, a maximum peak-to-peak amplitude of the first portion of the EGM (i.e., the portion of the EGM within the first window 2022) and a maximum peak-to-peak amplitude of the second portion of the EGM (i.e., the portion of the EGM within the second window 2024) are determined and compared to one another to determine whether the maximum peak-to-peak amplitude of the second portion of the EGM is at least a specified extent larger than the maximum peak-to-peak amplitude of the first portion of the EGM, which should only occur where an actual R-wave occurs within the second window 2024, and thus, is indicative of the R-wave detection (corresponding to the R-wave marker 1914) being a false R-wave, and more specifically, an over-sensed P-wave. The specified extent larger can be N times larger, where N has a value of at least 2, and examples values for N are 2, 2.25, 2.5, 2.75, and 3, but are not limited thereto. For example, where N is specified to be equal to 3, then a R-wave detection would be classified as a false R-wave detection where the maximum peak-to-peak amplitude of the second portion of the EGM is at least a 3 times larger than the maximum peak-to-peak amplitude of the first portion of the EGM. In FIG. 20, the vertical double arrowed line labeled 2032 shows the maximum peak-to-peak amplitude of the first portion of the EGM 1802, and the vertical double arrowed line labeled 2034 shows the maximum peak-to-peak amplitude of the second portion of the EGM 1802. In FIG. 20, the maximum peak-to-peak amplitude 2032 of the second portion of the EGM is more than 3 times larger than the maximum peak-to-peak amplitude 2034 of the first portion of the EGM, resulting in the R-wave detection (associated with the R-wave marker 1914) being classified as a false R-wave, and in certain embodiments, results in the R-wave detection (associated with the R-wave marker 1914) being classified as an over-sensed P-wave.

Instead of comparing the maximum peak-to-peak amplitude of the second portion of the EGM (i.e., the portion of the EGM within the second window 2024) to the maximum peak-to-peak amplitude of the first portion of the EGM (i.e., the portion of the EGM within the first window 2022), an alternative measure of magnitude of the second portion of the EGM can be compared to the alternative measure of magnitude of the first portion of the EGM. An alternative measure of magnitude is an absolute value of a maximum peak, in which case if the absolute value of the maximum peak within the second portion of the signal is at least the specified extent larger (e.g., at least 3 times larger) than the absolute value of the maximum peak within the first portion of the signal, then the R-wave detection (corresponding to an R-wave marker) will be classified as a false R-wave.

In an alternative embodiment, the measure of magnitude is an absolute value of a first derivative. Where the measure of magnitude is the absolute peak value of the first derivative, the first derivative of the first portion of the EGM (i.e., the portion of the EGM within the first window 2022) is determined, and the first derivative of the second portion of the EGM (i.e., the portion of the EGM within the first window 2022) is determined. If the absolute peak value of the first derivative of the second portion of the signal is at least the specified extent larger (e.g., at least 3 times larger) than the absolute peak value of the first derivative of the first portion of the signal, then the R-wave detection (corresponding to an R-wave marker) is classified as a false R-wave.

In still another alternative embodiment, the measure of magnitude is an area under the curve. Where the measure of magnitude is the area under the curve, the area under the curve of the first portion of the EGM (i.e., the portion of the EGM within the first window 2022) is determined, and the area under the curve of the second portion of the EGM (i.e., the portion of the EGM within the second window 2024) is determined. If the area under the curve of the second portion of the signal is at least the specified extent larger (e.g., at least 3 times larger) than the area under the curve of the first portion of the signal, then the R-wave detection (corresponding to an R-wave marker) is classified as a false R-wave. The use of still other measures of magnitude are possible and within the scope of the embodiments described herein.

Figure 21:
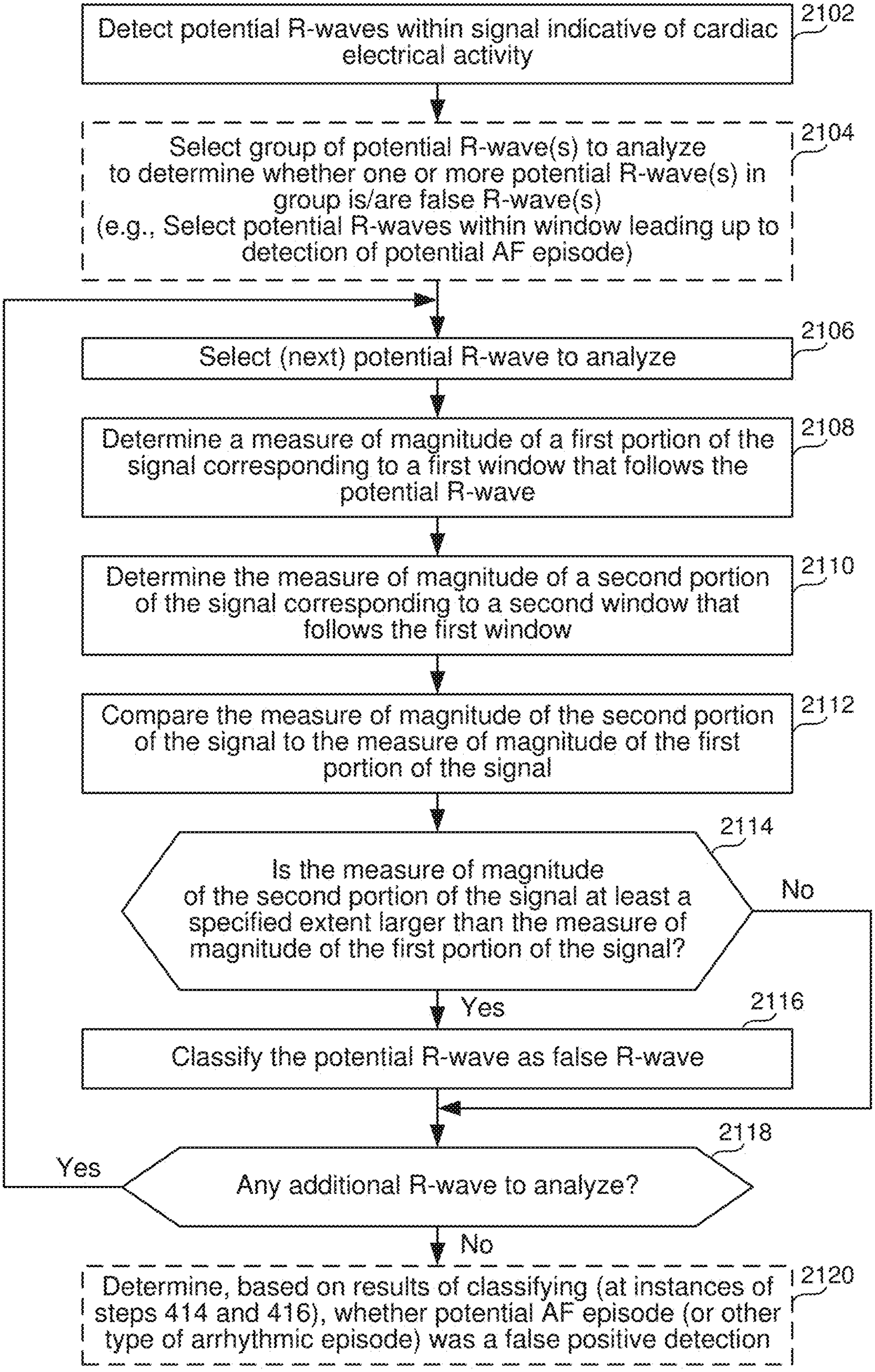
FIG. 21 includes a high level flow diagram that is used to describe how a detected potential R-wave can be classified as a false R-wave, thereby improving R-wave detection sensitivity and positive predictive value.

The high level flow diagram of FIG. 21 will now be used to summarize methods that can be used to determine whether a detected R-wave should be classified as a false R-wave (or more specifically an over-sensed P-wave), which embodiments can be used to improve R-wave detection sensitivity and positive predictive value. Referring to FIG. 21, step 2102 involves detecting potential R-waves within a signal indicative of cardiac electrical activity, such as an EGM or ECG. Step 2102 can be performed, e.g., by comparing the signal indicative of cardiac electrical activity, or samples thereof, to an R-wave detection threshold (e.g., 1812 or 1912), and detecting potential R-waves based on the signal indicative of cardiac electrical activity, or the samples thereof, crossing the R-wave detection threshold. Additionally, or alternatively, potential R-waves can be detecting by comparing the morphology of the signal indicative of cardiac electrical activity to an R-wave morphological template and detecting potential R-waves when there is a sufficient level of similarity or correlation between a portion of the signal and the template. Additional and/or alternative techniques for detecting potential R-waves are also possible and within the scope of the embodiments described herein. In accordance with certain embodiments, each of the potential R-waves is associated with a respective temporal R-wave marker (e.g., 1814 or 1914) indicative of when a portion of the signal indicative of cardiac electrical activity, or samples thereof, crossed the R-wave detection threshold, or more generally, indicative of a temporal location of the potential R-wave.

Still referring to FIG. 21, optional step 2104 involves selecting a group of potential R-wave(s) to analyze to determine whether one or more potential R-wave(s) within the group is/are false R-wave(s). This step can involve, e.g., selecting potential R-waves within a window (e.g., a 30 second window) leading up to the detection of an AF episode.

Step 2106 involves selecting a potential R-wave to analyze. Where step 2104 is performed, step 2106 can involve selecting one of the potential R-waves from the group that was selected at step 2104. Where multiple potential R-waves are to be analyzed, the R-waves selected at instances of step 2106 can be selected in a temporal order, or in a random order, but is not limited thereto.

Step 2108 involves determining a measure of magnitude of a first portion of the signal corresponding to a first window (e.g., 2022) that follows the potential R-wave. Step 2110 involves determining the measure of magnitude of a second portion of the signal corresponding to a second window (e.g., 2024) that follows the first window. Step 2112 involves comparing the measure of magnitude of the second portion of the signal (corresponding to the second window and determined at step 2110) to the measure of magnitude of the first portion of the signal (corresponding to the first window and determined at step 2108). Step 2114 involves determining whether the measure of magnitude of the second portion of the signal (determined at step 2110) is at least a specified extent larger than the measure of magnitude of the first portion of the signal (determined at step 2108). The order of steps 2108 and 2110 can be reversed, or steps 2108 and 2110 can be performed at the same time. Further, while steps 2112 and 2114 are shown as two separate steps, they can be combined into a single step.

Still referring to FIG. 21, if the answer to the determination at step 2114 is Yes, then flow goes to step 2116 and the potential R-wave is classified as a false R-wave. In certain embodiments the classifying the potential R-wave as a false R-wave at step 2116 more specifically involves classifying the potential R-wave as an over-sensed P-wave. If the answer to the determination at step 2114 is No, then flow goes to step 2118, at which point there is a determination of whether there is any additional R-wave to analyze. In a specific embodiment, if the answer to the determination at step 2114 is No, then flow can go to an additional step (not shown) that either classifies the potential R-wave as a true R-wave, or that increases a confidence level or probability that the potential R-wave that was analyzed is a true-R-wave. As can be appreciated from the above discussion, steps 2110-2116 collectively provide a way of determining whether to classify a potential R-wave as a false R-wave, and in specific embodiments, collectively provide a way of determining whether to classify a potential R-wave as an over-sensed P-wave.

If the answer to determination at step 2118 is Yes, meaning that there is at least one additional R-wave to analyze, then flow returns to 2106 and another potential R-wave is selected for analysis, to determine whether it should be classified as a false R-wave. If the answer to the determination at step 2118 is No, then flow goes to optional step 2120.

Referring to FIG. 21, step 2120 is an optional step that can be used where a group of potential R-waves that were analyzed were those R-waves in a window leading up to the detection of a potential arrhythmic episode (e.g., an AF episode). Step 2120 involves determining, based on results of the classifying (at multiple instances of steps 2114 and 2116), whether the potential arrhythmic episode was a false positive detection. For an example, this can involves classifying an AF episode as a false positive if more than a specified threshold amount (e.g., a specified number or percentage) of the potential R-waves within the window (leading up to the potential arrhythmic episode) were classified as being false R-waves. In still another embodiment, the respective the R-wave marker for each of the potential R-waves that were classified as being a false R-wave can be moved to a temporal position within the respective second window, such as to the temporal positional of the maximum peak in the second window. In other words, in response to classifying a potential R-wave as a false R-wave, the respective temporal R-wave marker for the potential R-wave can be moved to coincide with a peak in the respective second window that follows the potential R-wave. For an example, briefly referring back to FIG. 20, the temporal R-wave marker 1914 can be moved to the temporal position of the dot 2042, which in this example is the location of the peak in the second window 2024. This would result in an updated or corrected group of potential R-waves, wherein each of the potential R-waves in the updated or corrected group is associated with a respective R-wave marker. Using this updated or corrected group, whatever arrhythmia detection algorithm was used to detect the potential arrhythmic episode (e.g., the potential AF episode) can be rerun to redetermine whether or not a potential arrhythmic episode occurred. If, after rerunning the arrhythmia detection algorithm, the potential arrhythmic episode is again detected, then the detection of the arrhythmic episode can be classified as a true detection (aka a true positive), or there can be an increase to a confidence level or probability that the potential arrhythmic episode was an actual (i.e., true) arrhythmic episode. Alternatively, the rerunning of the arrythmia detection algorithm may fail to detect an arrythmia, in which case it can be concluded that the originally detected potential arrhythmic episode was a false positive detection.

P-waves are generated by organized activation of both atrial chambers during normal sinus rhythm. Accordingly, P-waves are not present during an actual AF episode, which is associated with disorganized and chaotic atrial electric activities. In accordance with certain embodiments of the present technology, an IMD can be configured to classify an AF detection as a false positive (i.e., to reject an AF detection as being false) where at least a specified number N (e.g., where N is integer that has a value of at least 1) of P-waves are identified in a segment of an EGM leading up to the detection of AF (aka, the AF detection). However, where an IMD detects an actual P-wave as an R-wave, due to P-wave oversensing, the IMD may fail to reject the potential AF detection as a false detection (aka a false positive). By utilizing embodiments described herein to determine that one or more potentials R-wave are actually over-sensed P-waves within a window leading up to the detection of an AF episode, such embodiments can be used to classify the detection of an AF episode as a false positive detection. More specifically, in response to determining that at least a threshold number N of P-waves and/or over-sensed P-waves are including in a window (e.g., a 30 second window) leading up to an AF detection, the detection of the AF episode can be rejected or classified as being a false positive detection.

Referring back to steps 2108-2112, the measure of magnitude used in these steps can be, as noted above, an absolute value of a maximum peak, a maximum peak-to-peak amplitude, an absolute peak value of a first derivative, or an area under a curve, but is not limited thereto. Still referring back to steps 2108-2112, in accordance with certain embodiments, the first window starts at a first time that coincides with a marker for the potential R-wave, ends at a second time after the first time, and has a first duration; and the second window starts at the second time, ends at a third time after the second time, and has a second duration that is at least twice the first duration. In accordance with certain embodiments, the first duration (i.e., the duration of the first window) is within a range of 20 msec to 100 msec inclusive; and the second duration (i.e., the duration of the second window) is within a range of 150 msec to 350 msec inclusive.

Still referring back to steps 2108-2112, the specified extent larger referred to in these steps can be N times larger, where N has a value of at least 2. In such embodiments, step 2114 involves determining whether the measure of magnitude of the second portion of the signal is at least N times larger than the measure of magnitude of the first portion of the signal, and step 2116 involves classifying the potential R-wave as a false R-wave, in response to determining that the measure of magnitude of the second portion of the signal is at least N times larger than the measure of magnitude of the first portion of the signal. It is noted that determining whether the measure of magnitude of the second portion of the signal is at least 2 times larger than the measure of magnitude of the first portion of the signal, is the equivalent to determining whether the measure of magnitude of the second portion of the signal is at least 100 percent larger than the measure of magnitude of the first portion of the signal. For another example, determining whether the measure of magnitude of the second portion of the signal is at least 3 times larger than the measure of magnitude of the first portion of the signal, is the equivalent to determining whether the measure of magnitude of the second portion of the signal is at least 200 percent larger than the measure of magnitude of the first portion of the signal.

In alternative embodiments, the specified extent larger referred to in steps 2108-2112 is a magnitude of M larger. In such embodiments, step 2114 involves determining whether the measure of magnitude of the second portion of the signal is at least a magnitude of M larger than the measure of magnitude of the first portion of the signal, and step 2116 involves classifying the potential R-wave as a false R-wave, in response to determining that the measure of magnitude of the second portion of the signal is at least the magnitude of M larger the measure of magnitude of the first portion of the signal. The specific value for M, in such embodiments, can be selected for an expected range of measures of magnitude, and may be tailored to a specific device or system.

Morphology-Based Detection of P-Waves

P-waves are generated by organized activation of both atria during sinus rhythm. AF is associated with disorganized and chaotic atrial electric activity. Accordingly, actual P-waves should not be present during an actual episode of AF, as briefly discussed above with reference to step 220 in FIG. 2. Accordingly, one of the techniques that can be used to determine whether a detected episode of AF should be classified as a false positive detection is analyzing the morphology of an EGM or ECG within a window (e.g., a 30 second window) leading up to the detection of the AF episode. This can involve, for example, comparing one or more P-wave morphology templates to the portion of an EGM or ECG prior to each sensed R waves that precede the AF detection. An actual P-wave can be determined to be detected if the correlation between a P-wave morphology template and a portion of the EGM or ECG exceeds a specified correlation threshold.

Given that an amplitude of a P-wave is relatively small within an EGM or ECG signal and subject to noise, as well as beat by beat variation, utilize advanced signal processing techniques may be used to accurately detect the presence of P-waves and to confirm the P-waves utilizing morphology-based template matching, e.g., as described in U.S. patent application Ser. No. 15/973,107, titled "Method And System To Detect P-Waves In Cardiac Arrhythmic Patterns," to Malhotra et al., which was filed on May 7, 2018, which is incorporate herein by reference. Further morphology-based techniques for detecting P-waves are described in U.S. patent application Ser. No. 16/871,261, titled "Method and System for Detecting Low Level P-waves," to Bornzin et al., filed May 11, 2020, which is also incorporated herein by reference. Still another morphology-based technique for detecting P-waves within an EGM or ECG is disclosed in U.S. patent application Ser. No. 16/991,421, titled "Method And System To Detect P-Waves In Cardiac Arrhythmic Patterns," filed Aug. 12, 2020, which is incorporated herein by reference. Various other known or future developed morphology-based techniques for detecting P-waves within an EGM or ECG can alternatively or additional be used.

In accordance with certain embodiments, an AF detection can be rejected if as few as one P-wave is detected within a portion of an EGM or ECG signal that was initially found to correspond to AF. In other words, an AF detection can be rejected if a single P-wave is included in a window of an EGM or ECG signal leading up to the AF detection. Alternatively, it may be that a specified threshold number of P-waves (e.g., at least two P-waves) need to be detected in order for an AF detection to be classified as a false positive detection. More generally, if the number of P-waves detected exceeds a specified threshold, wherein the threshold is a specified value that is equal to or greater than 1, an AF detection is rejected. Alternatively, if P-waves are detected in least a threshold percent (e.g., 5% or 10%, but not limited thereto) of the cardiac cycles within the window leading up to the AF detection, the AF detection is rejected. More specifically, at step 220 in FIG. 2 there is a determination of whether actual P-waves beyond a corresponding threshold (e.g., a value or a percent threshold) are present within the window leading up to the AF detection, and based thereon, an AF detection can be rejected.

Example Implantable Medical Device (IMD)

Figure 22:
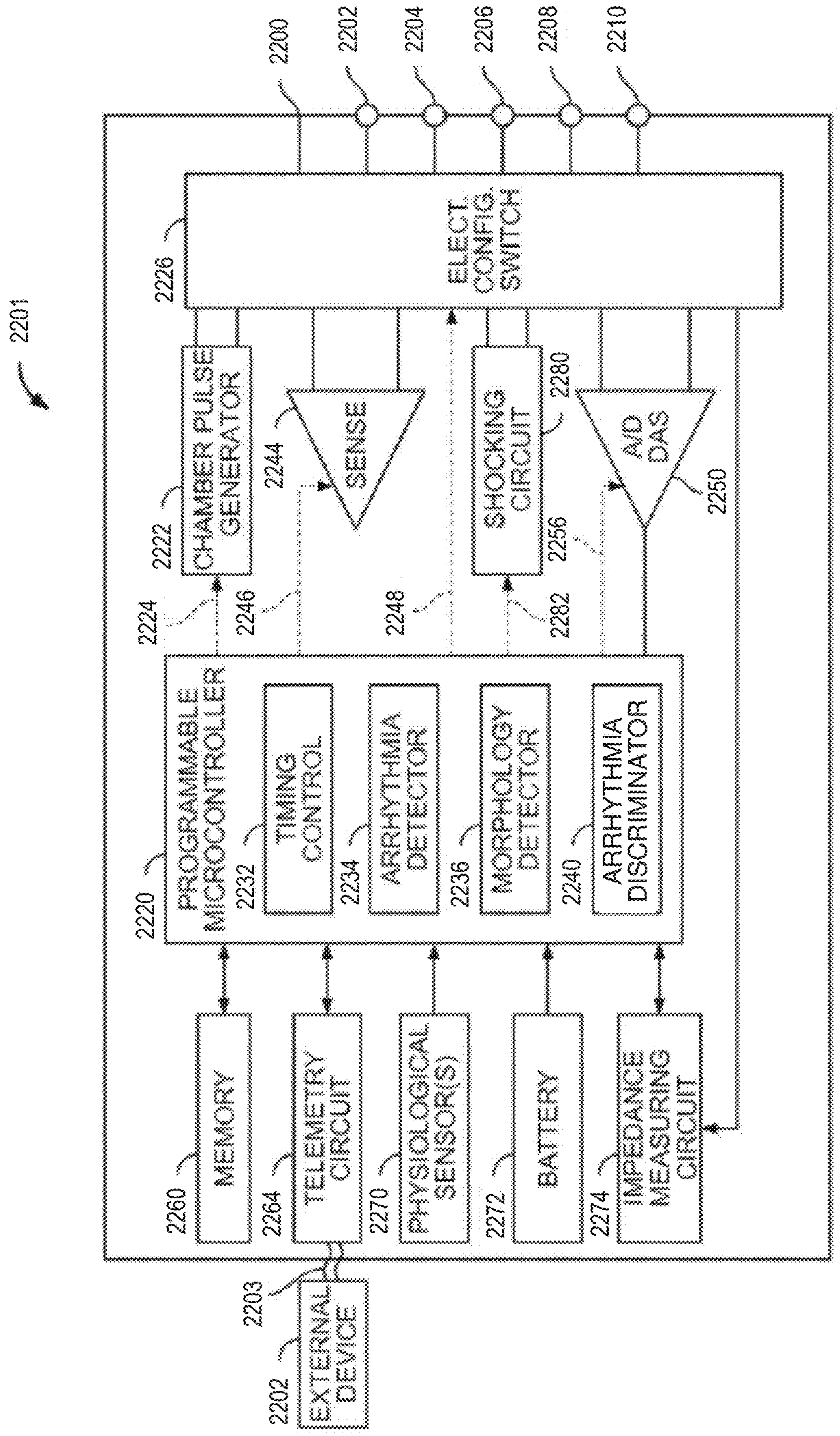
FIG. 22 shows a block diagram of one embodiment of an IMD that is implanted into a patient and can be used to implement certain embodiments of the present technology.

FIG. 22 shows a block diagram of one embodiment of an IMD that is implanted into a patient in accordance with a certain embodiment of the present technology. The IMD 2201 may be implemented as a full-function biventricular pacemaker, equipped with both atrial and ventricular sensing and pacing circuitry for four chamber sensing and stimulation therapy (including both pacing and shock treatment). Optionally, the IMD 2201 may provide full-function cardiac resynchronization therapy. Alternatively, the IMD 2201 may be implemented with a reduced set of functions and components. For instance, the IMD may be implemented without pacing, e.g., if the IMD is an ICM. The IMD 2201 can be coupled to one or more leads for single chamber or multi-chamber pacing and/or sensing. Alternatively, the IMD 2201 can be an LCP that includes electrodes located on or very close to a housing 2200 of the IMD 2201.

The IMD 2201 has a housing 2200 to hold the electronic/computing components. The housing 2200 (which is often referred to as the "can", "case", "encasing", or "case electrode") may be programmably selected to act as the return electrode for certain stimulus modes. The housing 2200 may further include a connector (not shown) with a plurality of terminals 2202, 2204, 2206, 2208, and 2210. The terminals may be connected to electrodes that are located in various locations on the housing 2200 or to electrodes located on leads. The IMD 2201 includes a programmable microcontroller 2220 that controls various operations of the IMD 2201, including cardiac monitoring and/or stimulation therapy. The microcontroller 2220 includes a microprocessor (or equivalent control circuitry), RAM and/or ROM memory, logic and timing circuitry, state machine circuitry, and I/O circuitry.

The IMD 2201 further includes a pulse generator 2222 that generates stimulation pulses and communication pulses for delivery by one or more electrodes coupled thereto. The pulse generator 2222 is controlled by the microcontroller 2220 via a control signal 2224. The pulse generator 2222 may be coupled to the select electrode(s) via an electrode configuration switch 2226, which includes multiple switches for connecting the desired electrodes to the appropriate I/O circuits, thereby facilitating electrode programmability. The switch 2226 is controlled by a control signal 2228 from microcontroller 2220.

In the embodiment of FIG. 22, a single pulse generator 2222 is illustrated. Optionally, the IMD may include multiple pulse generators, similar to the pulse generator 2222, where each pulse generator is coupled to one or more electrodes and controlled by the microcontroller 2220 to deliver select stimulus pulse(s) to the corresponding one or more electrodes.

The microcontroller 2220 is illustrated as including timing control circuitry 2232 to control the timing of the stimulation pulses (e.g., pacing rate, atrio-ventricular (AV) delay, atrial interconduction (A-A) delay, or ventricular interconduction (V-V) delay, etc.). The timing control circuitry 2232 may also be used for the timing of refractory periods, blanking intervals, noise detection windows, evoked response windows, alert intervals, marker channel timing, and so on. The microcontroller 2220 also has an arrhythmia detector 2234 for detecting arrhythmia conditions and a morphology detector 2236. The arrhythmia detector 2234 can, for example, detect episodes of AF. Although not shown, the microcontroller 2220 may further include other dedicated circuitry and/or firmware/software components that assist in monitoring various conditions of the patient's heart and managing pacing therapies. The microcontroller 2220 is also shown as including an arrhythmia discriminator 2240, which can be used to perform the embodiments of the present technology described above with reference to FIGS. 1-21, e.g., to determine whether one or more AF detections are false positives. The arrhythmia discriminator 2240 can more generally be implemented using hardware, software, firmware, and/or combinations thereof. The microcontroller can include a processor. The microcontroller, and/or the processor thereof, can be used to perform the methods described herein.

The IMD 2201 can be further equipped with a communication modem (modulator/demodulator) to enable wireless communication with the remote slave pacing unit. The modem may include one or more transmitters and two or more receivers. In one implementation, the modem may use low or high frequency modulation. As one example, modem may transmit implant-to-implant (i2i) messages and other signals through conductive communication between a pair of electrodes. Such a modem may be implemented in hardware as part of the microcontroller 2220, or as software/firmware instructions programmed into and executed by the microcontroller 2220. Alternatively, the modem may reside separately from the microcontroller as a standalone component.

The IMD 2201 includes a sensing circuit 2244 selectively coupled to one or more electrodes, that perform sensing operations, through the switch 2226 to detect the presence of cardiac activity in the right chambers of the heart. The sensing circuit 2244 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. The switch 2226 determines the sensing polarity of the cardiac signal by selectively closing the appropriate switches. In this way, the clinician may program the sensing polarity independent of the stimulation polarity.

The output of the sensing circuit 2244 is connected to the microcontroller 2220 which, in turn, triggers or inhibits the pulse generator 2222 in response to the presence or absence of cardiac activity. The sensing circuit 2244 receives a control signal 2246 from the microcontroller 2220 for purposes of controlling the gain, threshold, polarization charge removal circuitry (not shown), and the timing of any blocking circuitry (not shown) coupled to the inputs of the sensing circuitry.

In the embodiment of FIG. 22, a single sensing circuit 2244 is illustrated. Optionally, the IMD may include multiple sensing circuits, similar to the sensing circuit 2244, where each sensing circuit is coupled to one or more electrodes and controlled by the microcontroller 2220 to sense electrical activity detected at the corresponding one or more electrodes. The sensing circuit 2244 may operate in a unipolar sensing configuration or in a bipolar sensing configuration.

The IMD 2201 further includes an analog-to-digital (A/D) data acquisition system (DAS) 2250 coupled to one or more electrodes via the switch 2226 to sample cardiac signals across any pair of desired electrodes. Data acquisition system 2250 is configured to acquire intracardiac electrogram signals, convert the raw analog data into digital data, and store the digital data for later processing and/or telemetric transmission to an external device 2254 (e.g., a programmer, local transceiver, or a diagnostic system analyzer). Data acquisition system 2250 is controlled by a control signal 2256 from the microcontroller 2220.

The microcontroller 2220 is coupled to a memory 2260 by a suitable data/address bus. The programmable operating parameters used by the microcontroller 2220 are stored in memory 2260 and used to customize the operation of the IMD 2201 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of the IMD 2201 may be non-invasively programmed into memory 2260 through a telemetry circuit 2264 in telemetric communication via a communication link 2203 with an external device 2254. The telemetry circuit 2264 allows intracardiac electrograms and status information relating to the operation of the IMD 2201 (as contained in the microcontroller 2220 or memory 2260) to be sent to the external device 2254 through the communication link 2203. The telemetry circuit 2264 can also be referred to as a transceiver 2264.

The IMD 2201 can save within the memory 2260, and/or transmit to an external device (e.g., 2202), data corresponding one or more AF episodes detected by the IMD 2201, so that the data is available at a later time for further analysis. If the IMD 2201 determines that a detection of the AF episode does not correspond to an actual AF episode, the IMD can allow data corresponding to the false AF episode to be overwritten in the memory 2260 and/or can prevent data corresponding to the false AF episode from being transmitted to an external device using the transceiver 2264.

The IMD 2201 can further include magnet detection circuitry (not shown), coupled to the microcontroller 2220, to detect when a magnet is placed over the unit. A magnet may be used by a clinician to perform various test functions of IMD 2201 and/or to signal the microcontroller 2220 that the external device 2254 is in place to receive or transmit data to the microcontroller 2220 through the telemetry circuit 2264.

The IMD 2201 can further include one or more physiological sensors 2270. Such sensors are commonly referred to as "rate-responsive" sensors because they are typically used to adjust pacing stimulation rates according to the exercise state of the patient. However, the physiological sensor(s) 2270 may further be used to detect changes in cardiac output, changes in the physiological condition of the heart, or diurnal changes in activity (e.g., detecting sleep and wake states). Signals generated by the physiological sensor (s) 2270 are passed to the microcontroller 2220 for analysis. The microcontroller 2220 responds by adjusting the various pacing parameters (such as rate, AV Delay, V-V Delay, etc.) at which the atrial and ventricular pacing pulses are administered. While shown as being included within the IMD 2201, one or more physiological sensor(s) 2270 may be external to the IMD 2201, yet still be implanted within or carried by the patient. Examples of physiologic sensors include sensors that, for example, sense respiration rate, pH of blood, ventricular gradient, activity, position/posture, minute ventilation (MV), and so forth.

A battery 2272 provides operating power to all of the components in the IMD 2201. The battery 2272 is preferably capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 2272 also desirably has a predictable discharge characteristic so that elective replacement time can be detected. As one example, the IMD 2201 employs lithium/silver vanadium oxide batteries.

The IMD 2201 further includes an impedance measuring circuit 2274, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 2274 is coupled to the switch 2226 so that any desired electrode may be used. In this embodiment the IMD 2201 further includes a shocking circuit 2280 coupled to the microcontroller 2220 by a data/address bus 2282.

The embodiments described above were primarily described as being used with an IMD or system that monitors HR and/or for one or more types of arrhythmic episodes based on sensed intervals (e.g., R-R intervals). Such embodiments can alternatively be used with a non-implantable device or system (aka an external device or system) that includes at least two electrodes in contact with a person's skin and is used to monitor HR and/or for one or more types of arrhythmic episodes based on sensed intervals. More specifically, such embodiments can alternatively be used with or be implemented by a user wearable device, such as a wrist worn device, or a user wearable device designed to be worn on one or more other portions of a person's body besides a wrist, e.g., on an ankle, an upper arm, or a chest, but not limited thereto. Such a user wearable device can include electrodes that are configured to contact a person's skin, sensing circuity coupled to the electrodes and configured to obtain a signal indicative of electrical activity of a patient's heart, and at least one processor that is configured to perform one or more of the algorithms described above. Such a user wearable device (or more generally an external device or system) can monitor for AF and/or other types of arrhythmia(s) and determine when there is a false positive detection. A user wearable device can both obtain a signal indicative of electrical activity of a patient's heart and monitor a person's HR and/or for arrhythmia(s) based on R-R intervals obtained from the obtained signal. Alternatively, a user wearable device can be communicatively coupled to another external device, such as a smartphone or tablet computer, and the other external device can obtain the signal from the user wearable device and monitor a person's HR and/or for arrhythmia(s) based on R-R intervals and/or the like. The user wearable device or other external device or system can determine when there may be a false positive AF detection. Other implementations of such an external device or system are also possible and within the scope of the embodiments described herein.

Example External Device

Figure 23:
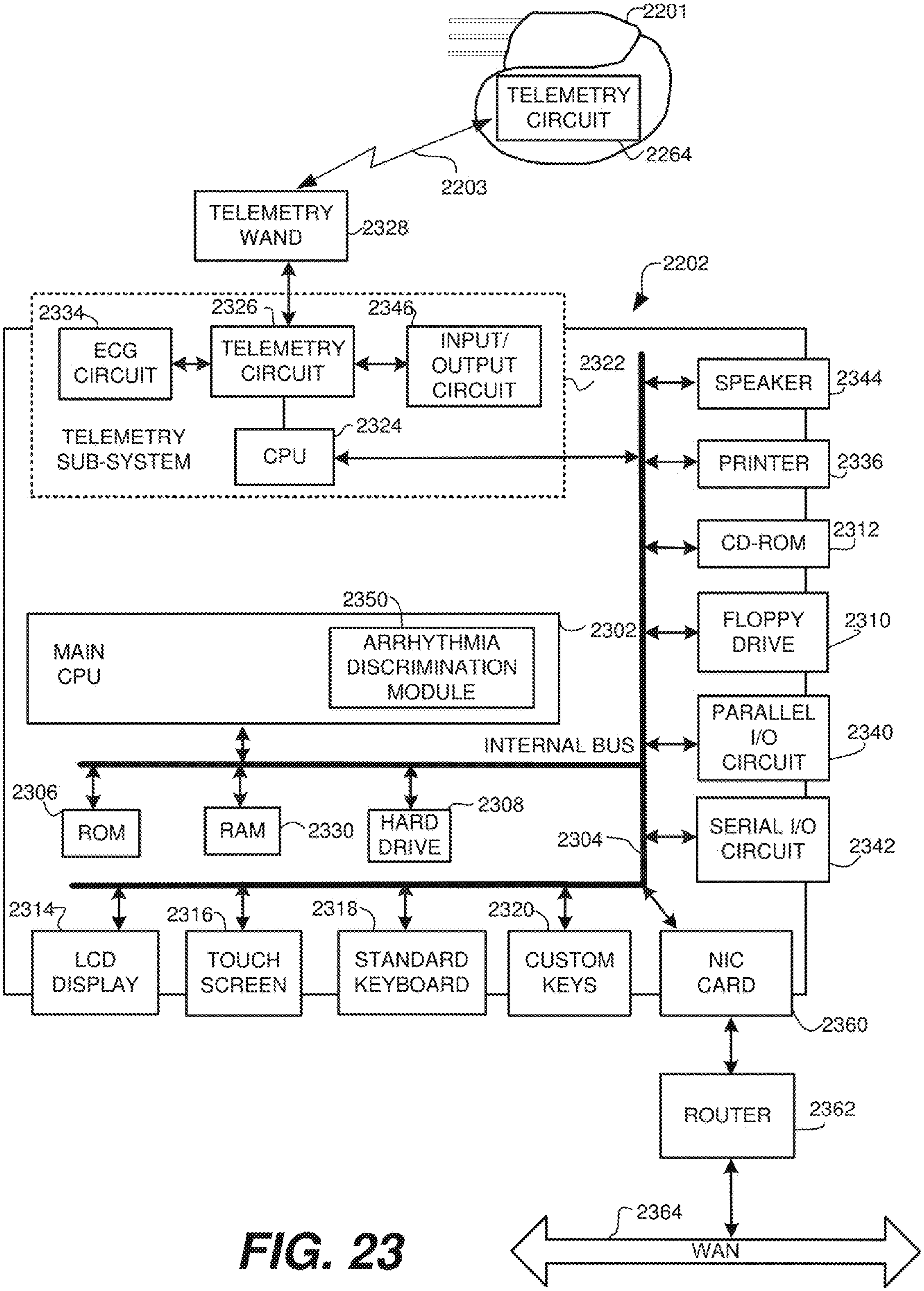
FIG. 23 shows a block diagram of one embodiment of an external device for use in communicating with and/or programming the IMD introduced in FIG. 22, and which can be used to implement certain embodiments of the present technology.

FIG. 23 illustrates example components of an example external device 2202 for use in communicating with and/or programming the IMD 2201. In certain embodiment, the external device 2202 can be used to analyze EGM segments obtained and stored by the IMD 2201. More generally, the external device 2202 may permit a physician or other authorized user to program the operation of the IMD 2201 and to retrieve and display information received from the IMD 2201 such as EGM data and device diagnostic data. Additionally, the external device 2202 may receive and display ECG data from separate external ECG leads that may be attached to the patient. Further, the external device 2202 is capable of causing the IMD to perform functions necessary to complete certain algorithms of the present invention. Depending upon the specific programming of the programmer, external device 2202 may also be capable of processing and analyzing data received from the IMD 2201 and from ECG leads 2332 to, for example, render preliminary diagnosis as to medical conditions of the patient or to the operations of the IMD 2201. Such leads 2332 can also be used to obtain an actual surface ECG, from which an ordered list of R-R intervals leading up to an AF detection may be obtained. Additionally, the external device 2202 is capable of accepting the various user inputs that are accepted in accordance with embodiments of the present invention described above.

Now, considering the components of the external device 2202 by reference to FIG. 23, operations of the external device 2202 can be controlled by a CPU 2302, which may be a generally programmable microprocessor or microcontroller or may be a dedicated processing device such as an Application Specific Integrated Circuit (ASIC) or the like. Software instructions to be performed by the CPU can be accessed via an internal bus 2304 from a Read Only Memory (ROM) 2306 and Random Access Memory (RAM) 2330. Additional software may be accessed from a hard drive 2308, floppy drive 2310, and CD ROM drive 2312, or other suitable permanent mass storage device. Depending upon the specific implementation, a Basic Input Output System (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 2314 or another suitable computer display device. To this end, the CPU may, for example, display a menu of specific programming parameters of the IMD 2201 to be programmed or may display a menu of types of diagnostic data to be retrieved and displayed. In response thereto, the physician enters various commands via either a touch screen 2316 overlaid on LCD display 2314 or through a standard keyboard 2318 supplemented by additional custom keys 2320, such as an emergency VVI (EVVI) key. The EVVI key sets the IMD 2201 to a safe VVI mode with high pacing outputs. This ensures life-sustaining pacing operation in nearly all situations but by no means is it desirable to leave cardiac stimulation device 100 in the EVVI mode at all times.

Typically, the physician initially controls the external device 2202 to retrieve data stored within the implanted medical device and to also retrieve ECG data from ECG leads coupled to the patient's myocardium. To this end, CPU 2302 transmits appropriate signals to a telemetry circuit 2322, which provides components for directly interfacing with IMD 2201. The telemetry subsystem 2322 can include its own separate CPU 2324 for coordinating the operations of the telemetry subsystem 2322. The main CPU 2302 of the external device 2202 communicates with telemetry subsystem CPU 2324 via internal bus 2304. The telemetry subsystem 2322 additionally includes a telemetry circuit 2326 connected to a telemetry wand 2328, which cooperate to receive and transmit signals electromagnetically from telemetry circuit 2264 of the IMD 2201. The telemetry wand 2328 is placed over the chest of the patient near the IMD 2201 to permit reliable transmission of data, over telemetric link 2203, between the telemetry wand and the IMD 2201. Typically, at the beginning of the programming session, the external programming device controls the IMD 2201 via appropriate signals generated by telemetry wand 2328 to output all previously recorded patient and device diagnostic information. Patient diagnostic information includes, for example, measured physiological variables data, recorded EGM data and statistical patient data such as the percentage of paced versus sensed heartbeats. Device diagnostic data includes, for example, information representative of the operation of the IMD 2201 such as lead impedances, battery voltages, battery Recommended Replacement Time (RRT) information and the like. Data retrieved from the IMD 2201 is stored by the external device 2202 either within a Random Access Memory (RAM) 2330, a hard drive 2308, within a floppy diskette placed within a floppy drive 2310, etc. Additionally, or in the alternative, data may be permanently or semi-permanently stored within a Compact Disk (CD) or other digital media disk, if the overall system is configured with a drive for recording data onto digital media disks, such as a Write Once Read Many (WORM) drive.

Patient and device diagnostic data stored within the IMD 2201 can be transferred to the external device 2202. Further, the IMD 2201 can be instructed to perform an electrode algorithms of the present invention, details of which are provided above.

The external device 2202 can also include a Network Interface Card ("NIC") 2360 to permit transmission of data to and from other computer systems via a router 2362 and Wide Area Network ("WAN") 2364. Alternatively, the external device 2202 might include a modem for communication via the Public Switched Telephone Network (PSTN). Depending upon the implementation, the modem may be connected directly to internal bus 2304 and may be connected to the internal bus via either a parallel port 2340 or a serial port 2342. Data transmitted from other computer systems may include, for example, data regarding medication prescribed, administered, or sold to the patient.

The CPU 2302 can include an arrhythmia discrimination module 2350 that can control the performance of the steps described above with reference to FIGS. 1-22, or subsets thereof, and/or can instruct the IMD 2201 to perform certain such steps.

The external device 2202 receives data from the IMD 2201, including parameters representative of the current programming state of the IMD 2201. The external device 2202 can also receive EGMs, samples thereof, and/or date indicative thereof from the IMD 2201. Under the control of the physician, external device 2202 displays the current programming parameters and permits the physician to reprogram the parameters. To this end, the physician enters appropriate commands via any of the aforementioned input devices and, under control of the CPU 2302, the programming commands are converted to specific programming parameters for transmission to the IMD 2201 via the telemetry wand 2328 to thereby reprogram the IMD 2201. Prior to reprogramming specific parameters, the physician may control the external programmer to display any or all of the data retrieved from the IMD 2201, including displays of ECGs, displays of electrodes that are candidates as cathodes and/or anodes, and statistical patient information. Any or all of the information displayed by external device 2202 may also be printed using a printer 2336.

A speaker 2344 is included for providing audible tones to the user, such as a warning beep in the event improper input is provided by the physician. Telemetry subsystem 2322 may additionally include an input/output circuit 2346 which can control the transmission of analog output signals, such as ECG signals output to an ECG machine or chart recorder. Other peripheral devices may be connected to the external device 2202 via parallel port 2340 or a serial port 2342 as well. Although one of each is shown, a plurality of Input Output (IO) ports might be provided.

With the external device 2202 configured as shown, a physician or other authorized user can retrieve, process, and display a wide range of information received from the IMD 2201 and reprogram the IMD 2201, including configurations of CRT pacing parameters, if needed. The descriptions provided herein with respect to FIG. 23 are intended merely to provide an overview of the operation of the example external device 2202 and are not intended to describe in detail every feature of the hardware and software of the device and are not intended to provide an exhaustive list of the functions performed by the device.

It is to be understood that the subject matter described herein is not limited in its application to the details of construction and the arrangement of components set forth in the description herein or illustrated in the drawings hereof.

The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in the various flow diagrams. It would also be possible to just perform a subset of the steps shown in the various flow diagrams. For another example, it is possible to change the boundaries of some of the block diagrams.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. An implantable medical device (IMD), comprising:

at least one electrode configured to sense an electrogram (EGM) or electrocardiogram (ECG) signal indicative of cardiac electrical activity;

a battery;

at least one processor powered by the battery and configured to:

determine R-R intervals based on R-waves detected within the EGM or ECG signal;

determine a measure of variability of the R-R intervals;
detect atrial fibrillation (AF) based on the measure of variability of the R-R-intervals;
in response the AF detection based on the measure of variability of the R-R intervals, use two or more time-based AF discriminators to analyze two or more temporal features of the R-R intervals within a window leading up to the AF detection to thereby determine whether to classify the AF detection as a false positive based on at least one of the two or more temporal features;
in response to the AF detection not being classified as a false positive using at least one of the two or more time-based AF discriminators, use one or more morphology-based AF discriminators to analyze one or more morphological features of the EGM or ECG signal within the window leading up to the AF detection to thereby determine whether to classify the AF detection as a false positive based on the one or more morphological features; and
trigger one or more AF responses, in response to none of the two or more time-based and the one or more morphology-based AF discriminators being used to classify the AF detection as a false positive;
wherein use of each of the two or more time-based AF discriminators is less computationally intensive than, and consumes less power from the battery than, use of each of the one or more morphology-based AF discriminator; and
wherein the one or more AF responses are not been triggered, if at least one of the two or more time-based or the one or more morphology-based AF discriminators classified the AF detection as a false positive.

2. The IMD of claim 1, wherein the two or more time-based AF discriminators, used to analyze the two or more temporal features of the R-R intervals within the window leading up to the AF detection, are used to determine at least two of the following:
whether a sudden heart rate change associated with AF, detected based on the R-R intervals within the window leading up to the AF detection, is present;
whether an extent of false R-R intervals due to R-wave undersensing or intermittent AV conduction block, detected based on the R-R intervals within the window leading up to the AF detection, exceeds a corresponding threshold;
whether an extent of false R-R intervals due to at least one of T-wave or P-wave oversensing, detected based on the R-R intervals within the window leading up to the AF detection, exceeds a corresponding threshold; or
whether a dominant repeated R-R interval pattern, detected based on the R-R intervals within the window leading up to the AF detection, exceeds a corresponding threshold.

3. The IMD of claim 2, wherein the one or more morphology-based AF discriminators, used to analyze the one or more morphological features of the EGM or ECG signal in response to the AF detection not being classified as a false positive using at least one of the two or more time-based AF discriminators, is/are used to determine at least one of the following:
whether an extent of over-sensed P-waves, detected based on magnitudes of the EGM or ECG signal within the window leading up to the AF detection, exceeds a corresponding threshold; or
whether an extent of actual P-waves, detected based on comparisons between one or more P-wave templates and the EGM or ECG signal within the window leading up to the AF detection, exceeds a corresponding threshold.

4. The IMD of claim 1, wherein the at least one processor is configured to use a plurality of the time-based AF discriminators and a plurality of the morphology-based AF discriminators over time when determining whether to classify each of a plurality of AF detections as a false positive, the at least one processor further configured to:
track how often individual ones of the time-based and the morphology-based AF discriminators are used to classify the AF detections as false positives; and
selectively disable one or more of the time-based or the morphology-based AF discriminators based on how often individual ones of the time-based and the morphology-based AF discriminators are used to classify the AF detections as false positives;
wherein disabling the one or more of the time-based or the morphology-based AF discriminators conserves processing recourses of the at least one processor and conserves power of the battery, compared to if the one or more of the time-based or the morphology-based AF discriminators are not disabled.

5. The IMD of claim 1, wherein the at least one processor is configured to use a plurality of the time-based AF discriminators and a plurality of the morphology-based AF discriminators over time when determining whether to classify each of a plurality of AF detections as a false positive, the at least one processor further configured to:
for each condition of a plurality of different conditions, track how often individual ones of the time-based and the morphology-based AF discriminators are used to classify the AF detections as false positives during the condition; and
for a said condition, selectively disable one or more of the time-based or the morphology-based AF discriminators based on how often individual ones of the time-based and the morphology-based AF discriminators are used to classify the AF detections as false positives during the said condition.

6. The IMD of claim 5, wherein the plurality of different conditions comprise:
a plurality of different patient activity levels;
a plurality of different heart rate ranges;
a plurality of different times of day; or
a plurality of different respiration patterns.

7. The IMD of claim 1, further comprising a memory that is communicatively coupled to the at least one processor, wherein the at least one processor is further configured to:
prevent transmitting, to an external device that is communicatively coupled to a patient care network, of data corresponding to an AF detection that is detected by the IMD but is thereafter determined by the IMD as being a false positive detection;
allow overwriting in the memory of stored data corresponding to the AF detection that was detected by the IMD but is thereafter determined by the IMD as being a false positive detection; or
not store in the memory of the IMD data corresponding to the AF detection that is detected by the IMD but is thereafter determined by the IMD as being a false positive detection.

8. The IMD of claim 1, wherein the at least one processor is further configured to classify a said AF detection as a true positive detection in response to none of the time-based and the morphology-based AF discriminators being used to classify the AF detection as a false positive.

9. The IMD of claim 1, the IMD includes a memory to which the at least one processor is communicatively coupled, and wherein the one or more AF responses, which the at least one processor is configured to trigger in response to none of the time-based and the morphology-based AF discriminators being used to classify the AF detection as a false positive, include at least one of the following:

cause storing of data corresponding to the AF detection in the memory of the IMD; or cause transmitting of data corresponding to the AF detection from the IMD to an external device;

wherein the at least one processor would neither cause the storing nor cause the transmitting if at least one of the two or more time-based or the one or more morphology-based AF discriminators classified the AF detection as a false positive.

10. The IMD of claim 1, wherein the one or more AF responses, which the at least one processor is configured to trigger in response to none of the time-based and the morphology-based AF discriminators being used to classify the AF detection as a false positive, include causing delivery of pacing or shock therapy to convert the AF to a normal sinus rhythm.

11. The IMD of claim 1, further comprising a memory to which the at least one processor is communicatively coupled, and wherein:

the one or more AF responses, that the at least one processor is configured to trigger in response to none of the time-based and the morphology-based AF discriminators being used to classify the AF detection as a false positive, includes causing data corresponding to the AF detection to be stored in the memory so that the data is available for later analysis; and the at least one processor is configured to not cause the data corresponding to the AF detection to be stored in the memory in response to at least one of the two or more time-based or the one or more morphology-based AF discriminators being used to classify the AF detection as a false positive.

* * * * *